US011185583B2

(12) United States Patent
Gosselin et al.

(10) Patent No.: US 11,185,583 B2
(45) Date of Patent: Nov. 30, 2021

(54) MULTI-FUNCTIONAL MUCOSAL VACCINE PLATFORM

(71) Applicants: Albany Medical College, Albany, NY (US); University of Washington, Seattle, WA (US)

(72) Inventors: Edmund J. Gosselin, Glenmont, NY (US); Deborah Fuller, Bainbridge Island, WA (US)

(73) Assignees: Albany Medical College, Albany, NY (US); University of Washington through its Center for Commercialization, Seattle, WA (US)

( * ) Notice: Subject to any disclaimer, the term of this patent is extended or adjusted under 35 U.S.C. 154(b) by 114 days.

(21) Appl. No.: 15/117,354

(22) PCT Filed: Feb. 11, 2015

(86) PCT No.: PCT/US2015/015507
§ 371 (c)(1),
(2) Date: Aug. 8, 2016

(87) PCT Pub. No.: WO2015/123359
PCT Pub. Date: Aug. 20, 2015

(65) Prior Publication Data

US 2017/0035878 A1 Feb. 9, 2017

Related U.S. Application Data

(60) Provisional application No. 61/938,607, filed on Feb. 11, 2014.

(51) Int. Cl.

| | |
|---|---|
| ***C07K 16/00*** | (2006.01) |
| ***C12P 21/08*** | (2006.01) |
| ***A61K 39/385*** | (2006.01) |
| ***A61K 39/09*** | (2006.01) |
| ***A61K 39/00*** | (2006.01) |
| ***A61K 39/02*** | (2006.01) |
| ***C07K 14/195*** | (2006.01) |
| ***C07K 14/315*** | (2006.01) |
| ***C07K 14/47*** | (2006.01) |
| ***C07K 14/765*** | (2006.01) |
| ***C07K 16/28*** | (2006.01) |
| *C07K 1/00* | (2006.01) |

(52) U.S. Cl.
CPC ........ *A61K 39/385* (2013.01); *A61K 39/0011* (2013.01); *A61K 39/001106* (2018.08); *A61K 39/001151* (2018.08); *A61K 39/001156* (2018.08); *A61K 39/001157* (2018.08); *A61K 39/001164* (2018.08); *A61K 39/001171* (2018.08); *A61K 39/001184* (2018.08); *A61K 39/001186* (2018.08); *A61K 39/001188* (2018.08); *A61K 39/001191* (2018.08); *A61K 39/001192* (2018.08); *A61K 39/001194* (2018.08); *A61K 39/001197* (2018.08); *A61K 39/02* (2013.01); *A61K 39/092* (2013.01); *C07K 14/195* (2013.01); *C07K 14/3156* (2013.01); *C07K 14/4748* (2013.01); *C07K 14/765* (2013.01); *C07K 16/283* (2013.01); *A61K 2039/53* (2013.01); *A61K 2039/543* (2013.01); *A61K 2039/545* (2013.01); *A61K 2039/575* (2013.01); *A61K 2039/6056* (2013.01); *A61K 2039/6081* (2013.01); *C07K 2317/24* (2013.01); *C07K 2317/35* (2013.01); *C07K 2317/52* (2013.01); *C07K 2317/55* (2013.01); *C07K 2317/77* (2013.01); *C07K 2319/03* (2013.01); *C07K 2319/30* (2013.01); *C07K 2319/31* (2013.01); *C07K 2319/40* (2013.01)

(58) Field of Classification Search
None
See application file for complete search history.

(56) References Cited

U.S. PATENT DOCUMENTS

| | | | | |
|---|---|---|---|---|
| 6,277,375 B1 * | 8/2001 | Ward | C07K 16/06 424/133.1 |
| 7,378,504 B2 * | 5/2008 | Graziano | C07K 16/283 530/387.1 |

OTHER PUBLICATIONS

Lu et al. Journal of Virology, Oct. 2011, p. 10542-10553. (Year: 2011).*
Bitsaktsis et al. Infection and Immunity. 2012 80;3:1166-1180 (Year: 2012).*
Ye et al. Nature Biotechnology. 2011. 29:158-163 (Year: 2011).*
Kuo et al. mAbs. Mar. 2011;5:422-430. (Year: 2011).*
Chen et al., Cross-protection against a lethal influenza virus infection by DNA vaccine to neuraminidase, Vaccine, 18:3214-3222 (2000).
McGhee, A mucosal gateway for vaccines, Nature Biotechnology, 39:136-138 (2011).
Guyre et al., Receptor Modulation by FcγRI-Specific Fusion Proteins Is Dependent on Receptor Number and Modified by IgG1, J Immunol, 167:6303-6311 (2001).
Bitsaktsis et al., Mucosal Immunization with an Unadjuvanted Vaccine That Targets *Streptococcus pneumoniae* PspAto Human Fcγ Receptor Type I Protects against Pneumococcal Infection through Complement- and Lactoferrin-Mediated Bactericidal Activity, Infection and Immunity, 80:1166-1180 (2012).

(Continued)

*Primary Examiner* — Chun W Dahle
(74) *Attorney, Agent, or Firm* — Nevrivy Patent Law Group P.L.L.C.

(57) ABSTRACT

An immunogenic fusion protein for use as a mucosal vaccine is provided, which includes: i) one or more FcyR1-binding domains; ii) one or more antigens from one or more infectious disease organisms; and iii) one or more FcRn-binding domains.

2 Claims, 20 Drawing Sheets

Specification includes a Sequence Listing.

(56) References Cited

OTHER PUBLICATIONS

Rawool et al., Utilization of Fc Receptors as a Mucosal Vaccine Strategy against an Intracellular Bacterium, *Francisella tularensis*, J Immunol, 180:5548-5557 (2008).
Iglesias et al., Multiple mechanisms mediate enhanced immunity generated by mAb-inactivated F. tularensis immunogen, Immunology and Cell Biology, 91:139-148 (2013).
Keler et al., Targeting Weak Antigens to CD64 Elicits Potent Humoral Responses in Human CD64 Transgenic Mice, J Immunol, 165:6738-6742 (2000).
Lu, Heterologous prime-boost vaccination, Current Opinion in Immunology, 21:346-351 (2009).
Chaudhury et al., Albumin Binding to FcRn: Distinct from the FcRn—IgG Interaction, Biochemistry, 45:4983-4990 (2006).
Kenanova et al., Tuning the serum persistence of human serum albumin domain III:diabody fusion proteins, Protein Engineering, Design & Selection, 23:789-798 (2010).
Montfoort et al., Fcγ Receptor IIb Strongly Regulates Fcγ Receptor-Facilitated T Cell Activation by Dendritic Cells, J Immunol, 189:92-101 (2012).
Boruchov et al., Activating and inhibitory IgG Fc receptors on human DCs mediate opposing functions, The Journal of Clinical Investigation, 115:2914-2913 (2005).
Darrieux et al., Fusion Proteins Containing Family 1 and Family 2 PspA Fragments Elicit Protection against *Streptococcus pneumoniae* That Correlates with Antibody-Mediated Enhancement of Complement Deposition, Infection and Immunity, 75:5930-5938 (2007).
Pertmer et al., Gene gun-based nucleic acid immunization: elicitation of humoral and cytotoxic T lymphocyte responses following epidermal delivery of nanogram quantities of DNA, Vaccine, 13:1427-1430 (1995).
Payne et al., Particle-mediated DNA vaccination of mice, monkeys and men: Looking beyond the dogma, Molecular Therapeutics, 4:459-466 (2002).
Haynes, Particle-mediated DNA vaccine delivery to the skin, Expert Opin. Biol. Ther., 4:889-900 (2004).
Dean et al., Powder and particle-mediated approaches for delivery of DNA and protein vaccines into the epidermis, Comp. Immun. Microbiol. Infect. Dis., 26:373-388 (2003).
Uddowla et al., Effect of adjuvants and route of immunizations on the immune response to recombinant plague antigens, Vaccine, 25:7984-7993 (2007).
Haynes et al., Induction and characterization of humoral and cellular immune responses elicited via gene gun-mediated nucleic acid immunization, Advanced Drug Delivery Reviews, 2:3-18 (1996).
Loudon et al., GM-CSF Increases Mucosal and Systemic Immunogenicity of an H1N1 Influenza DNA Vaccine Administered into the Epidermis of Non-Human Primates, PLoS ONE, 5:e11021 (2010).
Fuller et al., Induction of Mucosal Protection against Primary, Heterologous Simian Immunodeficiency Virus by a DNA Vaccine, Journal of Virology, 76:3309-3317 (2002).
Czerkinsky et al., Mucosal Delivery Routes for Optimal Immunization: Targeting Immunity to the Right Tissues, Current Topics in Microbiology and Immunology, 354:1-18 (2012).
Condon et al., DNA-based immunization by in vivo transfection of dendritic cells, Nature Medicine, 2:1122-1128 (1996).
Lawson et al., Mucosal Immune Responses Induced by Transcutaneous Vaccines, Current Topics in Microbiology and Immunology, 354:19-37 (2012).
Torrieri-Dramard et al., Intranasal DNA Vaccination Induces Potent Mucosal and Systemic Immune Responses and Cross-protective Immunity Against Influenza Viruses, The American Society of Gene & Cell Therapy, 19:602-611 (2011).
Shim et al., Intranasal immunization with plasmid DNA encoding spike protein of SARS-coronavirus/polyethylenimine nanoparticles elicits antigenspecific humoral and cellular immune responses, BMC Immunology, 11:1-9 (2010).
Roy et al., Induction of antigen-specific CD8+ T cells, T helper cells, and protective levels of antibody in humans by particle-mediated administration of a hepatitis B virus DNA vaccine, Vaccine, 19:764-778 (2001).
Drape et al., Epidermal DNA vaccine for influenza is immunogenic in humans, Vaccine, 24:4475-4481 (2006).
Briles et al., Immunization of Humans with Recombinant Pneumococcal Surface Protein A (rPspA) Elicits Antibodies That Passively Protect Mice from Fatal Infection with *Streptococcus pneumoniae* Bearing Heterologous PspA, The Journal of Infectious Diseases, 182:1694-1701 (2000).
Nguyen et al., Intranasal immunization with recombinant PspA fused with a flagellin enhances cross-protective immunity against *Streptococcus pneumoniae* infection in mice, Vaccine, 29:5731-5739 (2011).
Miyaji et al., Analysis of Serum Cross-Reactivity and Cross-Protection Elicited by Immunization with DNA Vaccines against *Streptococcus pneumoniae* Expressing PspA Fragments from Different Clades, Infection and Immunity, 70:5086-5090 (2002).
Fuller et al., Preclinical and clinical progress of particle-mediated DNA vaccines for infectious diseases, Methods, 40:86-97 (2006).
Yager et al., Prospects for developing an effective particle-mediated DNA vaccine against influenza, Expert Rev. Vaccines, 8:1205-1220 (2009).
Adamova et al., Enhanced Antigen-Specific Antibody and Cytokine Responses When Targeting Antigen to Human FcGAMMA Receptor Type I Using an Anti-Human FcGAMMA Receptor Type I—Streptavidin Fusion Protein in an Adjuvant-Free System, Immunological Investigations, 34:417-429 (2005).
Wallace et al., FcγRI blockade and modulation for immunotherapy, Cancer Immunol Immunother, 45:137-141 (1997).
Daniels et al., The Proline-Rich Region of Pneumococcal Surface Proteins A and C Contains Surface-Accessible Epitopes Common to All Pneumococci and Elicits Antibody-Mediated Protection against Sepsis, Infection and Immunity, 78:2163-2172 (2010).
Andersen et al., Cross-species Binding Analyses of Mouse and Human Neonatal Fc Receptor Show Dramatic Differences in Immunoglobulin G and Albumin Binding, The Journal of Biological Chemistry, 285:4826-4836 (2010).
Hollingshead et al., Diversity of PspA: Mosaic Genes and Evidence for Past Recombination in *Streptococcus pneumoniae*, Infection and Immunity, 68:5889-5900 (2000).
Kobayashi et al., FcRn-mediated transcytosis of immunoglobulin G in human renal proximal tubular epithelial cells, Am J Physiol Renal Physiol, 282:358-365 (2002).
Dickinson et al., Bidirectional FcRn-dependent IgG transport in a polarized human intestinal epithelial cell line, J. Clin. Invest., 104:903-911 (1999).
Ye et al., Efficient Mucosal Delivery of Vaccine Using the FcRn-Mediated IgG Transfer Pathway, Nat Biotechnol, 29:158-163(2011).
Lu et al., A Neonatal Fc Receptor-Targeted Mucosal Vaccine Strategy Effectively Induces HIV-1 Antigen-Specific Immunity to Genital Infection, Journal of Virology, 85:10542-10553 (2011).
Gosselin et al., Fc receptor-targeted mucosal vaccination as a novel strategy for the generation of enhanced immunity against mucosal and non-mucosal pathogens, Arch. Immunol. Ther. Exp., 57:311-323 (2009).
Mattos Areas et al., Expression and characterization of cholera toxin B—pneumococcal surface adhesin A fusion protein in *Escherichia coli*: ability of CTB-PsaA to induce humoral immune response in mice, Biochemical and Biophysical Research Communications, 321:192-196 (2004).
Mestecky et al., Prospects for Human Mucosal Vaccines, Deartments of Microbiology and Medicine Immunobiology Vaccine Center, 13-23 (1992).
Neutra et al., Mucosal vaccines: the promise and the challenge, Nature Reviews Immunology, 6:148-158 (2006).
Holmgren et al., Mucosal vaccines: the promise and the challenge, Nature Medicine Supplement, 11:45-53 (2005).
Kensil et al., Current Vaccine Adjuvants: An Overview of a Diverse Class, Frontiers in Bioscience, 9:2972-2988 (2004).

(56) References Cited

OTHER PUBLICATIONS

Tanghe et al., Improved Immunogenicity and Protective Efficacy of a Tuberculosis DNA Vaccine Encoding Ag85 by Protein Boosting, Infection and Immunity, 69:3041-3047 (2001).
Otten et al., Enhanced Potency of Plasmid DNA Microparticle Human Immunodeficiency Virus Vaccines in Rhesus Macaques by Using a Priming-Boosting Regimen with Recombinant Proteins, Journal of Virology, 79:8189-8200 (2005).
Wei et al., Induction of Broadly Neutralizing H1N1 Influenza Antibodies by Vaccination, Science, 329:1060-1064 (2010).
Haddad et al., Characterization of Antibody Responses to a Plasmodium falciparum Blood-Stage Antigen Induced by a DNA Prime/Protein Boost Immunization Protocol, Scand. J. Immunol., 49:06-514 (1999).
Leung et al., Immunogenicity of HIV-1 Env and Gag in baboons using a DNA prime/protein boost regimen, AIDS, 18:991-1001 (2004).

* cited by examiner

Fig. 1: Predicted Trafficking of the hFcRn/hFcγRI-Targeted FP
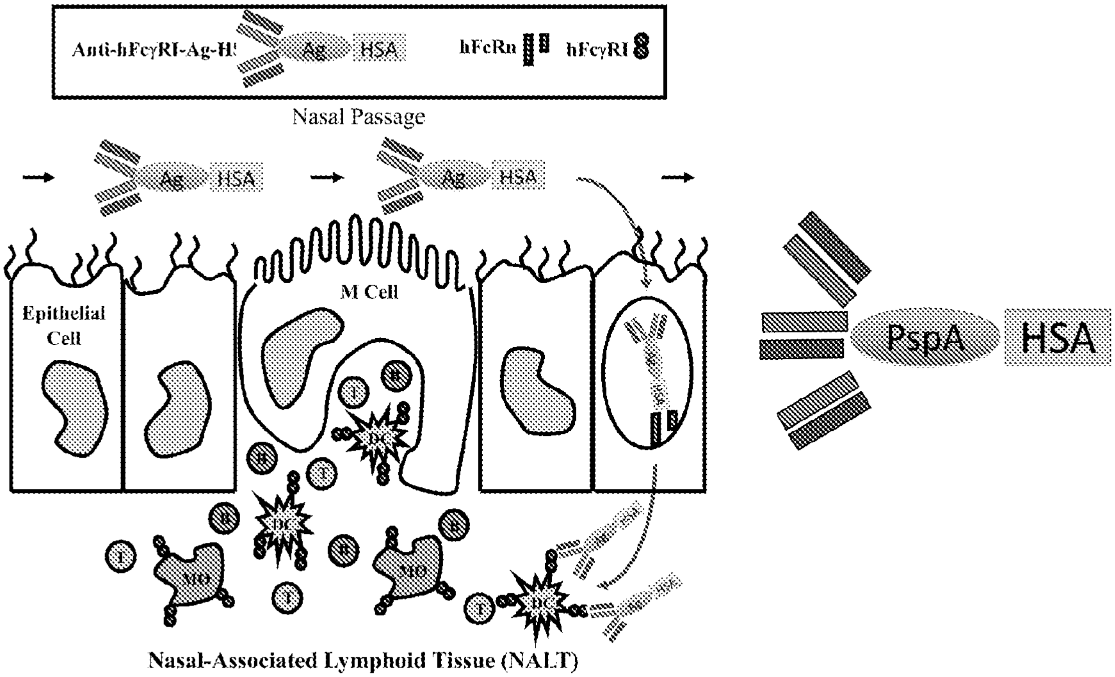

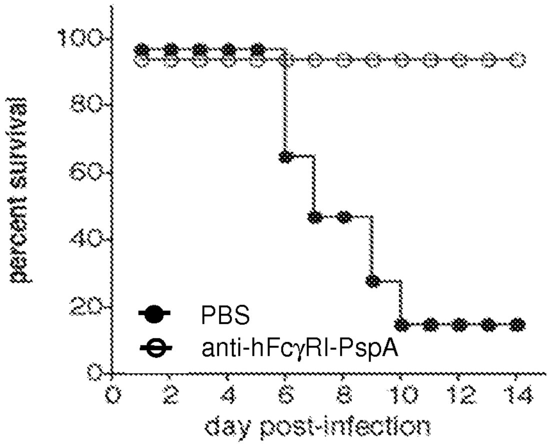

Fig. 2: **Anti-hFcγRI-PspA FP enhances protection against *Sp* challenge in hFcγRI Tg mice, in the absence of adjuvant.** C57BL/6 hFcγRI Tg mice (5-8 mice/group) were immunized i.n. with PBS or 25 μg of anti-hFcγRI-PspA FP (day 0) and boosted on days 14 and 28. Two weeks post-final boost, mice were challenged i.n. with *Sp* ($1 \times 10^6$ CFU), and survival was monitored for 21 days. Representative survival curves from a minimum of 3 experiments are presented. $p < 0.005$ (PBS vs. anti-hFcγRI-PspA FP-immunized group).

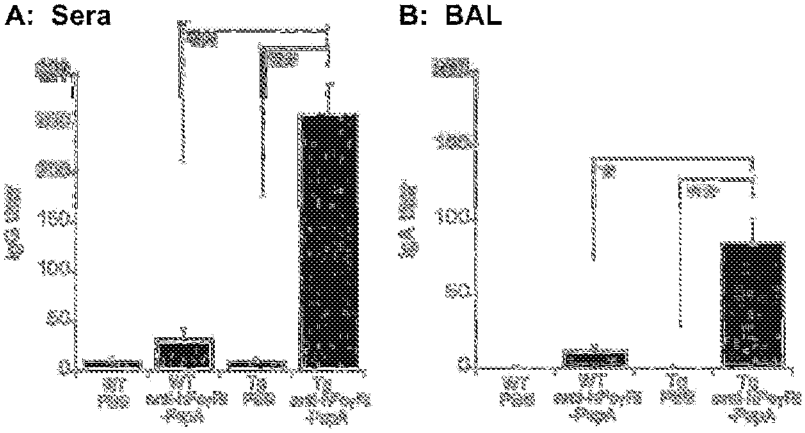

Fig. 3: **Targeting PspA to hFcγRI enhances *Sp*-specific Ab responses in hFcγRI Tg mice.** C57BL/6 WT and hFcγRI Tg mice (4-6/group) were immunized i.n. with PBS or with 25 μg of bivalent anti-hFcγRI-PspA (day 0) and boosted on days 14 and 28. On day 42 serum and BAL were collected, and the *Sp*-specific IgG (A) and IgA (B) were measured by ELISA, respectively. Results are representative of 2 independent experiments (*, $P < 0.1$; **, $P < 0.05$).

Fig. 4: Status of FP Generation
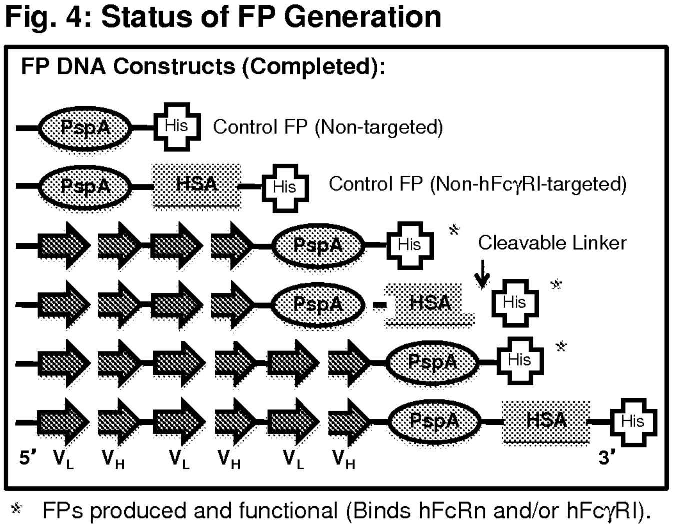
* FPs produced and functional (Binds hFcRn and/or hFcγRI).

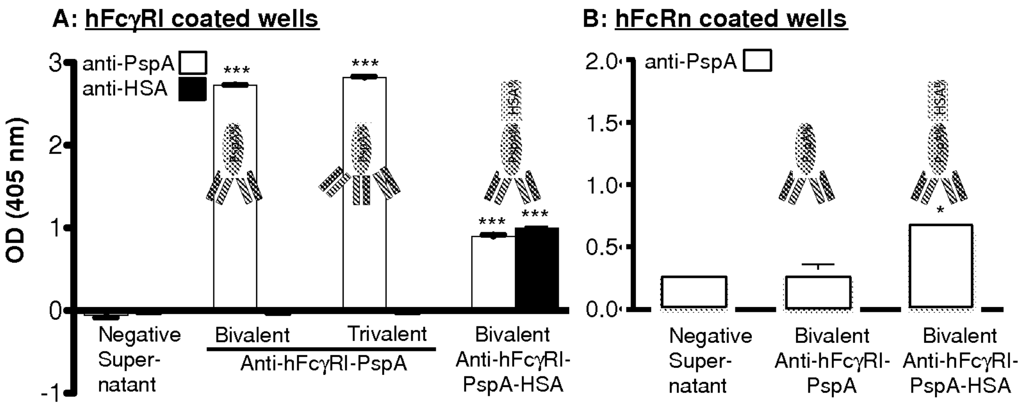

Fig. 5: Trivalent anti-hFcγRI-PspA binds hFcγRI and bivalent anti-hFcγRI-PspA-HSA binds hFcγRI and hFcRn. Supernatants from FP transfected NSO cells were screened for FP binding to hFcRn and/or hFcγRI by ELISA. To hFcγRI-coated wells (A), media or NSO supernatant from non-transfected or FP transfected cells were added overnight at 4°C followed by 3 washes, addition of Rb anti-PspA or Rb anti-HSA Ab for 2 hrs at 4°C, 3 washes, goat anti-Rb IgG-AP for 2 hrs at 4°C, 3 washes, and AP substrate at room temperature. To hFcRn coated wells (B), supernatants were added and the above process repeated using Rb anti-PspA Ab only. In this case, all reagents, including supernatants, were adjusted to Ph 6.0 (required for FcRn binding). ODs from media controls were subtracted from sample ODs. FP concentrations were not equalized for these assays, potentially explaining signal variability between FP samples. * $P < 0.05$, *** $p < 0.0001$.

Fig. 6a: Current and Proposed FP Formulations
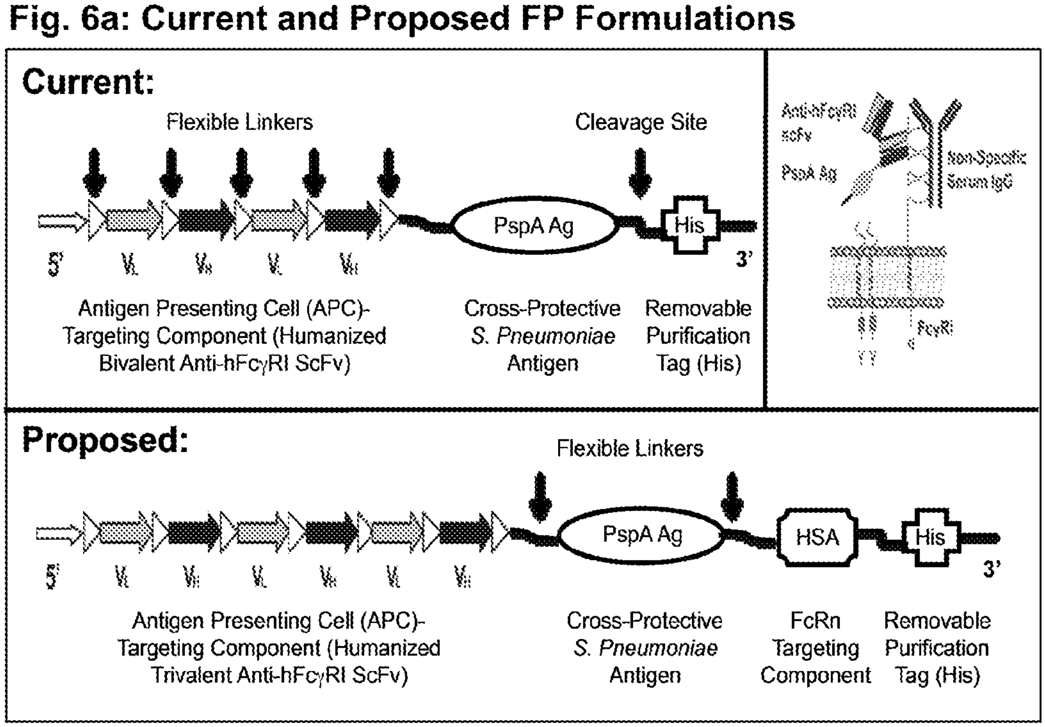

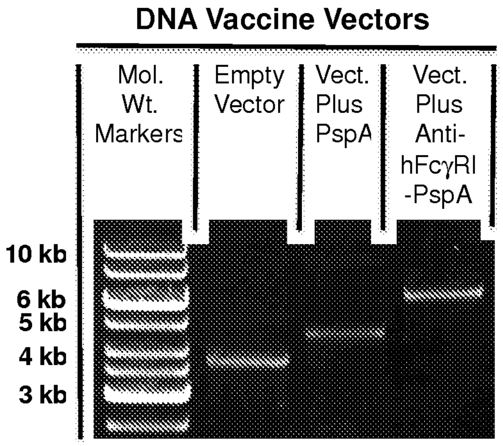
<u>Fig. 7:</u> Generation of DNA vaccine vectors. DNA for PspA and bivalent anti-hFcγRI-PspA FP were inserted into pJV7563 (3.759 kb) to produce pJV7563-PspA (4.665 kb) and pJV7563-Anti-hFcγRI-PspA (6.333 kb). The plasmid DNA was linearized by digestion with NheI before agarose gel electrophoresis.

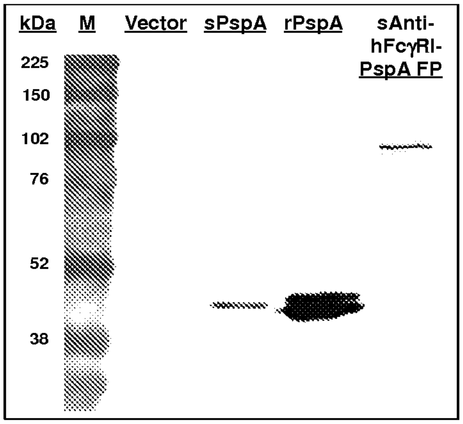

Fig. 8: Secretion of soluble PspA (sPspA) and soluble anti-hFcγRI-PspA FP (sAnti-hFcγRI-PspA) by cells transfected with DNA vaccine vectors. NIH-3T3 (Mouse-embryonic fibroblast) cells were transfected with DNA lipofectamine complexes. After 72h incubation, supernatants were harvested. Total proteins in supernatants were separated by SDS-polyacrylamide gel electrophoresis and transferred to nitrocellulose membranes. The membranes were then incubated sequentially with PspA specific Ab and then AP-conjugated secondary Ab. The nitrocellulose membranes were then developed with 5-bromo-4-chloro-3-indolyl-phosphate-nitrobluetetrazolium substrate. Empty vector (Vector) and purified recombinant PspA (rPspA) were used as negative and positive controls, respectively. Molecular weight markers are also depicted (M).

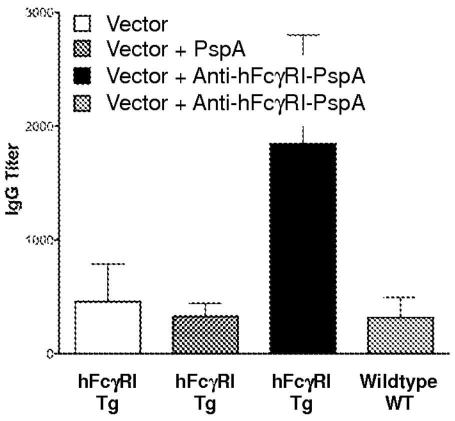

**Fig. 9: Generation of *Sp*-specific IgG following i.n. immunization with PspA versus anti-hFcγRI-PspA FP DNA vaccine using hFcγRI Tg versus WT mice.** Human FcγRI Tg or WT mice were immunized with empty vector, vector containing PspA DNA, or vector containing anti-hFcγRI-PspA FP DNA. Each DNA vaccine was mixed with PolyEthyleneImine (PEI) and 5% Glucose, and kept for 15 min at room temperature for DNA-PEI complex formation prior to administration. Mice 6-8 weeks of age were then immunized by i.n. route on days 0 and 28. Specifically, mice were anesthetized and 40 μl of PEI-DNA complex containing 4.2 pmole DNA was administered drop-wise into alternating nostrils. Sera were collected 14 days post-boost. In this preliminary study, data represents the mean of 3 mice/group ± SE. Additional studies will now be conducted with 8 mice per group.

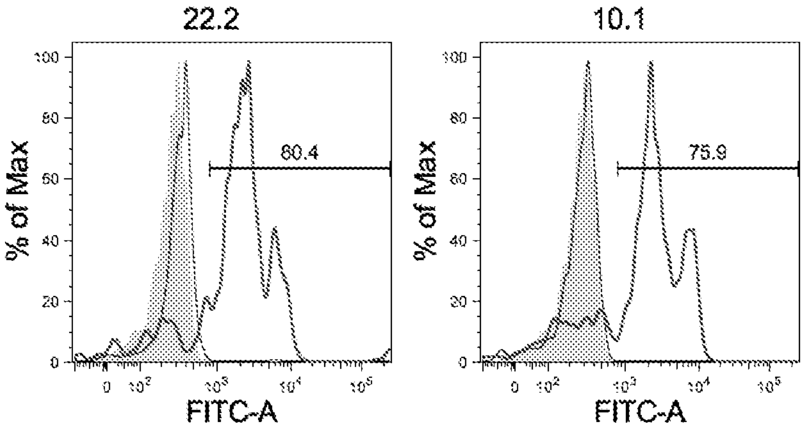
<u>Fig 10:</u> The mAb 22.2 from which the anti-hFcγRI-PspA FP was generated, also cross-reacts with NHP FcγRI. Anti-hFcγRI mAbs 22.2 (red) and 10.1, recognize and bind to FcγRI on NHP PBMCs. Isoptype controls are blue.

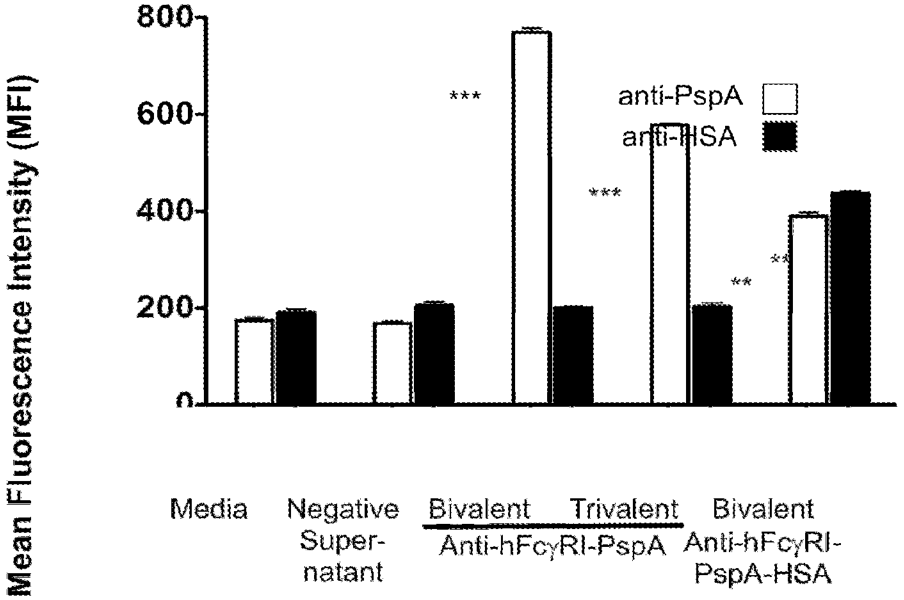

Fig. 11: Trivalent and HSA-containing FPs bind hFcγRI on hFcγRI-expressing U937 cells: Supernatants from FP construct-transfected NSO cells were screened by flow cytometry for the presence of FPs and the ability of trimeric and HSA-containing/FcRn-binding FPs to bind hFcγRI on U937 cells. Briefly, hFcγRI-expressing U937 cells were incubated for 2 hrs at 4° C with culture medium, supernatant from non-transfected NSO cells, or supernatant from FP transfected cells in the presence of human IgG (to block non-specific FcR binding of Rb Abs), followed by 3 washes, a 1 h incubation with Rb anti-PspA or Rb anti-HSA Ab, 3 washes, and a 30 min incubation with goat anti-Rb IgG-FITC. Cells were then washed, fixed, and analyzed by flow cytometry.  $P < 0.005$, * $p < 0.0001$ Fig 12 Map of pJG582 Vector
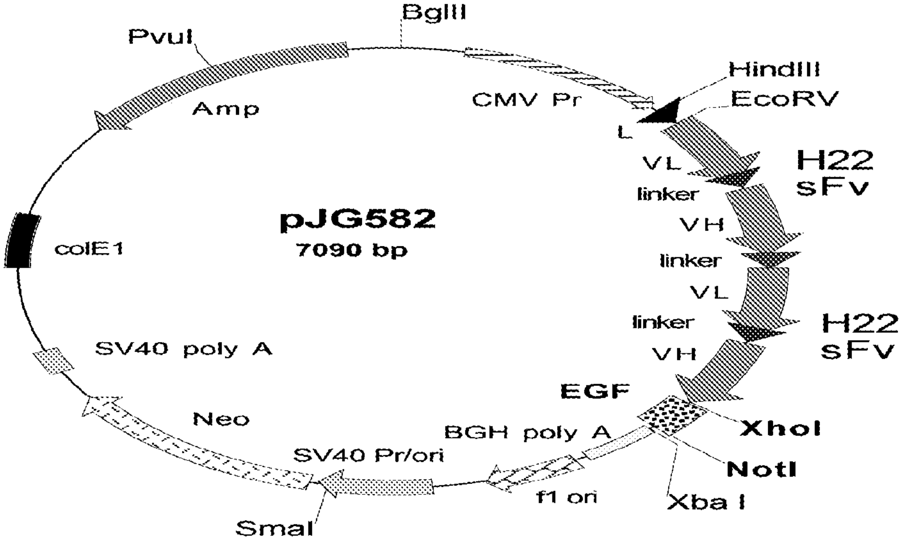
PspA
BN

Fig. 13: Status of FP and DNA Vaccine Constructs

\*   FP produced and functional (Binds hFcRn and/or hFcγRI).
\*\*  Sequences to be incorporated into DNA vaccine vectors.
\*\*\* DNA vaccine vector generated.

Fig. 14. Map of pJV-7563 Vector (No secretion signal)
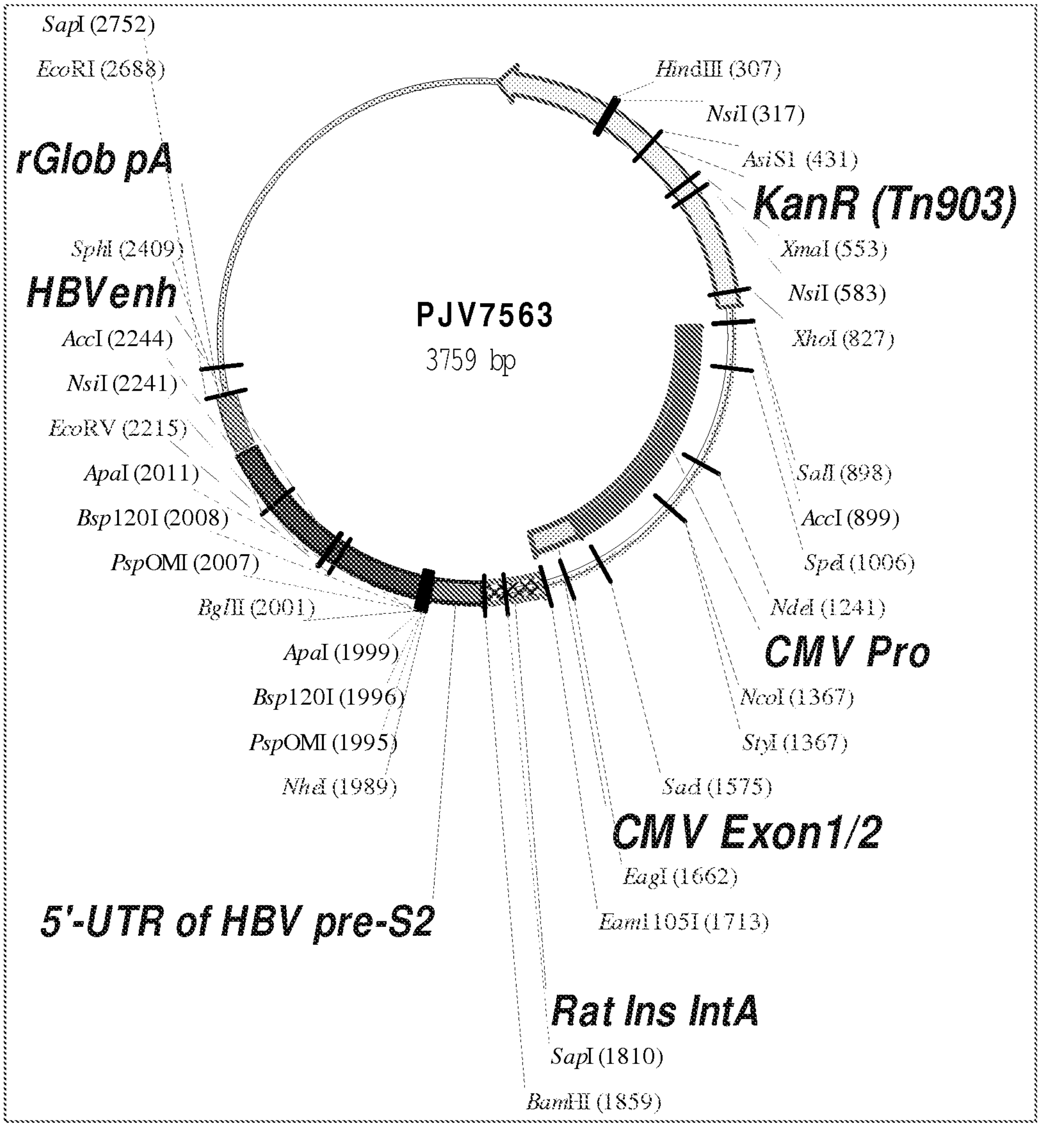

Fig. 15 Map of pUW-160s Vector (Contains secretion signal)
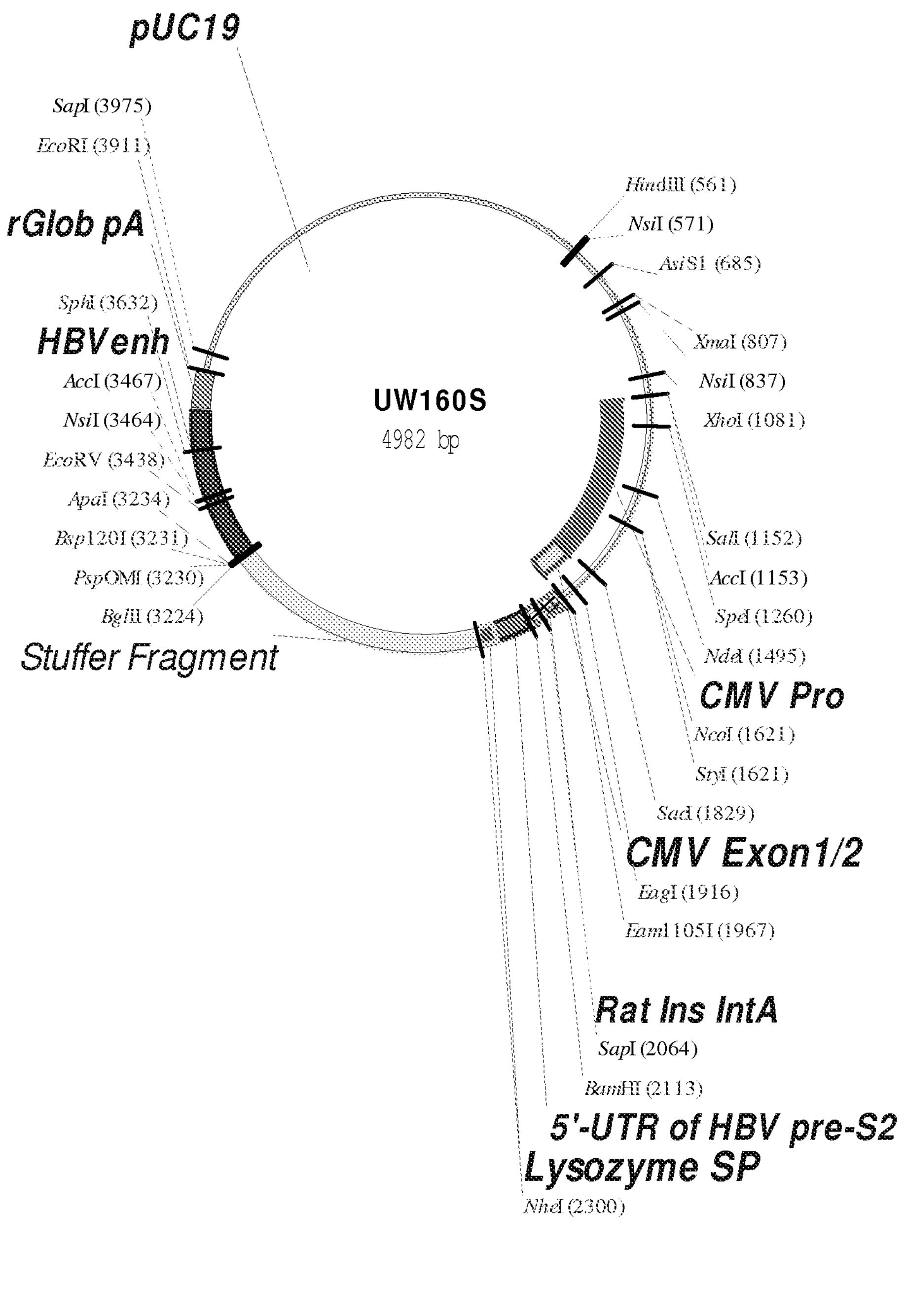

Fig. 16. Trivalent Anti-FcγRI---PspA
Construct A
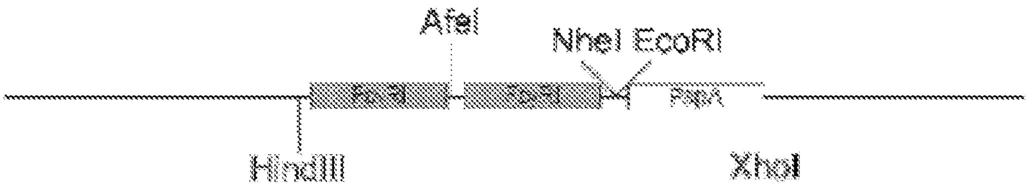
Construct B
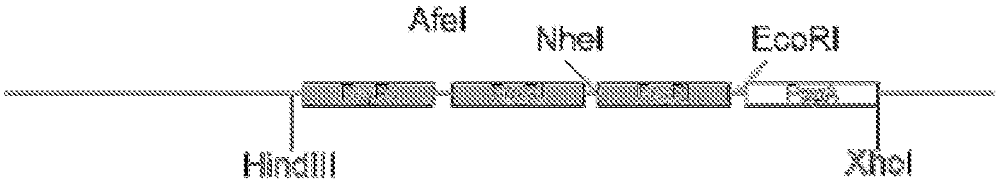

Fig. 17. Bivalent Anti-FcγRI---PspA-HuSA
Construct C
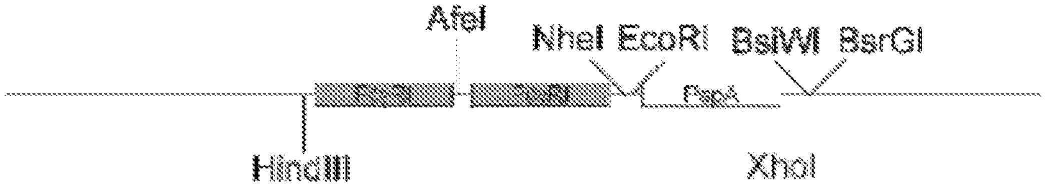
Construct D
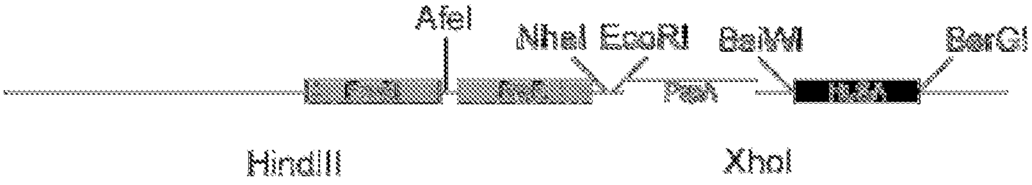

Fig. 18. Trivalent Anti-FcγRI---PspA-HuSA
Construct E
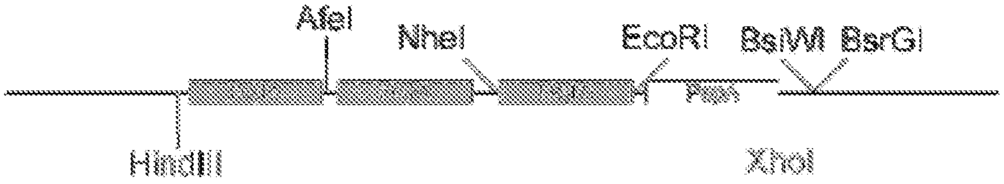
(Construct F)
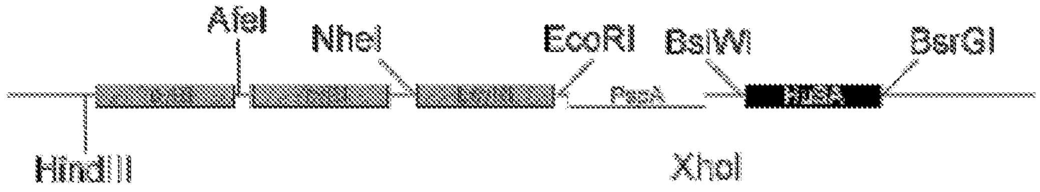

Fig. 19. Non-FcγRI-Targeted PspA-HuSA
Construct G
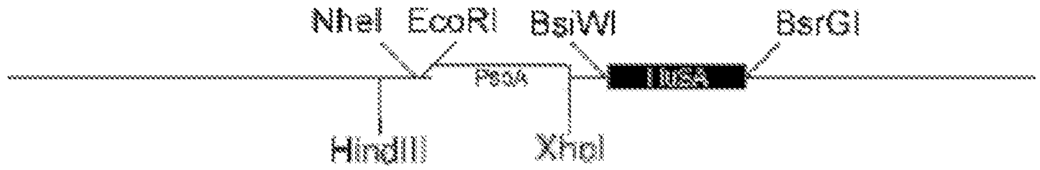

MULTI-FUNCTIONAL MUCOSAL VACCINE PLATFORM

CROSS REFERENCE TO RELATED APPLICATIONS

This application claims priority to U.S. Provisional Application No. 61/938,607, filed Feb. 11, 2014, the entire content of which are hereby incorporated by reference.

STATEMENT OF FEDERALLY SPONSORED RESEARCH AND DEVELOPMENT

This invention was made with government support under Grant No. 5R01 AI076408-04 awarded by the National Institute of Health. The government has certain rights in the invention.

INCORPORATION-BY-REFERENCE OF MATERIAL SUBMITTED ELECTRONICALLY

Incorporated by reference in its entirety herein is a computer-readable sequence listing submitted concurrently herewith and identified as follows: One 114,302 Byte ASCII (Text) file named "seq_listing.txt," created on Feb. 11, 2015.

BACKGROUND

The majority of human pathogens enter via mucosal sites. Thus, there is a significant need for novel vaccine technologies that can generate robust mucosal immunity. However, adjuvants are currently required to accomplish this. Yet, adjuvants applied to mucosal tissue increase the risk of unwanted inflammatory effects, toxicity, and may even increase susceptibility to infection.

U.S. Publication No. 20120258092 to Dahiyat relates to optimized CD20 antibodies having Fc variants, methods for their generation, and method for their application, such as methods of enhancing macrophage activation, particularly for therapeutic purposes.

U.S. Patent Application Publication No. 2009/0280181 to Slager relates to particles with nucleic acid complexes, medical devices including the same and related methods.

U.S. Pat. No. 7,459,531 to Moore relates to human secreted proteins and isolated nucleic acids containing the coding regions of the genes encoding such proteins. Also provided are vectors, host cells, antibodies, and recombinant methods for producing human secreted proteins.

U.S. Pat. No. 6,248,332 to Gosselin relates to methods of stimulating in a subject an immune response to an Ag to which the immune response is targeted. This method includes the step of administering to the subject a binding agent, which binds a surface receptor of an APC, and an Ag to which the immune response is targeted.

U.S. Pat. No. 6,258,358 to Gosselin relates to methods of stimulating in a subject an immune response to an Ag to which the immune response is targeted. Also disclosed are molecular complexes including the binding agent coupled to an Ag.

U.S. Pat. No. 7,316,812 to Keler relates to cells transformed to express on their surface a component, which binds to an Fc receptor of an effector cell are disclosed. Also disclosed are expression vectors used to transform the cells. Once transformed, the cells bind to effector cells via the Fc receptor of the effector cell to stimulate an effector cell mediated immune response.

U.S. Pat. No. 7,378,504 relates to isolated monoclonal Abs, such as human Abs that bind to CD64 with high affinity. Nucleic acid molecules encoding the Abs of the invention, expression vectors, host cells and methods for expressing the Abs of the invention are also disclosed.

U.S. Publication No. 20040109874 to Fuller relates to methods for generating an immune response at a mucosal surface.

However, none of the aforementioned documents appear to disclose or suggest using a fusion protein with binding domains FcγRI+FcRn as an adjuvant-free muscosal vaccine.

This background information is provided for informational purposes only. No admission is necessarily intended, nor should it be construed, that any of the preceding information constitutes prior art against the present invention.

SUMMARY

In one aspect, the vaccine platform will allow non-invasive, single dose, and highly efficient vaccine delivery to the nasal mucosa, thereby stimulating robust mucosal immunity in the absence of traditional adjuvant. This vaccine platform will have wide application not only against common pathogens such as *Streptococcus pneumonia* and influenza, but also emerging, re-emerging, and biodefense pathogens.

One embodiment involves the development of a unique multi-functional non-adjuvanted mucosal vaccine platform that will maximize mucosal and systemic immune responses (cellular and humoral), eliminate the need for adjuvant, eliminate the requirement for a cold chain, enable safe intranasal delivery of vaccines, as well as provide a vaccine platform that can be employed to develop vaccines against a wide range of pathogens and in particular, superior protection against pathogens that infect via the mucosal route. To accomplish these goals, this vaccine will comprise a DNA and/or recombinant fusion protein (FP) vaccine. In the case of the DNA form, in some embodiments, the DNA will be administered intranasally as a single dose and induce expression of an Fc receptor (FcR)-targeted FP. Alternative approaches will include: an FcR-targeted DNA prime-FP boost vaccine, a combined FcR-targeted DNA plus FP vaccine, or an FcR-targeted FP prime-FP boost vaccine. In some embodiments, the vaccine will be administered intranasally as either a liquid mist or powder lyophilized or precipitated onto carrier particles. When administered as a DNA vaccine, in some embodiments, the plasmid encoding the FP will transfect mucosal epithelial cells along the nasal mucosa within the upper respiratory tract, resulting in local expression of FcR-targeted FP containing the antigen (Ag). In some embodiments, the FP itself will comprise three functional components/elements (be multi-functional in nature) (FIG. 1). The first component will be the Ag/immunogen. The Ag will be fused to a neonatal FcR (FcRn)-targeting element. FcRn can mediate the transport of IgG and serum albumin from the lumen of the mucosal tract to the underlying nasal associated lymphoid tissue (NALT). In one embodiment, the FcRn-targeting element will therefore function in providing direct transport of the Ag-containing FP to the NALT. Within the NALT are Ag presenting cells (APCs), which are key to generating an effective mucosal and peripheral immune response to intranasally administered immunogens/Ags. To increase targeting of the immunogen to APCs, the Ag within the FP will also fused to a humanized human FcγRI-specific multi-valent scFv (APC)-targeting element. FcγRI is primarily expressed on two key APCs: macrophages and dendritic cells (DCs), which are involved in initiation and maintenance of the adaptive immune response. Thus, fusing the Ag to an FcγRI targeting element will target the Ag directly to the APCs for enhanced DC maturation, Ag processing, Ag presentation, and Ag-specific T cell activation, following transport of the FP to the NALT via FcRn. Flexible linkers can be attached to either side of the Ag in an effort to minimize steric interference between FP components (Ag and targeting elements). The ability of the vaccine to both mediate Ag transport to the NALT and subsequently target APCs within the NALT, is a unique feature of this vaccine that will maximize its potency and eliminate the need for an adjuvant. In summary, this FP vaccine, which could be administered as either a DNA or protein form and in a regimen consisting of DNA alone, protein alone, or a combination of the two consisting of either a consecutive DNA prime followed by a protein boost (DNA+protein) or DNA and protein at the same time (DNA/protein) will initiate a unique sequence of events (FIG. 1): 1) In the case of the DNA, DNA+protein, or DNA/protein, the vaccine will result in transfection of epithelial cells lining the nasal mucosal and the production and secretion of Ag-containing FP by these cells. 2) In the case of both DNA and protein forms, immunization will result in enhanced transport of the FP via FcRn to the NALT and targeting of Ag-containing FPs to APCs within the NALT via FcγRI. Consequently, the presence of the Ag-containing FP in the nasal mucosal tissue will induce both humoral and cellular immunity at mucosal and parenteral sites. The use of the protein form of FP will not depend on successful transfection of the epithelial cells. On the other hand, successful transfection of nasal epithelial cells with the FP in a DNA vaccine form will provide a number of advantages including rapid and inexpensive production and, since DNA vaccines are stable at room temperature, elimination of the requirement for a cold chain and stockpiling of the vaccine. Similarly, use of FP in protein vaccine form either alone or in combination with a DNA vaccine should minimize the need for a cold chain, since refrigeration is generally required to maintain stability of protein-adjuvant formulations and the FP vaccine does not require an adjuvant. In all instances, toxicities and adverse events associated with nasal vaccines containing live viral vectors or adjuvants would be significantly reduced or eliminated.

This strategy can be employed for any pathogen and is therefore a vaccine platform technology. The vaccine platform will provide a particular advantage over existing vaccines in protection against pathogens that are transmitted via the respiratory route (i.e. influenza, RSV, *tuberculosis, Streptococus pneumoiae*, etc.). In addition, since intranasal immunization results in the induction of mucosal responses in other compartments (i.e vagina, gut) and in the blood, the technology could also be used to develop vaccines against sexually transmitted pathogens (i.e. HIV, *Chlamydia*, etc.), orally transmitted pathogens (i.e. Hepatitis A, *Helicobacter pylori*) and blood-borne pathogens (i.e. vector borne pathogens, such as dengue and pathogens transmitted via needle sticks, such as HBV). As indicated above, the vaccine is designed to maximize Ag transport to the NALT and subsequently Ag presentation/T cell activation within the NALT, resulting in an efficient mechanism to induce both local mucosal as well as systemic humoral and cellular immunity. This technology will solve several challenges that currently cannot be met by existing technologies: 1) Most vaccines are administered systemically (injected with a needle) and induce immune responses primarily in the periphery providing a defense against a respiratory pathogen only after it has disseminated from the periphery into the mucosa. In contrast, the proposed FP vaccine will induce superior protection against pathogens transmitted via a mucosal route by inducing immune responses that block or abort transmission at the site of mucosal exposure. 2) Existing licensed or experimental vaccines require either a live attenuated virus or adjuvant to stimulate protective levels of immunity, but at the expense of inducing inflammatory responses that reduce their tolerability and safety, especially when administered intranasally. In contrast, in one embodiment, the FP vaccine does not require an adjuvant, so it can be safely administered intranasally and induce mucosal immunity with minimal risk. 3) Most DNA vaccines are poorly immunogenic due, in part, to lack of inherent immunostimulatory properties and the low amount of Ag produced. Current efforts to overcome the poor immunogenicity of DNA vaccines include delivery of multiple doses, co-administration of the DNA vaccine with an adjuvant, and/or boosting DNA vaccine primed responses with a different vaccine modality. In contrast, in one embodiment, the FP vaccine in a DNA form will overcome these issues by directly targeting the small amounts of Ag-containing FP produced by the DNA vaccine to the NALT and APCs within the NALT. In this way, the expressed Ag is more efficiently processed and presented to the immune systemic leading to more robust immunogenicity without the need for high Ag doses or a second vaccine modality. In addition, targeting Ag to the APCs results in activation of these cells without the need for an adjuvant. 4) Using the FP vaccine in either DNA or protein form and administered as either DNA or protein alone or in combination (DNA+protein, DNA/protein) will provide advantages over similar vaccine concepts administered as non-targeted recombinant protein, killed, or live attenuated vaccines. Specifically, DNA vaccines are stable at room temperature so they can be distributed without a cold chain. In addition, DNA vaccines can be rapidly scaled up with relatively minimal cost providing a more cost effective approach for wide-spread vaccination. Due to the lack of requirement for adjuvant, the protein form of the FP vaccine should provide similar advantages, Furthermore, in the event of an emerging pandemic, a FP vaccine will be able to achieve more rapid intervention than other vaccine modalities because production of the vaccine will require only the pathogen's sequence from a clinical isolate and once identified, FP vaccines can be propagated in a very short (FP as DNA) or shorter (FP as protein) period of time using well-established molecular and recombinant techniques, without the need for extensive or complex purification steps. Since both the DNA and protein forms of the FP vaccines are non-replicating, they are also safer and can be more rapidly manufactured and distributed without the need for the more extensive safety tests currently required for killed or live attenuated vaccines. In addition, the FP vaccine should be more immunogenic with fewer doses, reducing the need for repeat immunizations, further increasing patient compliance and safety profile of the vaccine.

This will be the first instance of a mucosal vaccine employing FP as either a DNA or protein vaccine form, which targets both FcRn and FcγRI. More generally, to our knowledge, expression/use of FP vaccine designed to both target Ag to the NALT via the FcRn transepithelial transport pathway, and subsequently to APCs within the NALT via FcγRI, has not been tested or published. Furthermore, DNA vaccination is not an obvious choice for this approach because, in the absence of FcR targeting, DNA vaccines are poorly immunogenic and require high doses to induce an immune response that cannot be achieved via intranasal delivery. In fact, most DNA vaccines are administered via the intramuscular route and designed to express and present the Ag primarily in the muscle cells not nasal cells in vivo. Therefore, a DNA vaccine, which produces a FP that targets the Ag to APC in a mucosal compartment, is not obvious and is novel. Furthermore, the expression of the FP by a DNA vaccine, which targets enhanced delivery of the Ag (via FcRn-targeted FP) to the NALT, and subsequently APCs within the NALT will likely overcome poor immunogenicity of DNA vaccines, thus providing a novel method to overcome current limits of DNA vaccines. Based on current state of art, people would also not combine the three FP components (Anti-FcγRI-Ag-anti-FcRn) into a single FP. However, we have thus far demonstrated we can generate an FP that maintains FcRn and FcγRI targeting functions. Furthermore, an FP DNA vaccine will provide two concurrent mechanisms for Ag presentation—first, in the cells transfected and adjacent interdigitating DCs, and second, in the APCs within the NALT targeted by the expressed Ag-containing FP. This dual Ag presentation will not only increase immunogenicity, but should also expose a broader range of antigenic epitopes than a traditional recombinant protein or DNA vaccine, resulting in a broader specificity in the immune response that will be more effective for protection. DNA vaccine transfection of nasal epithelium in vivo will also provide an advantage over nasal delivery of killed or live attenuated vaccines because presentation in these vaccine forms is very transient, whereas a DNA vaccine can express Ag in the transfected cells for days or weeks, thus providing longer term exposure in vivo to the vaccine Ag and targeting of the Ag to APCs within the NALT. This effect should translate into more durable immunity when compared to mucosal administration of non-targeted protein-based vaccines. Taken together, the vaccine strategy will result in a unique sequence of events (FIG. 1) that have not yet been demonstrated as possible or replicated by current traditional approaches for vaccination.

In some embodiments the mucosal vaccine platform can be broadly employed for any pathogen, especially those transmitted via the respiratory route. Gene delivery in the case of CF or drug delivery are also contemplated.

Some embodiments inhere advantages, for example: 1) Improve potency of DNA vaccines; 2) Eliminates the cold chain; 3) Non-invasive administration; 4) Eliminates adjuvant/potential toxicity; 5) Reduced dose, administrations, and thus cost and potential for adverse effects; 6) No adjuvant and no live replicating vectors so increased safety profile (minimal risk for inflammation, no risk of reversion); 7) Can generate both humoral and cellular immunity; 8) Can generate both mucosal and peripheral immunity; 9) Mucosal immunity induced by the vaccine is expected to confer enhanced protection against mucosally transmitted pathogens when compared to existing vaccines that induce responses only in the periphery; 10) Universal vaccine platform that will be applicable to bacterial and viral as well as mucosal and non-mucosal pathogens; 11) Likely increased compliance due to elimination of booster immunizations and injection with needle.

It is to be understood that both the foregoing summary and the following descriptions are exemplary, and thus do not restrict the scope of the embodiments.

BRIEF DESCRIPTION OF THE DRAWINGS

FIG. 1 graphically presents predicted trafficking of one embodiment of the hFcRn/hFcγRI-Targeted FP.

FIG. 2 presents data wherein anti-hFcγRI-PspA FP enhances protection against Sp challenge in hFcγRI Tg mice, in the absence of adjuvant. C57BL/6 hFcγRI Tg mice (5-8 mice/group) were immunized i.n. with PBS or 25 ng of anti-hFcγRI-PspA FP (day 0) and boosted on days 14 and 28. Two weeks post-final boost, mice were challenged i.n. with Sp ($1\times10^6$ CFU), and survival was monitored for 21 days. Representative survival curves from a minimum of 3 experiments are presented. $p<0.005$ (PBS vs. anti-hFcγRI-PspA FP-immunized group).

FIG. 3 presents data wherein targeting PspA to hFcγRI enhances Sp-specific Ab responses in hFcγRI Tg mice. C57BL/6 WT and hFcγRI Tg mice (4-6/group) were immunized i.n. with PBS or with 25 μg of bivalent anti-hFcγRI-PspA (day 0) and boosted on days 14 and 28. On day 42 serum and BAL were collected, and the Sp-specific IgG (A) and IgA (B) were measured by ELISA, respectively. Results are representative of 2 independent experiments (*, $P<0.1$; **, $P<0.05$).

FIG. 4 graphically presents a status of some embodiments of FP and DNA Vaccine Constructs.

FIG. 5 presents data wherein trivalent anti-hFcγRI-PspA binds hFcγRI and bivalent anti-hFcγRI-PspA-HSA binds hFcγRI and hFcRn: Supernatants from FP transfected NSO cells were screened for FP binding to hFcRn and/or hFcγRI by ELISA. To hFcγRI-coated wells (A), media or NSO supernatant from non-transfected and FP transfected cells were added overnight at 4° C. followed by 3 washes, addition of Rb anti-PspA or Rb anti-HSA Ab for 2 hrs at 4° C., 3 washes, goat anti-Rb IgG-AP for 2 hrs at 4° C., 3 washes, and AP substrate at room temperature. To hFcRn coated wells (B), supernatants were added and the above process repeated using Rb anti-PspA Ab only. In this case, all reagents, including supernatants, were adjusted to pH 6.0 (required for FcRn binding). ODs from media controls were subtracted from sample ODs. FP concentrations were not equalized for these assays, potentially explaining signal variability between FP samples. *$P<0.05$, ***$p<0.0001$.

FIG. 7 presents data wherein DNA for PspA and bivalent anti-hFcγRI-PspA FP was inserted into pJV7563 (3.759 kb) to produce pJV7563-pspa (4.665 kb) and pJV7563-anti-hFcγRI-pspa (6.333 kb). The plasmid DNA was linearized by digestion with NheI before agarose gel electrophoresis.

FIG. 8 presents data wherein secretion of soluble PspA (sPspA) and soluble anti-hFcγRI-PspA FP (sAnti-hFcγRI-PspA) by cells transfected with DNA vaccine vectors. NIH-3T3 (Mouse-embryonic fibroblast) cells were transfected with DNA lipofectamine complexes. After 72 h incubation, supernatants were harvested. Total proteins in supernatants were separated by SDS-polyacrylamide gel electrophoresis and transferred to nitrocellulose membranes. The membranes were then incubated sequentially with PspA specific Ab and then AP-conjugated secondary Ab. The nitrocellulose membranes were then developed with 5-bromo-4-chloro-3-indolyl-phosphate-nitrobluetetrazolium substrate. Empty vector (Vector) and purified recombinant PspA (rPspA) were used as negative and positive controls, respectively. Molecular weight markers are also depicted (M).

FIG. 9 presents data wherein generation of Sp-specific IgG following i.n. immunization with PspA versus anti-hFcγRI-PspA FP DNA vaccine using hFcγRI Tg versus WT mice. Human FcγRI Tg or WT mice were immunized with empty vector, vector containing PspA DNA, or vector containing anti-hFcγRI-PspA FP DNA. Each DNA vaccine was mixed with PolyEthyleneImine (PEI) and 5% Glucose, and kept for 15 mm at room temperature for DNA-PEI complex formation prior to administration. Mice 6-8 weeks of age were then immunized by i.n. route on days 0 and 28. Specifically, mice were anesthetized and 40 μl of PEI-DNA complex containing 4.2 pmole DNA was administered drop-wise into alternating nostrils. Sera were collected 14 days post-boost. In this preliminary study, data represents the mean of 3 mice/group±SE. Additional studies will now be conducted with 8 mice per group.

FIG. 10 presents data wherein one embodiment of mAb 22.2 from which the anti-hFcγRI-PspA FP was generated, also cross-reacts with NHP FcγRI. Anti-hFcγRI mAbs 22.2 (red) and 10.1, recognize and bind to FcγRI on NHP PBMCs. Isoptype controls are blue.

FIG. 11 presents data wherein trivalent and HSA-containing FPs bind hFcγRI on hFcγRI-expressing U937 cells: Supernatants from FP construct-transfected NSO cells were screened by flow cytometry for the presence of FPs and the ability of trimeric and HSA-containing/FcRn-binding FPs to bind hFcγRI on U937 cells. Briefly, hFcγRI-expressing U937 cells were incubated for 2 hrs at 4° C. with culture medium, supernatant from non-transfected NSO cells, or supernatant from FP transfected cells in the presence of human IgG (to block non-specific FcR binding of Rb Abs), followed by 3 washes, a 1 h incubation with Rb anti-PspA or Rb anti-HSA Ab, 3 washes, and a 30 min incubation with goat anti-Rb IgG-FITC. Cells were then washed, fixed, and analyzed by flow cytometry. P<0.005, *p<0.0001.

FIG. 12 graphically presents one embodiment of a map of pJG582 Vector. The pJG582 vector contains four tandem 5' to 3' DNA sequences encoding humanized VL-VH-VL-VH ScFv fragments derived from the humanized 22 (anti-human FcγRI) monoclonal antibody. These segments are joined by flexible linker sequences and flanked on the 5' end by a CMV promoter, which induces FP production by eukaryotic cells. 3' of the above V segments are XhoI/NotI restriction sites between which DNA sequences encoding antigen, such as PspA, or other molecules, can be inserted. 3' of the XhoI/NotI insertion site is a neo resistance gene used for selection of transfected cells expressing the desired FP. In addition, within this vector is a signal sequence, which directs secretion of the FP by eukaryotic cells producing it.

FIG. 14 graphically presents one embodiment of a map of pJV-7563 Vector (No secretion signal). Note: The sequences for PspA or the anti-human FcγRI-PspA fusion proteins have been inserted between NheI and Bgl-II restriction sites.

FIG. 15 graphically presents one embodiment of a map of pUW-160s Vector (Contains secretion signal). This Plasmid has a Lysozyme secretion signal (Labeled as Lysozyme SP), which facilitates secretion of attached polypeptides through plasma membranes. Note: While making vaccine constructs the stuffer fragment has been replaced with either PspA or anti-human FcγRI-PspA fusion protein.

FIG. 16 graphically presents embodiments of constructs in trivalent Anti-FcγRI-PspA.

FIG. 17 graphically presents embodiments of constructs in bivalent Anti-FcγRI-PspA-HuSA.

FIG. 18 graphically presents embodiments of constructs in trivalent Anti-FcγRI-PspA-HuSA.

FIG. 19 graphically presents embodiments of constructs in non-FcγRI-Targeted PspA-HuSA.

DETAILED DESCRIPTION OF THE SEVERAL EMBODIMENTS

Figure 6:
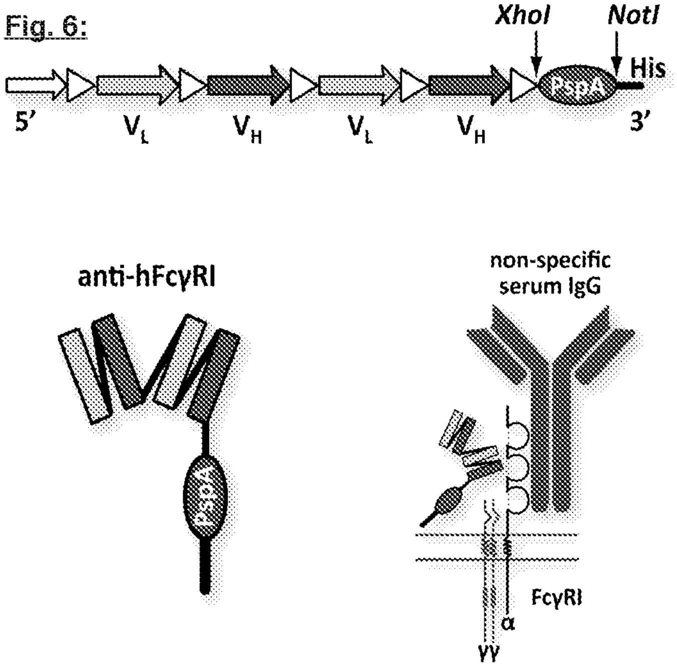
FIG. 6 graphically presents one embodiment of anti-hFcγRI-Ag FPs lacking the Fc domain, with the Fab regions also binding outside the IgG-Fc binding site FIG. 6*a* graphically presents some embodiments of current and proposed FP formulations.
Figure 13:
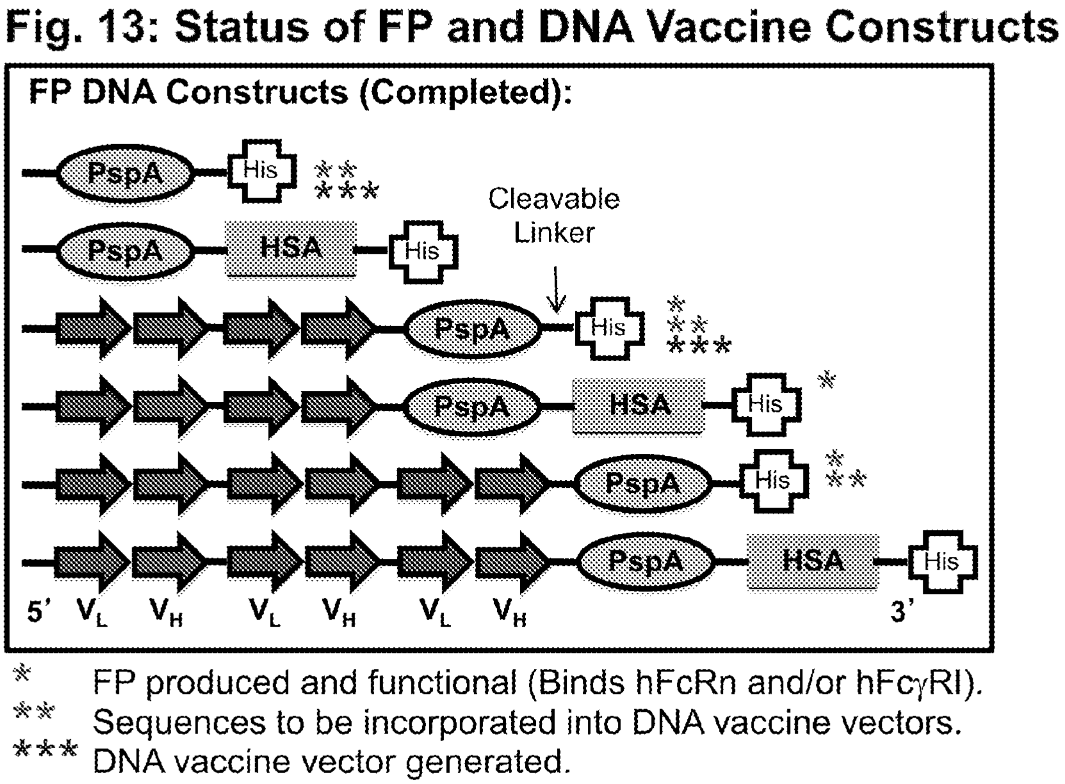
FIG. 13 graphically presents some embodiments of status of FP and DNA Vaccine Constructs.

Reference will now be made in detail to several embodiments which, together with the drawings and the examples herein, serve to better describe the invention in sufficient detail to enable those skilled in the art to practice the invention, and it is understood that other embodiments may be utilized, and that structural, biological, and chemical changes may be made without departing from the spirit and scope of the present invention. Unless defined otherwise, all technical and scientific terms used herein have the same meanings as commonly understood by one of ordinary skill in the art.

One skilled in the art may refer to general reference texts for detailed descriptions of known techniques discussed herein or equivalent techniques. These texts include *Current Protocols in Molecular Biology* (Ausubel et. al., eds. John Wiley & Sons, N.Y. and supplements thereto), *Current Protocols in Immunology* (Coligan et al., eds., John Wiley St Sons, N.Y. and supplements thereto), *Current Protocols in Pharmacology* (Enna et al., eds. John Wiley & Sons, N.Y. and supplements thereto) and *Remington: The Science and Practice of Pharmacy* (Lippincott Williams & Wilicins, 2Vt edition (2005), for example.

Definitions of common terms in molecular biology may be found, for example, in Benjamin Lewin, *Genes VII*, published by Oxford University Press, 2000 (ISBN 019879276X); Kendrew et al. (eds.); *The Encyclopedia of Molecular Biology*, published by Blackwell Publishers, 1994 (ISBN 0632021829); and Robert A. Meyers (ed.), *Molecular Biology and Biotechnology: a Comprehensive Desk Reference*, published by Wiley, John & Sons, Inc., 1995 (ISBN 0471186341).

For the purpose of interpreting this specification, the following definitions will apply and whenever appropriate, terms used in the singular will also include the plural and vice versa. In the event that any definition set forth below conflicts with the usage of that word in any other document, including any document incorporated herein by reference, the definition set forth below shall always control for purposes of interpreting this specification and its associated claims unless a contrary meaning is clearly intended (for example in the document where the term is originally used). The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps. Furthermore, where the description of one or more embodiments uses the term "comprising," those skilled in the art would understand that, in some specific instances, the embodiment or embodiments can be alternatively described using the language "consisting essentially of" and/or "consisting of." As used herein, the term "about" means at most plus or minus 10% of the numerical value of the number with which it is being used.

In some embodiments, a broadly applicable vaccine platform is provided.

In some embodiments, the need for an adjuvant is eliminated. In some embodiments, an adjuvant is not present.

In some embodiments, vaccine safety is improved.

In some embodiments, the manufacture and approval of vaccines is improved or streamlined, or the costs thereof are reduced.

In some embodiments, an adjuvant-independent mucosal vaccine platform is provided, which includes a single recombinant molecule comprising one or more multiple interdependent components, or any combination of: 1) an antigen or antigen-binding component; 2) a component that targets the vaccine antigen to human FcRn; 3) a component that targets the vaccine antigen to human FcγRI; 4) a component that facilitates purification of the vaccine when in protein form. Linker sequences designed to minimize steric interference between adjacent components can connect the individual components. In some embodiments, the components act sequentially and in concert in order to maximize vaccine potency and thereby eliminate the requirement for adjuvant. In some embodiments, the antigen or antigen-binding component provides the immunogen that stimulates protective immunity. In some embodiments, the human FcRn-binding component functions to initially deliver the antigen from the nasal tract to the nasal-associated lymphoid tissue (NALT) via FcRn-containing nasal epithelial cells. In some embodiments, the human FcγRI-binding component will then direct the antigen to human FcγRI-expressing antigen presenting cells within the NALT. In some embodiments, both of the latter events are employed to sufficiently increase vaccine potency to a level that permits the elimination adjuvant. In some embodiments, the human FcRn-binding component will first maximize antigen delivery to the NALT, while the human FcγRI-binding component will subsequently maximize immune stimulation by antigen presenting cells within the NALT. In some embodiments, as a result of this sequence of events, the recombinant vaccine will generate immune protection equal or superior to that of vaccines containing adjuvant.

In some embodiments, the invention provides an immunogenic fusion protein for use as a mucosal vaccine comprising:

i) one or more FcγR1-binding domains;
ii) one or more antigens from one or more infectious disease organisms; and
iii) one or more FcRn-binding domains.

In some embodiments, the invention provides an immunogenic fusion protein for use as a cancer vaccine comprising:

i) one or more FcγR1-binding domains;
ii) one or more antigens from one or more cancers; and
iii) one or more FcRn-binding domains.

In some embodiments, the invention provides an immunogenic fusion protein for use as a mucosal vaccine comprising:

i) one or more FcγR1-binding domains;
ii) one or more antigen binding components that bind antigen from one or more infectious disease organisms; and
iii) one or more FcRn-binding domains.

In some embodiments, the invention provides nucleic acids and vectors encoding the immunogenic fusion proteins.

In some embodiments, the vectors can be useful as DNA vaccines. In one embodiment, the invention provides a vector comprising the nucleotide sequence of SEQ ID NO:17 (pUW160s). An antigen or gene of interest can be inserted into SEQ ID NO:17 immediately after nt position 2304. In one embodiment, the invention provides a vector comprising the nucleotide sequence of SEQ ID NO:18 (pJV7563). An antigen or gene of interest can be inserted into SEQ ID NO:18 immediately after nt position 1993.

In some embodiments, the invention provides pharmaceutical compositions comprising the immunogenic fusion proteins.

In some embodiments, the invention provides pharmaceutical compositions comprising the nucleic acids or vectors.

In some embodiments, the invention provides a method of inducing an immune response, comprising administering to a subject in need thereof an immunologically-effective amount of an immunogenic fusion protein of the invention.

In some embodiments, the invention provides a method of inducing an immune response, comprising administering to a subject in need thereof an immunologically-effective amount of a nucleic acid encoding an immunogenic fusion protein of the invention.

In some embodiments, the invention provides a method of inducing an immune response, comprising administering to a subject in need thereof an immunologically-effective amount of nucleic acid encoding any one of the following, or a combination thereof;

i) an immunogenic fusion protein comprising:
  a. one or more antigens from one or more infectious disease organisms; and
  b. one or more FcRn-binding domains;
ii) an immunogenic fusion protein comprising:
  a) one or more FcγR1-binding domains; and
  b) one or more antigens from one or more infectious disease organisms; and
iii) an immunogenic fusion protein comprising:
  a) one or more FcγR1-binding domains;
  b) one or more antigens from one or more infectious disease organisms; and
  c) one or more FcRn-binding domains.

In some embodiments, the invention provides a method of inducing an immune response, comprising administering to a subject in need thereof an immunologically-effective amount of a fusion protein of any one of the following, or a combination thereof;

i) an immunogenic fusion protein comprising:
  a) one or more antigens from one or more infectious disease organisms; and
  b) one or more FcRn-binding domains;
ii) an immunogenic fusion protein comprising:
  a) one or more FcγR1-binding domains; and
  b) one or more antigens from one or more infectious disease organisms; and
iii) an immunogenic fusion protein comprising:
  a) one or more FcγR1-binding domains;
  b) one or more antigens from one or more infectious disease organisms; and
  c) one or more FcRn-binding domains.

In some embodiments, the one or more FcγR1 binding domains is an anti-FcγR1 antibody or a fragment thereof. In some embodiments, the anti-FcγR1 antibody fragment comprises SEQ ID NO:24. In some embodiments, the FcγR1 is human.

In some embodiments, the one or more FcRn binding domains is selected from the group consisting of an anti-FcRn antibody or a fragment thereof and a mammalian serum albumin protein or a fragment thereof. In some embodiments, the FcRn binding domain is human serum albumin or a fragment thereof. In some embodiments, the FcRn binding domain is a fragment of human serum albumin comprising domain III. In some embodiments, the FcRn binding domain is a variant of domain III of human serum albumin having at least 90% amino acid identity. In some embodiments, the fragment of human serum albumin comprising domain III comprises SEQ ID NO: 25. In some embodiments, the FcRn is human.

In some embodiments, the infectious disease organism is a bacterial or viral pathogen. In some embodiments, the pathogen is selected from the group consisting of *Streptococcus pneumonia, Neisseria meningitidis, Haemophilus influenza, Klebsiella* spp., *Pseudomonas* spp., *Salmonella* spp., *Shigella* spp., and Group B streptococci, *Bacillus anthracis* adenoviruses; *Bordetella pertussus; Botulism; Bovine rhinotracheitis; Brucella* spp.; *Branhamella catarrhalis*; canine *hepatitis*; canine distemper; Chlamydiae; Cholera; coccidiomycosis; cowpox; tularemia; filoviruses; arenaviruses; bunyaviruses; cytomegalovirus; cytomegalovirus; Dengue fever; dengue toxoplasmosis; *Diphtheria; encephalitis; Enterotoxigenic Escherichia coli*; Epstein Barr virus; equine encephalitis; equine infectious anemia; equine influenza; equine pneumonia; equine rhinovirus; feline leukemia; flavivirus; *Burkholderia mallei*; Globulin; *Haemophilus influenza* type b; *Haemophilus influenzae; Haemophilus pertussis; Helicobacter pylori; Hemophilus* spp.; *hepatitis; hepatitis* A; *hepatitis* B; hepatitis C; herpes viruses; HIV; HIV-1 viruses; HIV-2 viruses; HTLV; Influenza; Japanese encephalitis; *Klebsiellae* spp. *Legionella pneumophila; leishmania*; leprosy; lyme disease; malaria immunogen; measles; meningitis; meningococcal; Meningococcal Polysaccharide Group A, Meningococcal Polysaccharide Group C; mumps; Mumps Virus; mycobacteria; *Mycobacterium tuberculosis; Neisseria* spp; *Neisseria gonorrhoeae*; ovine blue tongue; ovine encephalitis; papilloma; SARS and associated coronaviruses; parainfluenza; paramyxovirus; paramyxoviruses; Pertussis; Plague; *Coxiella burnetti; Pneumococcus* spp.; *Pneumocystis carinii*; Pneumonia; Poliovirus; *Proteus* species; *Pseudomonas aeruginosa*; rabies; respiratory syncytial virus; rotavirus; Rubella; Salmonellae; schistosomiasis; Shigellae; simian immunodeficiency virus; Smallpox; *Staphylococcus aureus; Staphylococcus* spp.; *Streptococcus pyogenes; Streptococcus* spp.; swine influenza; *tetanus; Treponema pallidum*; Typhoid; Vaccinia; *varicella-zoster* virus; and *Vibrio cholera* and combinations thereof.

The antigen from the pathogen is not limiting. In some embodiments, the antigen is selected from the group consisting of: PspA (*Streptococcus pneumonia*), gp120 (HIV), hemagglutinin (*influenza*) and neuraminidase (*influenza*). In some embodiments, the antigen is PspA. The nucleotide sequence of PspA is provided in SEQ ID NO:16.

The one or more antigen binding components that bind antigen from one or more infectious disease organisms is not limiting. In some embodiments, the one or more antigen binding components comprises C reactive protein (CRP) (HGNC: 2367) or a fragment thereof, C3 (HGNC: 1318) or a fragment thereof, myelin basic protein (MBP) (HGNC: 6925) or a fragment thereof, CD6 (HGNC: 1691) or a fragment thereof, CD163 (HGNC: 1631) or a fragment thereof, and combinations thereof.

The one or more antigens from one or more cancers is not limiting. In some embodiments, the one or more antigens from one or more cancers is selected from the group consisting of wherein the antigen is selected from the group consisting of *hepatitis* B surface antigen (HBsAg), *hepatitis* B core antigen (HBcAg), and *hepatitis* B e antigen (HBeAg), N53, NS4a, NS5a and NS5b, HPV E6/E7, EBV LMP, HBV, HCV, mutated k-ras, p53, bcr-abl, HER-2, hTERT, ganglioside GD3, NY-ESO-1, MAGE/BAGE/GAGE, Hu, Yo, GAD, MART-1/melan-A, gp-100, tyrosinase, PSA and combinations thereof.

The cancer to be treated is not limiting and can include acute lymphoblastic leukemia, acute myeloid leukemia, adrenocortical cancer, AIDS-related cancers, AIDS-related lymphoma, anal cancer, astrocytoma (including, for example, cerebellar and cerebral), basal cell carcinoma, bile duct cancer, bladder cancer, bone cancer, brain stem glioma, brain tumor (including, for example, ependymoma, medulloblastoma, supratentorial primitive neuroectodermal, visual pathway and hypothalamic glioma), cerebral astrocytoma/malignant glioma, breast cancer, bronchial adenomas/carcinoids, Burkitt's lymphoma, carcinoid tumor (including, for example, gastrointestinal), carcinoma of unknown primary site, central nervous system lymphoma, cervical cancer, chronic lymphocytic leukemia, chronic myelogenous leukemia, chronic myeloproliferative disorders, colon cancer, colorectal cancer, cutaneous T-Cell lymphoma, endometrial cancer, ependymoma, esophageal cancer, Ewing's Family of tumors, extrahepatic bile duct cancer, eye cancer (including, for example, intraocular melanoma, retinoblastoma, gallbladder cancer, gastric cancer, gastrointestinal carcinoid tumor, gastrointestinal stromal tumor (GIST), germ cell tumor (including, for example, extracranial, extragonadal, ovarian), gestational trophoblastic tumor, glioma, hairy cell leukemia, head and neck cancer, squamous cell head and neck cancer, hepatocellular cancer, Hodgkin's lymphoma, hypopharyngeal cancer, islet cell carcinoma (including, for example, endocrine pancreas), Kaposi's sarcoma, laryngeal cancer, leukemia, lip and oral cavity cancer, liver cancer, lung cancer (including, for example, non-small cell), lymphoma, macroglobulinemia, malignant fibrous histiocytoma of bone/osteosarcoma, medulloblastoma, melanoma, Merkel cell carcinoma, mesothelioma, metastatic squamous neck cancer with occult primary, mouth cancer, multiple endocrine neoplasia syndrome, multiple myeloma!plasma cell neoplasm, mycosis fungoides, myelodysplastic syndromes, myelodysplastic/myeloproliferative diseases, myeloma, nasal cavity and paranasal sinus cancer, nasopharyngeal cancer, neuroblastoma, non-Hodgkin's lymphoma, oral cancer, oral cavity cancer, osteosarcoma, oropharyngeal cancer, ovarian cancer (including, for example, ovarian epithelial cancer, germ cell tumor), ovarian low malignant potential tumor, pancreatic cancer, paranasal sinus and nasal cavity cancer, parathyroid cancer, penile cancer, pharyngeal cancer, pheochromocytoma, pineoblastoma and supratentorial primitive neuroectodermal tumors, pituitary tumor, plasma cell neoplasm/multiple myeloma, pleuropulmonary blastoma, pregnancy and breast cancer, primary central nervous system lymphoma, prostate cancer, rectal cancer, retinoblastoma, rhabdomyosarcoma, salivary gland cancer, soft tissue sarcoma, uterine sarcoma, Sézary syndrome, skin cancer (including, for example, nonmelanoma or melanoma), small intestine cancer, supratentorial primitive neuroectodermal tumors, T-Cell lymphoma, testicular cancer, throat cancer, thymoma, thymoma and thymic carcinoma, thyroid cancer, transitional cell cancer of the renal pelvis and ureter, trophoblastic tumor (including, for example, gestational), unusual cancers of childhood and adulthood, urethral cancer, endometrial uterine cancer, uterine sarcoma, vaginal cancer, viral induced cancers (including, for example, HPV induced cancer), vulvar cancer, Waldenström's macroglobulinemia, and Wilms' Tumor.

In some embodiments, the immunogenic fusion protein enhances transepithelial transport of the fusion protein to the nasal-associated lymphoid tissue (NALT) and enhances FcγR1 crosslinking by the fusion protein on antigen presenting cells (APC) within the NALT.

In some embodiments, the fusion protein comprises two or more FcγR1 binding domains. In some embodiments, the fusion protein comprises three FcγR1 binding domains.

In some embodiments, the immunogenic fusion protein comprises bivalent Anti-FcγRI-PspA-HuSA. In some embodiments, the bivalent Anti-FcγRI-PspA-HuSA comprises the amino acid sequence of SEQ ID NO:12. In some embodiments, the bivalent Anti-FcγRI-PspA-HuSA comprises the nucleotide sequence of SEQ ID NO:23.

In some embodiments, the immunogenic fusion protein comprises trivalent Anti-FcγRI-PspA-HuSA. In some embodiments, the trivalent Anti-FcgRI-PspA-HuSA comprises SEQ ID NO:13. In some embodiments, the trivalent Anti-FcγRI-PspA-HuSA comprises the nucleotide sequence of SEQ ID NO:20.

In some embodiments, the immunogenic fusion protein comprises a cleavable protein sequence and/or affinity tag to aid in purification. In some embodiments, the affinity tag comprises at least 6 histidine residues. In some embodiments, the immunogenic fusion protein comprises a secretion signal to facilitate secretion of the protein through plasma membrane. In some embodiments, the secretion signal is a lysozyme secretion signal.

In some embodiments, wherein upon administration to a subject, the fusion protein generates protection against both mucosal and non-mucosal pathogens. In some embodiments, the fusion protein generates protection at mucosal and non-mucosal sites.

In some embodiments, the vaccine platform includes a recombinant molecule containing single or multiple antigens from a single infectious disease organism.

In some embodiments, the vaccine platform includes a recombinant molecule containing single or multiple antigens from multiple infectious disease organisms.

In some embodiments, the one or more antigen binding components includes a component that binds to live attenuated infectious disease organisms.

In some embodiments, the one or more antigen binding components includes a component that binds to inactivated infectious disease organisms.

In some embodiments, the vaccine platform includes an antigen from cancerous or tumor cells.

In some embodiments, the vaccine platform includes a single or multiple human FcRn-binding domains.

In some embodiments, the vaccine platform includes a single or multiple human FcγRI-binding domains.

In some embodiments, the vaccine platform includes a cleavable protein purification component.

In some embodiments, the vaccine platform includes an additional immune modulatory component.

In some embodiments, the additional immune modulatory component is or includes a TLR agonist, Complement component, or cytokine analogue.

In some embodiments, the vaccine platform includes a DNA or RNA vaccine administered intradermally or intranasally.

In some embodiments, the vaccine platform includes a DNA or RNA vaccine, which lacks the FcRn-binding component when administered intradermally.

In some embodiments, the vaccine platform includes a immunogenic fusion protein which lacks the FcRn-binding component.

In some embodiments, trivalent Anti-FcγRI-PspA can be utilized in the invention, which lacks a FcRn-binding component. In some embodiments, the amino acid sequence of trivalent Anti-FcγRI-PspA is SEQ ID NO:11 and the nucleotide sequence is SEQ ID NO:19.

In some embodiments, bivalent Anti-FcγRI-PspA can be utilized in the invention, which lacks a FcRn-binding component. In some embodiments, the amino acid sequence of bivalent Anti-FcγRI-PspA is SEQ ID NO:12 and the nucleotide sequence is SEQ ID NO:21.

In some embodiments, the vaccine platform includes a DNA or RNA vaccine, which induces secretion of the recombinant protein vaccine into the nasal tract, when administered intranasally.

In some embodiments, the vaccine platform includes a protein vaccine administered intradermally or intranasally.

In some embodiments, the vaccine platform includes a protein vaccine, which lacks the FcRn-binding component, when administered intradermally. In some embodiments, Non-FcγRI targeted PspA-HuSA can be useful. In some embodiments, the amino acid sequence of PspA-HuSA is SEQ ID NO:14 and the nucleotide sequence is SEQ ID NO:22.

In some embodiments, the vaccine platform is administered as a DNA vaccine intradermally and subsequently a protein vaccine intranasally.

In some embodiments, the vaccine platform is administered as a protein vaccine intradermally and subsequently a DNA vaccine intranasally.

In some embodiments, the vaccine platform generates protection against both mucosal and non-mucosal pathogens.

In some embodiments, the vaccine platform generates protection at mucosal and non-mucosal sites.

In some embodiments, the vaccine platform includes a single vaccine containing a population of recombinant vaccine molecules, each containing a different infectious disease antigen or a set of infectious disease antigens.

In some embodiments, the vaccine platform includes a single vaccine containing a population of recombinant molecules, each containing a different tumor antigen or a set of tumor antigens.

In some embodiments, the vaccine platform is humanized.

In some embodiments, the vaccine platform is modified to eliminate autoreactive and/or antigenic sequences unrelated to the infectious disease or tumor antigen(s).

In some embodiments, a fusion protein comprising *Streptococcus pneumonia* antigen PspA is provided. In some embodiments, a divalent anti-hFcγRI-PspA-HSA (human serum albumin fragment) FP is provided. In some embodiments, a trivalent anti-hFcγRI-PspA-HSA FP is provided.

In some embodiments, the divalent and trivalent anti-hFcγRI-PspA-HSA FP is functional in vivo based on FcR binding (hFcγRI, FcRn), enhanced FP internalization via hFcγRI, enhanced transepithelial transport of Ag via FcRn, and enhanced hFcγRI-mediated presentation of PspA to PspA-specific T cells.

In some embodiments, PspA, anti-hFcγRI-PspA, and anti-hFcγRI-PspA-HSA containing DNA vaccine vectors are provided.

In some embodiments, a formulation (bi- vs. trivalent FP; FcRn vs. non-FcRn-binding; DNA, FP, or DNA prime-FP boost), route (i.n., i.d., or i.m.), and dose, is provided based on *Streptococcus pneumonia* immunogenicity and protection.

In some embodiments, the *Streptococcus pneumonia* vaccine platform affords broad protection against 2 or more strains of *Streptococcus.*

In some embodiments, immunogenicity and protection is comparable or superior to the vaccines such as Prevnar®13.

In some embodiments, the flu HA FP induces broad protection against homologous and drifted strains of flu.

In some embodiments, immunogenicity and protection is comparable or superior to vaccines such as Fluzone.

The present invention further provides pharmaceutical compositions comprising the fusion proteins and nucleic acids in combination with a pharmaceutically acceptable excipient.

In one embodiment, pharmaceutically acceptable means a material that is compatible with the other ingredients of the composition without rendering the composition unsuitable for its intended purpose, and is suitable for use with subjects as provided herein without undue adverse side effects (such as toxicity, irritation, and allergic response). Side effects are "undue" when their risk outweighs the benefit provided by the composition. Non-limiting examples of pharmaceutically acceptable carriers or exipients include, without limitation, any of the standard pharmaceutical carriers or excipients such as phosphate buffered saline solutions, water, emulsions such as oil/water emulsions, microemulsions, and the like.

The fusion proteins and nucleic acids described herein can be prepared and/or formulated without undue experimentation for administration to a mammal, including humans, as appropriate for the particular application. The pharmaceutical compositions may be manufactured without undue experimentation in a manner that is itself known, e.g., by means of conventional mixing, dissolving, dragee-making, levitating, emulsifying, encapsulating, entrapping, spray-drying, or lyophilizing processes, or any combination thereof.

Suitable routes of administration may include, for example, oral, lingual, sublingual, rectal, transmucosal, nasal, buccal, intrabuccal, intravaginal, or intestinal administration; intravesicular; intraurethral; topical administration; transdermal administration; administration by inhalation; parenteral delivery, non-parenteral delivery, including intramuscular, subcutaneous, intramedullary injections, as well as intrathecal, direct intraventricular, intravenous, intraperitoneal, intranasal, or intraocular injections, and optionally in a depot or sustained release formulation. Furthermore, one may administer the compound in a targeted drug delivery system, for example in a liposome. Combinations of administrative routes are possible.

Proper dosages of the fusion proteins can be determined without undue experimentation using standard dose-response protocols. In one embodiment, the dosage of the compound, salt thereof, or a combination thereof, or pharmaceutical composition, may vary from about 0.001 μg/kg to about 1000 mg/kg. This includes all values and subranges therebetween, including 0.001, 0.002, 0.003, 0.004, 0.005, 0.006, 0.007, 0.008, 0.009, 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, and 1 μg/kg, 0.001, 0.002, 0.003, 0.004, 0.005, 0.006, 0.007, 0.008, 0.009, 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1 2, 3, 4, 5, 6, 7, 8, 9, 10, 11, 12, 13, 14, 15, 16, 17, 18, 19, 20, 21, 22, 23, 24, 25, 50, 75, 100, 200, 300, 400, 500, 600, 700, 800, 900, and 1000 mg/kg, and any combination thereof.

In one embodiment, the fusion proteins and/or nucleic acids are administered mucosally.

The fusion proteins and nucleic acids can also be prepared for nasal administration. As used herein, nasal administration includes administering the compound to the mucous membranes of the nasal passage or nasal cavity of the subject. Pharmaceutical compositions for nasal administration of the compound include therapeutically effective amounts of the compound prepared by well-known methods to be administered, for example, as a nasal spray, nasal drop, suspension, gel, ointment, cream or powder. Administration of the compound may also take place using a nasal tampon or nasal sponge.

The compositions may also suitably include one or more preservatives, anti-oxidants, or the like.

Some examples of techniques for the formulation and administration of the fusion proteins and nucleic acids may be found in *Remington: The Science and Practice of Pharmacy*, Lippincott Williams & Wilkins Publishing Co., 20 addition, incorporated herein by reference.

In one embodiment, the pharmaceutical compositions contain the fusion protein or nucleic acid in an effective amount to achieve their intended purpose. In one embodiment, an effective amount means an amount sufficient to prevent or treat the disease. In one embodiment, to treat means to reduce the development of, inhibit the progression of, or ameliorate the symptoms of a disease in the subject being treated. In one embodiment, to prevent means to administer prophylactically, e.g., in the case wherein in the opinion of the attending physician the subject's background, heredity, environment, occupational history, or the like, give rise to an expectation or increased probability that that subject is at risk of having the disease, even though at the time of diagnosis or administration that subject either does not yet have the disease or is asymptomatic of the disease.

While the invention has been described with reference to certain particular examples and embodiments herein, those skilled in the art will appreciate that various examples and embodiments can be combined for the purpose of complying with all relevant patent laws (e.g., methods described in specific examples can be used to describe particular aspects of the invention and its operation even though such are not explicitly set forth in reference thereto).

Other embodiments of the invention are discussed throughout this application. Any embodiment discussed with respect to one aspect applies to other aspects as well and vice versa. Each embodiment described herein is understood to be embodiments that are applicable to all aspects of the invention. It is contemplated that any embodiment discussed herein can be implemented with respect to any device, method, or composition, and vice versa. Furthermore, systems, compositions, and kits of the invention can be used to achieve methods of the invention.

Aspects of the present teachings may be further understood in light of the following examples, which should not be construed as limiting the scope of the present teachings in any way.

EXAMPLES

A highly potent mucosal vaccine platform, which does not require adjuvant, can be generated utilizing a human FcγRI (hFcγRI)-specific-antigen (Ag) fusion protein (FP), which: 1) Incorporates a human FcRn (hFcRn)-binding sequence to increase transepithelial transport of FP to the nasal-associated lymphoid tissue (NALT). 2) Has increased valency in its hFcγRI-targeting component to further enhance Ag internalization, Ag processing, dendritic cell (DC) maturation, and Ag presentation in the NALT. 3) Combines an i.n. hFcR-targeted DNA vaccine-prime with an i.n. FP-boost to maximize and sustain vaccine potency.

The mucosa is the first line of defense against many pulmonary bacterial and viral pathogens and their antigenic variants. Also, mucosal immunity, induced by natural infection or vaccination, can afford better protection than peripheral immune responses, including improved cross-protection against antigenic variants[1-4]. Without wishing to be bound by theory, it is believed that this is likely due, in part, to a crucial early opportunity to prevent a disseminated infection by eliminating/blocking the infection at its most vulnerable stage, while the infection is still limited. However, most licensed vaccines induce responses primarily in the periphery, producing a suboptimal immune response at the initial mucosal site of exposure. In addition, the most commonly used vaccine platforms—live attenuated and adjuvanted protein vaccines—often cause adverse inflammatory effects when administered via a mucosal route. Unadjuvanted protein vaccines are safer, but usually poorly immunogenic. Thus, we propose the development of a novel and highly potent mucosal FP vaccine platform, which does not require the use of adjuvant. The FP will: 1) Target Ag to hFcRn to increase Ag transepithelial transport to the NALT[5]. 2) Increase hFcγRI crosslinking on APCs within the NALT to enhance Ag presentation and T cell activation[6-10]. 3) Combine an i.n. administered hFcR-targeted DNA vaccine-prime with an i.n. FP-boost. A strategy that has been shown to enhance the magnitude, quality, and longevity of protein vaccines[11]. Data, which support the successful development of the proposed adjuvant-independent mucosal vaccine platform include the use of a hFcγRI transgenic mouse model in which pneumococcal surface protein A (PspA) targeted to hFcγRI i.n. generates enhanced mucosal immunity and protection against a mucosal challenge with *Streptococcus pneumoniae* (Sp), without the use of adjuvant[7]. We have also shown that a mAb-bound inactivated *Francisella tularensis* (mAb-iFt) complex administered i.n. enhances protection against mucosal Ft challenge. This protection is FcγR-dependent and requires FcRn[8]. Subsequent studies have also demonstrated that FcRn mediates enhanced transport of mAb-iFt versus iFt alone from the nasal passage to the NALT[9]. Thus, a strong potential for the successful development of the proposed adjuvant-free mucosal vaccine platform has been demonstrated using two distinct FcR-targeted vaccine strategies and two distinct mucosal infectious disease models in which enhanced protection has been observed without the use of traditional adjuvant. A novel/unique FP will now be generated/developed to maximize adjuvant-free FP potency, which will be crucial to its successful application, as well as altering long established perceptions regarding the requirement for adjuvant. Specifically, we will incorporate molecular modifications to our bivalent prototype FP to further improve FP targeting and immunogenicity: 1) A sequence, which targets FPs to hFcRn[12,13], will be added to increase FP delivery to the NALT. 2) The divalent anti-hFcγRI-PspA FP will be converted to a trivalent hFcγRI-targeted FP to further enhance Ag internalization, Ag processing, DC maturation, and subsequent Ag presentation[9,10,14,15] within the NALT. 3) An i.n. administered hFcR-targeted DNA vaccine-prime will be combined with an i.n. FP-boost to further improve vaccine potency and durability[16-20].

Aim 1: Produce and verify in vitro, the functional capacity of bivalent, trivalent, and hFcRn-targeted anti-hFcγRI-PspA FPs. The bivalent, trivalent, and hFcRn-targeted anti-hFcγRI-PspA FPs have been produced. FP functions tested will include: hFcRn binding and transepithelial transport of FPs, FP binding to hFcγRI, FP internalization by APCs, and the ability of FPs to induce DC maturation and FP-enhanced Ag presentation/T cell activation.

Aim 2: Identify the optimal (most protective) FP configuration utilizing a hFcγRI/hFcRn-expressing mouse model. Bivalent versus trivalent hFcRI-targeted FPs (plus or minus the hFcRn binding component) will be administered i.n. at varying FP doses. Protection against Sp challenge and PspA-specific T and B cell responses will be measured. The optimal FP will be identified based primarily on superior protection provided.

Aim 3: Maximize FP vaccine platform potency and protective longevity utilizing an i.n. administered hFcR-targeted DNA vaccine-prime plus i.n. FP-boost regimen. The ability of FP, hFcR-targeted DNA, and hFcR-targeted DNA vaccine-prime plus FP-boost regimens, each administered i.n., to further enhance protection and extend immune memory, without the use of adjuvant, will be tested. The optimal Sp vaccine regimen will then be compared to licensed Sp vaccine, followed by cross-protection studies to validate the cross-protective potential of this vaccine platform, in particular as it applies to Sp vaccination.

Current approaches to vaccine development are as diverse as the infectious organisms they are designed to protect against. However, most current protein-based vaccine strategies require two primary components: identification of a protective antigen (Ag) and the use of an appropriate adjuvant. Adjuvants can be divided into two primary categories: immune modulators and delivery systems[21]. Immune modulators include: bacterial products [lipopolysaccharides, peptidolglycans, lipoproteins, DNA (CpGs), and enterotoxins], plant products (saponins and glycosylceramides), and cell products (heat shock proteins and cytokines). Mechanisms of action include: dendritic cell (DC)/macrophage activation, up-regulation of costimulatory molecules (required for efficient T cell activation), and induction of cytokines involved in immune regulation. However, most immune modulators have broad specificity and activity, increasing potential toxic side effects and raising safety concerns. Vaccine delivery systems are more limited in number. Delivery systems function primarily by slowing Ag release at the site of injection and/or enhancing Ag uptake by Ag presenting cells (APCs). The only delivery system currently approved for human use in the U.S. is mineral salt, specifically Alum, which induces a potent antibody (Ab) (humoral, Th2-type) response, but is ineffective at boosting cellular (Th1-type or CD8 T cell) responses. Another delivery system consists of emulsions (Ag mixed with oil and water) such as MF59. However, similar to mineral salt (Alum), MF59 stimulates a potent humoral (Th2-type) immune response, but fails to stimulate cellular immune responses. A third delivery system consists of particulate Ag, such as the incorporation of Ag into lipid-containing vesicles or nanoparticles. Particulate Ag can stimulate both humoral and cellular immune responses. However, manufacture and maintenance of particle consistency can be difficult and expensive, potentially resulting in a vaccine product, which 3$^{rd}$ world countries cannot afford. In addition, the adjuvants discussed above are generally used in parenteral immunizations, which often do not produce strong mucosal immunity[22]. Yet, the majority of pathogens enter via mucosal routes. In contrast, mucosal immunization can provide potent protection at both mucosal and non-mucosal sites[5]. Furthermore, as specifically pointed out in a number of reviews, including in Nature Medicine and Nature Reviews, this applies to human vaccination, as well as that of mice[23-25]. Thus, there is a need for more effective and safe mucosal vaccination strategies and/or mucosal adjuvants. While both Cholera Toxin B (CTB) and IL-12 can be effective as mucosal adjuvants in mice[26-28], and possibly humans, as with many adjuvants, there is significant concern regarding their toxicity/safety. Therefore, a mucosal vaccine platform, which does not require adjuvant and can stimulate both humoral and cellular immune responses, such as the use of FcR-targeted mucosal immunogens [anti-FcR fusion proteins (FPs)][5,29], would significantly advance vaccine technology, while eliminating many of the issues associated with the use of adjuvants. As stated by Dr. Jerry McGhee, a world renown mucosal immunologist, "The development of effective strategies for mucosal vaccination would revolutionize medicine"[5]. In addition, targeting Ag to hFcγRI bypasses the inhibitory receptor FcγRIIB, which can limit FcγR-induced DC maturation and Ab production[14,15]. Accordingly, we propose the development of a highly innovative adjuvant-independent (recombinant) mucosal vaccine platform, which sequentially targets FP Ag to: 1) hFcRn for enhanced transepithelial transport of Ag to the nasal-associated lymphoid tissue (NALT), and 2) hFcγRI on APCs/DCs for enhanced Ag processing/presentation and T cell/B cell activation within the NALT (FIG. 1). In addition, we will combine a hFcR-targeted DNA vaccine-prime with an i.n. FP-boost to further optimize vaccine potency and durability[16-20].

The current paradigm for vaccine development involves the identification of a protective Ag and the requirement for a safe and effective adjuvant. Given the myriad of problems adjuvants face, including safety concerns and FDA approval, and the paucity of researchers challenging this paradigm by developing adjuvant-free vaccine strategies, the proposed adjuvant-free FP platform is a highly innovative approach to mucosal vaccine development. Furthermore, the creation of a unique/novel dual (hFcγRI/hFcRn)-targeted multi-functional FP, which mediates sequential targeting of FP Ag to hFcRn i.n. for enhanced transepithelial transport of FP Ag to the NALT and subsequently FP Ag to hFcγRI on APCs for enhanced T and B cell activation within the NALT (FIG. 1), is also highly innovative. Lastly, these will represent the first studies that seek to combine a hFcR-targeted DNA vaccine and hFcR-targeted mucosal FP vaccine in a DNA-prime FP-boost regimen.

Regarding the potential for developing an adjuvant-free mucosal vaccine, published studies and preliminary data validate the potential for success of the proposed FP-based mucosal vaccine platform. Specifically, partial protection against the highly virulent *F. tularensis* (Ft) SchuS4 organism is achieved when immunizing i.n. with adjuvant-free inactivated Ft (iFt) targeted to FcR via mAb-iFt complex[8]. Furthermore, these studies demonstrate important roles for FcγR and FcRn in this protection. Specifically, mice immunized i.n. with mAb-iFt are not protected in the absence of FcγR or FcRn[8]. Also, subsequent mechanistic studies indicate that FcRn plays a critical role in enhancing the transport of iFt to the NALT, when immunizing i.n. with mAb-iFt[2]. Importantly, the enhanced transport of iFt to the NALT is eliminated in the absence of FcRn. In addition, subsequent studies by other laboratories have demonstrated a similar function for FcRn, when utilizing i.n. administered recombinant Fc-Ag immunogens plus adjuvant[30,31]. In 2012, one of the present inventors also published studies utilizing a hFcγRI transgenic (Tg) mouse model and a prototype bivalent [mono (hFcγRI)-specific] anti-hFcγRI-PspA FP. These studies demonstrated that administering this prototype anti-hFcγRI-PspA FP i.n. to hFcγRI Tg mice in the absence of adjuvant enhances protection against subsequent *S. pneumoniae* (Sp) challenge (FIG. 2)[7]. Importantly, the enhanced protection observed requires both the presence of hFcγRI in vivo and PspA targeted to hFcγRI in the form of anti-hFcγRI-PspA FP[7]. Sp-specific IgA and IgG responses (FIG. 3), Ab-dependent complement deposition on Sp, and lactoferrin-mediated killing of Sp, are also enhanced[7]. The above enhancement is not observed in non-hFcγRI Tg [wildtype (WT)] mice[7]. Furthermore, while FcRn targeting is not required in the case of bivalent anti-hFcγRI-PspA FP, possibly due to M cell-mediated transport of FP, an FP that sequentially targets Ag to FcRn for transepithelial transport of FP to the NALT, and subsequently to multiple hFcγRIs for enhanced hFcγRI crosslinking on APCs/DCs within the NALT (FIG. 1), is very likely to significantly improve the potency, and thus efficacy, of the adjuvant-independent hFcR-targeted FP vaccine platform.

The FP DNA constructs to be used in these studies, which have been generated, are depicted in FIG. 4. The trivalent anti-hFcγRI-PspA and divalent anti-hFcγRI-PspA-HSA FPs have also been produced and bind hFcγRI and hFcγRI/hFcRn, respectively (FIG. 5). Thus, the ability to generate functional divalent and trivalent FPs, as well as FPs that bind both hFcRn and hFcγRI, is demonstrated (FIG. 5). Furthermore, in Aim 3, we also provide preliminary studies demonstrating the efficacy of i.n. DNA vaccination with hFcγRI-targeted immunogen.

Development of vaccine platform technology such as that proposed, which eliminates the requirement for adjuvant, will fundamentally alter the paradigm by which vaccines are generated and administered. In addition, as stated by Dr. McGhee[5] "The development of effective strategies for mucosal vaccination would revolutionize medicine, allowing protection from the many viral and bacterial pathogens that enter the body via the mucosa . . . "[5,30,31]. Specifically, the proposed FP platform will be the first recombinant unadjuvanted mucosal vaccine platform to take full advantage of this "Mucosal Gateway" for vaccination (FIG. 1) by facilitating the sequential transepithelial transport of FP Ag from the nasal passage to the NALT (via FcRn), and subsequently targeting FP Ag to hFcγRI on APCs within the NALT, while maximizing hFcγRI crosslinking on APCs in the NALT. Furthermore, development of this FP mucosal vaccine platform technology will fundamentally transform the generation and administration of vaccines against a wide array of infectious agents including: emerging, re-emerging, and biodefense pathogens, as well as non-mucosal pathogens. Finally, development of a vaccine platform that does not require adjuvant will significantly reduce safety concerns and concerns related to the limited capacity of many adjuvants to stimulate both humoral and cellular immunity.

Aim 1: Produce and verify in vitro, the functional capacity of bivalent, trivalent, and FcRn-targeted anti-hFcγRI-PspA FPs.

Published studies by one of the inventors demonstrate that a prototype bivalent anti-hFcγRI-PspA FP administered i.n. to hFcγRI Tg mice, enhances protection against subsequent i.n. challenge with Sp in the absence of adjuvant[7]. Others, when targeting Ag to FcRn i.n., but with adjuvant, have obtained similar results[30,31]. Evidence suggests that the above FcRn-mediated enhancement is due, in part, to increased transport of Ag from the nasal passage to the underlying NALT[5,31]. Thus, to further optimize the potency of our current prototype divalent anti-hFcγRI-PspA FP, a sequence from human serum albumin (HSA-Domain III), which binds FcRn and mediates FcRn-dependent transepithelial transport of Ags[13], has been added to the divalent anti-hFcγRI-PspA FP. We have also converted the bivalent FP to a trivalent FP to more extensively crosslink hFcγRI on APCs, thereby enhancing Ag internalization, DC maturation[9,10,14,15], Ag presentation/T cell activation, and ultimately vaccine potency. In regard to the use of a bivalent versus trivalent FP, it has been clearly demonstrated that anti-hFcγRI-targeted Ags are significantly more potent immunogens in trivalent vs. divalent form[6,10]. Furthermore, maximizing FP potency will be crucial to establishing a new paradigm in which the use of this adjuvant-free mucosal vaccine platform is a viable and an acceptable alternative to adjuvant.

Objectives: 1) Generate DNA constructs and produce FPs; 2) Verify FP function(s) in vitro.

Aim 1.1: Generation of DNA constructs and production of FPs.

FP DNA constructs depicted in FIG. 4, including control PspA and PspA-HSA constructs, have been generated. Functional bivalent and trivalent anti-hFcγRI-PspA and bivalent anti-hFcγRI-PspA-HSA FPs have also been produced (FIG. 5). Clones representing good producers of each construct will be expanded into a FiberCell system for producing concentrated FP supernatant and FPs will be purified by Nickel column. The successful isolation/purification of FPs will be verified by Western blot analysis and ELISA, as previously described.

Aim 1.2: Verification of FP function in vitro.

FP binding to hFcγRI and hFcRn: Binding of hFcγRI-specific FPs to hFcγRI and HSA-containing FPs to hFcRn will be measured by ELISA (FIG. 5) and confirmed via flow cytometry, using hFcγRI or hFcRn-expressing cells/DCs, as previously described[7]. However, in the case of ELISAs measuring FP binding to FcRn, wells will be coated with soluble hFcRn and the ELISA carried out at the appropriate pH (6.0), which is required for FcRn to bind HSA (FIG. 5B). Analogous FPs lacking HSA will serve as negative controls in the latter case (FIGS. 4 and 5B). To monitor hFcγRI and/or FcRn binding by flow cytometry, bone marrow-derived DCs (BMDCs) from hFcRn and/or hFcγRI-expressing mice will be used. BMDCs will be obtained as previously described by Dr. Gosselin[7]. In the case of hFcγRI binding, incubations and washes will be carried out at 4° C. FP binding will be detected by incubation with Rb anti-PspA or Rb anti-HSA Ab followed by three washes and subsequent addition of FITC labeled goat anti-Rb IgG. Cells will then be fixed and analyzed by flow cytometry. FcRn binding of FPs to DCs will be carried out similar to that of hFcγRI, but in a manner that detects intracellular binding, as previously published by others[32]. BMDCs from non-hFcγRI/FcRn-expressing mice will serve as negative controls.

Transepithelial transport of HSA-containing (FcRn-targeted) FPs: Modification of a standard in vitro IgG transport assay[33] will be used to assess HSA-containing FPs versus FPs lacking HSA to interact with FcRn from human epithelial cells and subsequently transit an epithelial layer. Briefly, T84 cells expressing human FcRn will be grown on transwell filter inserts to form a monolayer exhibiting transepithelial electrical resistance (300 ohms/cm2) as measured via a tissue-resistance meter equipped with planar electrodes. In addition to electrical resistance, confocal microscopy, immunohistochemistry, and bulk protein transport, will also be used to verify monolayer integrity[32,34]. Monolayers will be equilibrated in Hanks balanced salt solution. FPs will be applied to the apical compartment, and incubated with DMEM medium plus or minus competitor for FcRn (Free HSA) at varying concentrations for 1-4 hours at 37° C. Time point samples taken from the basolateral compartment will then be assayed for FPs via Western blot or ELISA. IgG will also be used as a positive control for FcRn-mediated transepithelial transport. Once, transepithelial transport has been verified using T84 cells, similar assays will be conducted using tracheal epithelial cells from WT, hFcRn Tg, hFcγRI Tg, and hFcγRI/hFcRn Tg mice.

Induction of DC maturation by FPs: Bivalent and trivalent FPs will be incubated with BMDCs and DC maturation measured by monitoring maturation markers (MHC Class II, CD40, CD80, CD86, and CD205) by flow cytometry, as previously described[9].

FP-mediated PspA presentation to PspA-specific T cells: This assay will also be conducted as previously described[7]. Briefly, the PspA-specific T cell hybridoma (B6D2) ($1\times10^5$ cells/well) will be co-cultured with hFcγRI/FcRn-expressing, non-hFcRn-expressing, and/or non-hFcγRI-expressing BMDCs ($2\times10^5$ cells/well) with titrating amounts of PspA or PspA-containing FPs. Equivalent PspA concentrations will be used as the basis for equilibrating FP concentrations and thereby comparing presentation of the various FPs, with concentrations ranging from 0 to 10 μg/ml of PspA. Cells will then be incubated for 30 hours at 37° C. in 5% $CO_2$, supernatants will be collected, and IL-2 production will be measured via Luminex assay. In addition to BMDCs from non-hFcγRI/FcRn-expressing mice, wells lacking BMDCs or FP Ag will also serve as negative controls, as well as wells containing soluble $F(ab')_2$ anti-hFcRn and/or anti-hFcγRI blocking mAbs, to further confirm hFcγRI and/or FcRn involvement.

Potential outcomes and alternative approaches: Bivalent and trivalent FPs, as well as anti-FcγRI-PspA-HSA FP have been produced and bind both hFcRn and/or hFcγRI (FIG. 5). Also, as indicated in FIG. 5 and a recent publication[7], the present inventors have extensive experience producing FcR-targeted FPs. Problems could however occur with the trivalent anti-hFcγRI-PspA-HSA FP. Trivalent FP binding to hFcγRI could be reduced compared to bivalent FP, possibly due to the presence of the trivalent component itself and/or the HSA component. However, this would not necessarily mean diminished vaccine function. Specifically, it is believed that the trivalent FP is more likely to form more stable (higher avidity) bonds with hFcγRI and engage more hFcγRI molecules per FP than bivalent FP, producing a lower signal by ELISA and flow cytometry. Yet, these same changes could also result in an FP, which more extensively cross-links hFcγRI on APCs[6,10], thereby inducing enhanced DC maturation, PspA internalization, and PspA presentation/T cell activation. Thus, judgment of trivalent FP function will be based on results of hFcγRI-binding and Ag presentation assays. If the trivalent FP still underperforms versus bivalent FP, linkers can be lengthened, in one embodiment, separating $V_L$-$V_H$ segments to reduce interdomain interference, thereby potentially increasing flexibility of the hFcγRI-binding domains. In another embodiment, the divalent FP may be combined with the FcRn-targeting component (HSA), and subsequently, a DNA-prime protein-boost regimen (Aim 3). One possible issue, in regard to in vivo use of FcRn-binding FPs, is the presence of low levels of serum albumin in the nasal tract. The latter could compete with the HSA-containing FPs for binding to FcRn. Indeed, due to the fact the albumin levels are relatively low in the nasal tract, albumin is often used to measure epithelial integrity[35,36]. Thus, while it is not believed that this will be a serious problem due in particular to the low albumin levels [<6 μg/ml in nasal lavage[36]], we will titrate in free HSA in the presence of FPs in the in vitro ELISA binding and epithelial transport assays to determine what levels of free serum albumin fully compete with FP binding to FcRn. Should the level be equal to or less than that normally found in the nasal tract, we will first verify this inhibition in vivo, then consider the use of alternative FcRn binding components such as Fc sequences to replace HSA. Should it ultimately not be possible to overcome this issue, one option is to focus on the divalent and/or trivalent FP lacking the FcRn-binding component and combining the bivalent and/or trivalent hFcγRI-targeted FP with a DNA-prime protein-boost regimen (Aim 3) to further enhance FP vaccine efficacy.

Aim 2: Optimize FP platform immunogenicity and protective efficacy utilizing the FPs generated and tested in Aim 1 and a hFcγRI/hFcRn-expressing mouse model.

It will be critical to first identify the FP generated in Aim 1, which is most protective against Sp challenge. Thus, we will compare the protective capacity of bivalent vs. trivalent FPs (plus and minus FcRn-binding HSA) using a hFcγRI/FcRn-expressing mouse model. Once the optimal (most protective) FP formulation is identified, the optimal dose will be determined, and humoral and cellular immune responses to FP vaccination will also be examined. While mucosal and parenteral immunization routes have proven successful in the case of Sp vaccines, mucosal routes are generally believed to be superior for mucosal pathogens in mouse and humans[23-25]. Thus, we will focus on the i.n. immunization route.

Objectives: 1) Utilizing a hFcγRI/FcRn-expressing mouse model, identify the FP formulation providing optimal protection against Sp challenge; 2) Using the above optimal FP formulation, identify the optimal FP dose that provides maximal protection in this challenge model; 3) Examine humoral and cellular immune responses to the FP vaccine.

Aim 2.1: Determine which FP provides optimal protection against Sp challenge utilizing a hFcγRI/FcRn-expressing mouse Sp protection model.

We currently maintain a colony of hFcγRI Tg and non-Tg littermate mice by breeding one male C57BL/6 hFcγRI Tg+/− mouse with two female C57BL/6 WT mice per breeding colony. The hFcγRI Tg mice are then identified by PCR. To generate hFcγRI/FcRn-expressing mice, we will similarly breed a male hFcγRI Tg+/− mouse with two C57BL/6 hFcRn (+/+) mice (Jackson Laboratories). Mice expressing both hFcγRI and hFcRn will again be identified by PCR, as is done to verify the presence of hFcγRI. Mice will be divided into groups of 8 mice/group, 8-12 weeks of age. Human FcγRI/FcRn-expressing mice will be immunized i.n. with 20 μl of PBS, PspA, PspA-HSA, bivalent anti-hFcγRI-PspA, bivalent anti-hFcγRI-PspA-HSA, trivalent anti-hFcγRI-PspA, or trivalent anti-hFcγRI-PspA-HSA on day 0 and boosted on day 21. In each case, the amount of PspA administered will be equivalent (10 μg/mouse). Immunized mice will then be challenged i.n. two weeks post-boost with $1\times10^6$ CFU Sp and monitored 21 days for survival. Infectious challenge of animals will be performed with strain A66.1[7], a mouse virulent capsule type 3 pneumococcus (family 1, clades 1,2), serologically similar to the family 1, clade 2, PspA of strain Rx1[37] utilized to construct the PspA-containing FPs. Culturing and counting the inoculums subsequent to challenge will be done to verify the exact CFU administered. Importantly, the above immunization regimen and challenge dose produces approximately 50% protection in hFcγRI Tg mice when immunizing with bivalent anti-hFcγRI-PspA[7]. The latter dosing/result will thus allow detection of differences in survival (positive and negative) between immunized groups. Should 100% protection be achieved with multiple FPs, the challenge dose will be increased to better distinguish between degrees of protective efficacy between FPs. To further delineate the protective efficacy of the FPs following immunization and challenge, bacterial burden will also be measured at various time intervals post-challenge in lung, liver, and spleen, as previously described by Dr. Gosselin[7]. The remaining tissue homogenate will be spun at 14,000×g for 20 min, and the clarified supernatant will be stored at −20° C. for future cytokine analysis.

Aim 2.2: Using the optimal FP formulation from Aim 2.1, determine the optimal FP dose that provides optimal protection in this challenge model.

Challenge experiments will be repeated utilizing the optimal FP formulation identified above and doses of PspA within FPs ranging from 3-30 μg/mouse. The challenge dose will be the highest dose used in Aim 2.1 for which protection was observed in Aim 2.1. Both survival and bacterial burden will then be measured. Once the optimal dose has been determined, immunizations will be carried out in WT, hFcRn Tg, hFcγRI Tg, versus hFcγRI/hFcRn-expressing mice to verify hFcRn and hFcγRI roles in the protection observed.

Aim 2.3: Examine the humoral and cellular immune responses to the FP vaccination.

Ab production: Sp-specific Ab production will be measured by ELISA as previously described by Dr. Gosselin[7]. Wells will be coated with live Sp or PspA. BSA-coated wells will be used as specificity controls for Sp and PspA. PspA and Sp-specific IgM, IgG isotypes, and IgA will be measured and responses compared between that of bronchioalveolar lavage (BAL) and serum from the same animals. We will also test for Abs cross-reactive with mouse and human tissues (potentially autoreactive Abs). In the case of human tissues, this will be done using paraffin embedded tissues from heart, lung, liver, kidney, and lymph node obtained commercially from anonymous donors. Tissues will be stained immunohistochemically as previously described by Dr. Gosselin[38] using serum from FP-immunized mice. Isotype controls and Abs with known tissue specificity will be used as negative and positive controls, respectively. The ability of sera from FP-immunized mice to block FP binding to hFcγRI or FcRn will also be examined.

Cytokine production: ELISPOT will be used following immunization to identify T cell subsets producing specific cytokines using previously published methods[39]. Cytokine production will also be measured after immunization, in vitro, as previously described by Dr. Gosselin[7,8]. Levels of selected cytokines produced in spleen cell supernatants in response to Ag (IL-2, IL-4, TNF-α, IFN-γ, and IL-5) will be measured using the multiplex Luminex assay. Cytokine mRNA generated following immunization will also be measured by RT-PCR at 1, 2, and 3 days post primary and booster immunization.

Histological analysis: It is possible that crosslinking hFcγRI could induce local toxicity or negative side effects, such as inflammation or local depletion of CD64+ cells. Therefore, histological and immunohistochemical analysis of infected tissues will be conducted to monitor and identify immune cell infiltrates and potential tissue damage/toxicity due to the immunogen/FP itself, as well as tissue damage due to infection. Mice will be euthanized at 12, 24, 48, 72, and 92 hours post-immunization or post-challenge. Post-immunization, lungs and nasal tract, including NALT, will be harvested. Post-challenge, lungs, spleen, lymph nodes (cervical, mediastinal, mesenteric, and submandibular), and nasal tract, including NALT, will be harvested. Tissues will be fixed in 2% paraformaldehyde in PBS. Tissues will then be processed for histology as previously described by one of the inventors[8,40].

Potential outcomes and alternative approaches: Should there be any issues with the hFcRn component of the hFcγRI/hFcRn Tg mouse, we have the option of substituting the human FcRn-targeting sequence with the mouse equivalent, and using our hFcγRI Tg mouse model. In addition, hFcRn targeting of the anti-hFcγRI-PspA-HSA FP can be verified independently in the hFcRn Tg mice. In regard to the trivalent anti-hFcγRI-PspA, two separate studies using anti-hFcγRI mAb (22 mAb), from which our FP construct was derived, indicate trivalent interaction of this molecule with hFcγRI will produce a more effective immunogen[6,10]m. However, should the trivalent FP not produce protection superior to bivalent FP, we will focus on further testing/optimizing the bivalent anti-hFcγRI-HSA FP approach and subsequently combining it with an FcR-targeted DNA-prime FP-boost regimen (Aim 3). In regard to FcRn binding of the anti-hFcγRI-PspA-HSA FP, studies in WT mice and preliminary data herein (FIG. 5) indicate that HSA does bind to FcRn in FP form[43]. However, the ability of FP Ag (PspA) to induce protective immunity may be compromised by conformational changes induced by the adjacent HSA component. In this case, the linker between PspA and HSA will be lengthened and/or alternative Ags, such as the highly cross-protective 100 amino acid proline-rich domain (PRD) of PspA[44] will be tested. However, should protection studies using HSA-containing FPs not be superior to anti-hFcγRI-PspA FPs, we will focus on further development of the bivalent or trivalent anti-hFcγRI-PspA FP and subsequently combining it with an FcR-targeted DNA-prime FP-boost regimen, to further maximize vaccine potency (Aim 3). In regard to potential FP toxicity, it is expected that the optimized adjuvant-free FP vaccine regimen will induce comparable or superior mucosal Ab, T cell, and protective responses that are also less inflammatory than Prevnar®13, leading to improved protection and a more favorable safety profile. Should this not be the case, utilizing an anti-hFcγRI-PspA DNA vaccine we have recently generated (See Aim 3), we will attempt to overcome this caveat via a DNA-prime FP-boost regimen, based on the observation that DNA priming enhances the magnitude, quality, and longevity of protein vaccines[11]. Alternatively, given the significant advantages of having an adjuvant-free mucosal vaccine platform[23-25] and the enhanced PspA/Sp-specific Ab production in response to FP, which we have observed using our prototype bivalent anti-hFcγRI-PspA[7], it is possible to continue to develop, optimize, and test this approach in mice, in particular for those pathogens where protection is primarily Ab-mediated. In the latter case, it will be possible to rapidly move to a non-human primate (NHP) model, since the anti-hFcγRI component of the FP does bind to NHP FcγRI (See "Future Development Plans"). Additional potential caveats include: failure of DCs to mature in response to FPs, which could result in tolerance induction[45-48], but could potentially be countered via increased hFcγRI crosslinking (Trivalent FP) or via a DNA-prime FP-boost regimen. It is also possible Abs will be generated to the FP itself, which then interfere with its function, or that cross-react with tissue Ags. In regard to anti-FP Abs, the inventors have already proven that the humanized anti-hFcγRI-PspA FP enhances immunity and protection in mice, despite the potential production of anti-FP Abs[7]. Importantly, this becomes less of an issue when studies move to NHPs and humans. Furthermore, EpiVax bioinformatics technology can be used to identify and remove epitopes responsible for the generation of FP blocking or autoreactive Abs (See attached Epivax letter)[49]. It is also possible that despite the lack of an adjuvant, inflammation and tissue damage will occur post-FP immunization. This could be overcome by reduced FP dosage and increasing the number of boosts, or the use of a DNA-prime FP-boost in combination with lower FP doses. The latter may well facilitate FP dose reduction in any case, without compromising protection.

It is also possible that crosslinking hFcγRI could induce local toxicity or negative side effects, such as inflammation or local depletion of CD64+ cells. For example, studies demonstrating hFcγRI modulation as a consequence of extensive cross-linking mediated by whole mAb H22 (humanized anti-hFcγRI), and subsequent inhibition of opsinophagocytosis has been observed, which thereby impairs normal immune function[50]. However, the observed inhibition in this case appeared to be dependent on the ability of whole 22 mAb to bind to hFcγRI via both Fab and Fc binding domains[50]. In contrast, our anti-hFcγRI-Ag FPs lack the Fc domain, with the Fab regions also binding outside the IgG-Fc binding site (FIG. 6), the latter being a key advantage of utilizing our particular FP construct. Thus, it is unlikely our FPs will similarly impair opsinophagocytosis. Furthermore, it is difficult to induce internalization of all hFcγRI on a given cell, since there is continuous replacement of cell surface receptors, and effective blocking of opsinophagocytosis in vivo would require continuous administration of large amounts of FPs, something that is not required to induce an effective immune response when targeting Ag to hFcγRI[7,51]. Furthermore, assuming depletion of CD64+ cells does occur, it is likely to be transient, and data indicates the initial interaction with FP is sufficient to generate protective immunity[7]. Excessive inflammation will be dealt with by varying immunogen doses and vaccination regimens. Examples of the current and present technology is depicted in FIG. 6*a*. The current technology already has several specific characteristics/advantages in terms of an object of the present application. It contains a humanized targeting component (H22) that is bivalent and binds to hFcγRI outside the ligand-binding domain for IgG (FIG. 6*a*, top panels). The latter is a critical characteristic, since hFcγRI is a high affinity FcγR and is normally occupied by hIgG (FIG. 6*a*, top right panel). The bivalent nature of the targeting component also allows for cross-linking of hFcγRI in order to facilitate internalization and processing by APCs. The Ag PspA is linked to the targeting component. PspA is a protective surface protein Ag derived from Sp. It is conserved across the majority of Sp strains providing the potential for FP-mediated cross-strain protection. Importantly, we have already demonstrated that in this FP configuration, the PspA maintains its ability (structurally) to induce protective immune responses in mice. The current FP also contains a removable His tag for purification purposes.

Aim 3: Optimize FP platform immunogenicity and protective efficacy/longevity utilizing a DNA-prime FP-boost strategy.

DNA vaccines are a lower cost alternative to protein vaccines, can be more easily distributed, and stimulate humoral and cellular parenteral and mucosal immune responses[52,53]. DNA vaccine studies utilizing PspA as a protective immunogen have also been successfully conducted in a mouse model.[54] Finally, a DNA-prime Protein-boost regimen has been shown to increase vaccine potency (humoral and cellular immune responses), as well as vaccine durability.[16-20]. Thus, we will utilize the latter strategy to determine if we can further increase the potency and efficacy/longevity of our mucosal FP vaccine. A significant advantage of utilizing PspA as the immunogen is its potential to cross-protect against multiple Sp strains[55-57]. Therefore, additional challenge studies utilizing the optimized FP platform will also be conducted to determine the ability of FcR-targeted FP to cross-protect against Sp infection with several different Sp strains. While one object of the present application is establishing a highly potent adjuvant-free mucosal vaccine platform applicable to many pathogens, the latter studies will ultimately be important to also initially establishing this vaccine platform as a potentially viable approach for Sp vaccination.

Objectives: 1) Generate and test PspA and anti-hFcγRI-PspA FP-producing DNA vaccine vectors; 2) Identify the optimal human FcγRI-targeted DNA and DNA-prime FP-boost regimens; 3) Determine the breadth of protective immunity against multiple Sp challenge strains and compare the optimized FP vaccine to a licensed conjugate vaccine (Prevnar®13).

Aim 3.1: Generation and testing of PspA and anti-hFcγRI-PspA FP-producing DNA vaccine vectors.

PspA and anti-hFcγRI-PspA genes have been inserted into an optimized DNA vaccine expression cassette (FIG. 7) which has been optimized for clinical trials as described[58,59]. Thus, to facilitate comparison of DNA i.n. versus i.d. immunization routes, both i.n. and i.d. DNA immunization studies will initially be conducted using the bivalent anti-hFcγRI-PspA FP lacking the FcRn targeting component. Furthermore, if the trivalent FP proves more efficacious in Aim 2, the trivalent anti-hFcγRI-PspA gene lacking HSA will also be inserted and tested as a DNA vaccine. The function of the DNA vectors containing PspA and anti-hFcγRI-PspA have also been verified in vitro. Specifically, production of PspA bivalent anti-hFcγRI-PspA FP by mouse 3T3 cells following transient transfection with DNA vaccine vectors has been demonstrated by Western blot (FIG. 8).

Aim 3.2: Identify optimal DNA and DNA-prime FP-boost regimens.

Immunogenicity and challenge experiments: Intradermal and i.n. DNA-prime i.n. FP-boost regimens will be compared to the optimized i.n. FP regimen identified in Aim 2. Importantly, we will initially focus on DNA immunization via the i.n. route. Subsequently we will use i.d. DNA immunization to determine if the i.d. route might be superior to the use of i n immunization either independently and/or in the DNA-prime FP-boost approach. Intradermal DNA immunization will also be used should i.n. DNA immunization prove less stimulatory than that of the i.d. route. Experimental groups will include WT, hFcRn Tg, hFcγRI Tg, and hFcγRI/FcRn-expressing mice. Controls will also include mice receiving empty vector and vector plus PspA. Vaccinations will consist of 2 doses, 4 weeks apart. Blood will be collected before and 2 and 4 weeks post-immunization to measure Sp-specific Ab. Four weeks post-final boost, mice will be sacrificed to collect BAL, splenocytes, and lung lymphocytes to measure mucosal Ab and T cell responses. Mucosal and systemic Ab, T cell responses, and protection from Sp challenge will be examined as described in Aim 2. The optimal regimen that induces a significant improvement in protection, when compared to controls and the optimal FP regimen identified in Aim 2, will then be compared to Prevnar®13. DNA immunizations will be done as described below.

Intranasal DNA vaccination: We will use an established method for i.n. immunization with plasmid DNA Our successful use of this immunization strategy to enhance PspA (Sp)-specific Ab responses with our hFcγRI-targeted FP is demonstrated in FIG. 9. Briefly, DNA will be introduced into the nasal passages of mice in the form of Polyethyleneimine (PEI)-DNA complexes. PEI and DNA will be mixed in 5% glucose. The DNA will be used at a range of 0.5-5 mg/ml in the PEI-DNA mixture. The PEI will be mixed with the DNA to achieve N [Nitrogen residues in PEEP (Phosphate residues in DNA)] ratio of 6-8. The PEI-DNA mixture will then be kept at room temperature for 10 minutes to allow the complex to form, after which it will be used for immunization. Mice will be anesthetized and the PEI-DNA mixture will then be administered drop wise in alternating nostrils using a micropipette. We will initially use DNA doses ranging from 4 to 12 pmole per construct to optimize DNA dosing.

Gene gun DNA immunizations: This procedure has also been used successfully in our laboratory. Gene gun, or particle-mediated epidermal delivery (PMED) of vaccines, is a common method used for transcutaneous injection (TCI) of DNA vaccines into the epidermal layer of the skin. It differs from IM or ID DNA injection in that it results in direct intracellular delivery of the DNA into non-professional APCs (i.e. keratinocytes) and professional APC (i.e. Langerhans cells) in the epidermis[62,63]. A major benefit of immunizing the skin is the induction of both systemic and mucosal responses[64-72] including highly disseminated mucosal IgA responses[73,74]. TCI in mice and NHPs has generated CD8 CTL[66,75,76] and mucosal IgA/Ab-secreting cells in the intestine[77-80] female reproductive tract[73,81], upper[71,76] and lower respiratory tract[82] and in the oral cavity[71,81,83]. In humans, TCI induced vaccine-specific IgA in saliva[84] and the intestine[85,86]. The mechanism by which TCI induces mucosal responses is not entirely clear. Studies in mice suggest two possible mechanisms: 1) APCs migrate from the skin to mucosal inductive sites and activate local T cells[64,66,68,70,87] and/or 2) APCs migrate to regional draining lymph nodes and induce a mucosal homing phenotype on activated lymphocytes, which then home to mucosal effector sites[88,89]. PMED is one of the most efficient methods for DNA vaccine delivery and has induced protective levels of systemic Ab and CD8 T cell responses against a wide variety of diseases in mice, NHP and humans[78,90-92]. Importantly, like other TCI methods, PMED induces mucosal responses that contribute to improved protection from mucosal challenges[71,75,76]. PMED delivery of plasmid expressing the FcR-targeted vaccine may thus offer a potent strategy to induce/increase mucosal immunity. Therefore, DNA immunizations will be administered into the epidermal layer of the skin using the PowderJect XR-1 particle mediated epidermal delivery (PMED) research device as previously described[59,93]. Optimum DNA vaccine doses in mice consist of 2 μg DNA and 1 mg gold divided into two tandem sites per mouse. Two doses (prime+boost) will be administered per animal 4 weeks apart. Controls will include PBS or empty DNA vector.

Aim 3.3: Determine the breadth of protective immunity against multiple Sp challenge strains.

While one object of the present application is establishing a potentially highly potent adjuvant-free mucosal vaccine platform applicable to many pathogens, cross-protection studies will ultimately be important in initially establishing this vaccine platform as a potentially viable approach for Sp vaccination. Utilizing the optimal immunization regimen identified above, hFcγRI/FcRn-expressing mice will be immunized with the optimal vaccine regimen versus Prevnar®13 and will then be challenged with two additional strains of Sp [D39 (Serotype 2, PspA family 1, PspA clade 2) and 3JYP2670 (Serotype 3, PspA family 2, PspA clade 4)]. Protection will then be compared to that of strain A66.1 (Serotype 3, PspA family 1, PspA clades 1,2)[94]. In regard to strain variability, while pairwise comparisons of PspA genes and proteins have been made, only the Rx1 strain from which the FP PspA was generated, was included[37]. Thus, direct gene/protein comparisons of Rx1, A66.1, D39, and 3JYP2670 are not available. However, strains from family 1, clades 1,2 (analogous to A66.1) share 65-86% identity with the Rx1-derived PspA. The case is similar for family 1, clade 2 strains (analogous to D39). Strains from family 2, clade 4 (analogous to 3JYP2670) share 54-57% identity with the Rx1 PspA. We will examine both protection and bacterial burden in the case of each challenge strain.

While we also recognize that the level of nasopharyngeal carriage is also an important correlate of vaccine efficacy against Sp infection, given one object of the present application is to development a novel and paradigm-changing vaccine platform, applicable to a range of infectious disease agents, we presently consider Sp carriage studies beyond the scope of this specific project.

Based on our preliminary studies using a DNA vaccine derived from the bivalent anti-hFcγRI-PspA FP administered i.n., in which we observed enhanced anti-Sp Ab production (FIG. 9), we expect we will be able to successfully develop and optimize an i.n. administered hFcR-targeted DNA vaccine-prime FP-boost regimen. Also, based on numerous studies demonstrating the ability of DNA-prime protein-boost strategies to increase vaccine potency, we expect that will similarly be the case for our hFcR-targeted DNA vaccine-prime FP-boost approach. However, should the DNA-prime FP-boost strategy fail to improve the efficacy of the FP vaccine, we will focus on the further development of hFcR-targeted DNA and FP vaccine strategies independently, since each approach may have beneficial characteristics, which could be valuable in future vaccine development, depending on the specific circumstances and pathogen involved.

It is contemplated that continued studies will focus on moving the innovative and paradigm altering (adjuvant-free) mucosal vaccine platform toward clinical trials. These studies will also take advantage of the ability of our FP(s) to bind to FcγRI in non-human primates (NHPs) (FIG. 10).

The present application is not limited to the use of recombinant protein/peptide epitopes, but, in the case of the FP vaccine, it is contemplated that it may be adapted to use with whole inactivated vaccines. This will be accomplished by substituting antigen with a moiety that binds inactivated organisms, such as inactivated *F. tularensis*, a biodefense pathogen, which the PI's laboratory has previously shown can enhance protection against *F. tularensis* challenge when targeted to FcR intranasally[8,9].

Protection after FP immunization is eliminated in wild-type (WT-negative control) mice, which lack hFcγRI. Similar differences in immunity are also obtained when comparing PspA immunization of Tg mice with that of hFcγRI-targeted PspA FP, with the latter also producing enhanced anti-Sp Ab responses and protection. Data is provided in FIG. 11 demonstrating the successful production of trivalent and hFcγRI/FcRn-binding FPs, as well as the construction of PspA and anti-hFcγRI-PspA-containing DNA vaccine vectors (FIG. 7). Importantly, hFcRn-binding was only observed with the anti-hFcγRI-PspA-HSA FP and not anti-hFcγRI-PspA (negative control). Trivalent and HSA-containing FPs bind hFcγRI on hFcγRI-expressing U937 cells: Supernatants from FP construct-transfected NSO cells were screened by flow cytometry for the presence of FPs and the ability of trimeric and HSA-containing/FcRn-binding FPs to bind hFcγRI on U937 cells. Briefly, hFcγRI-expressing U937 cells were incubated for 2 hrs at 4° C. with culture medium, supernatant from non-transfected NSO cells, or supernatant from FP transfected cells in the presence of human IgG (to block non-specific FcR binding of Rb Abs), followed by 3 washes, a 1 h incubation with Rb anti-PspA or Rb anti-HSA Ab, 3 washes, and a 30 mm incubation with goat anti-Rb IgG-FITC. Cells were then washed, fixed, and analyzed by flow cytometry. P<0.005, *p<0.0001

FIG. 12 Map of pJG582 Vector—The pJG582 vector contains four tandem 5' to 3' DNA sequences encoding humanized VL-VH-VL-VH ScFv fragments derived from the humanized 22 (anti-human FcγRI) monoclonal antibody. These segments are joined by flexible linker sequences and flanked on the 5' end by a CMV promoter, which induces FP production by eukaryotic cells. 3' of the above V segments are XhoI/NotI restriction sites between which DNA sequences encoding antigen, such as PspA, or other molecules, can be inserted. 3' of the XhoI/NotI insertion site is a neo resistance gene used for selection of transfected cells expressing the desired FP. In addition, within this vector is a signal sequence, which directs secretion of the FP by eukaryotic cells producing it.

FIG. 14 Map of pJV-7563 Vector (No secretion signal). Note: The sequences for PspA or the anti-human FcγRI-PspA fusion proteins have been inserted between NheI and Bgl-II restriction sites.

FIG. 15 Map of pUW-160s Vector (Contains secretion signal). This Plasmid has a Lysozyme secretion signal (Labeled as Lysozyme SP), which facilitates secretion of attached polypeptides through plasma membranes. Note: While making vaccine constructs the stuffer fragment has been replaced with either PspA or anti-human FcγRI-PspA fusion protein.

Generation of DNA Constructs: These constructs were generated from the original bivalent anti-FcγRI-PspA construct within the pjG582 plasmid.

Trivalent Anti-FcγRI-PspA (Construct B):

The cloning strategy of this construct was modified due to the repetitive sequence/domain nature of the construct itself. Instead of using an "inverse PCR" approach to insert two new restriction sites for the cloning of the third FcγRI, I had to use a "modular PCR" approach. Briefly, two PCR products were generated. The first used primers:

```
                                        (SEQ ID NO: 1)
FW 5'-ATAAGCGCTGGAGGCGGAGGTTCTAGTGA-3'
and

                                        (SEQ ID NO: 2)
RV 5'-AGAATTCGCTAGCAGTCGAGCCTCCCCCACCGGT.
```

This generated a PCR fragment that was 792 bp in length and encompassed nucleotides 1729 to 2520 in the parent construct. The second PCR used primers: FW 5'-A GAATTCATGGAAGAATCTCCCGTAGCCA-3' (SEQ ID NO:3) and RV 5'-ATA AGCGCTGGTCGAGCCTCCCCCACCGGT-3' (SEQ ID NO:4). This generated a PCR fragment that was 7.3 kb in length and encompassed nucleotides 2521 to 1728 (wrapping). Each PCR product was digested with AfeI and EcoRI and ligated together to form the "new" parent construct, depicted below. Restriction sites on the top were introduced in the cloning reactions. Restriction sites on the bottom were present in the parent construct.

This construct was verified by sequencing.

Construct A is shown in FIG. 16.

The next step was to PCR the FcγRI portion using primers with flanking NheI and EcoRI sites (FW: 5'-T GCTAGCGGAGGCGGAGGTTCTAGTGA-3' (SEQ ID NO:5) and RV: 5'-A GAATTCAGTCGAGCCTCCCCCACCGGT-3' (SEQ ID NO:6)). This PCR product and the new parent construct (above) were digested with NheI and EcoRI and ligated together to form the construct below.

This construct was verified by sequencing with the caveat that the middle FcγRI section could not be fully sequenced (see below). However, this region was sequenced in Construct A (shown in FIG. 16).

Trivalent Anti-FcγRI-PspA (Construct B):

Construct A was then subject to inverse PCR for introduction of two new restriction sites downstream of PspA for cloning in the HuSA. One PCR was performed using the primers: FW 5'-AT CGTACGCACCACCACCACCACCACTGA-3' (SEQ ID NO:7) and RV 5'-AT CGTACGTGTACAACCGCCTGATCCACCCTCGAGTT CTGGGGCTGGAGTTTC T-3' (SEQ ID NO:8). This PCR product was digested with BsiWI and ligated together to form the following construct.

Bivalent Anti-FcγRI-PspA-HuSA (Construct D):

Construct C is shown in FIG. 17.

The HuSA sequence was amplified using the following primers: FW 5'-tgtacactagagaagtgctgtgccgct-3' (SEQ ID NO:9) and RV 5'-cgtacgtaagcctaaggcagcttgactt-3' (SEQ ID NO:10). This PCR product and Construct C was digested with BsiWI and BsrGI and ligated together to form the following construct. This construct was verified by sequencing.

Bivalent Anti-FcγRI-PspA-HuSA (Construct D):

Construct D is shown in FIG. 17.

Construct B was subject to the same inverse PCR as Construct A to form the following construct:

Trivalent Anti-FcγRI-PspA-HuSA (Construct F):

Construct E is shown in FIG. 18.

The HuSA PCR product and Construct E was digested with BsiWI and BsrGI and ligated together to form the following construct. This construct was verified by sequencing with the caveat that the middle FcγRI section could not be fully sequenced (see below). However, this region was sequenced in Construct D.

Trivalent Anti-FcγRI-PspA-HuSA (Construct F):

Construct F is shown in FIG. 18.

To form the non-targeting PspA-HuSA construct, Construct D was digested with AgeI, the large, vector band was gel extracted and ligated to form the following construct. This construct was verified by sequencing.

Non-FcγRI-Targeted PspA-HuSA (Construct G):

Construct G is shown in FIG. 19.

Each construct has been verified by sequencing to the extent that the technology allows. The middle FcγRI domain for Construct B and Construct F could not be verified because unique sequencing primers could not be designed to cover this region due to the repetitive nature of the construct. However, because this region was sequence verified in Construct A and D, it is believed that it is mutation free in the trivalent forms.

For unknown reasons, the AfeI site that was introduced through modular PCR caused problems with sequencing reactions and subsequent PCR. Regardless, the constructs do cut with AfeI with the correct predicted sizes, therefore, it is believed that this site is structurally sound even though it has not been proven with sequence data.

A comparison of the proposed Sp and flu FP vaccines to licensed vaccines is presented in Table I. It is contemplated that the Ag component within the FP may be replaced with a molecule, which binds inactivated microorganisms such as inactivated *F. tularensis* (iFt), with which one of the present inventors has demonstrated the ability to protect against the highly lethal human virulent strain Ft SchuS4 via FcR targeting (i.n administered iFt). Importantly, this would add yet another major capability to this platform, significantly expanding its application to inactivated microbial vaccines.

TABLE I

Comparison of Proposed Sp and flu FP Vaccines to Licensed Vaccines

| Key Features | Sp or HA FP (FcR targeted) | Prevnar (Conjugate) | FluZone (killed) | FluMist (live attenuated) |
|---|---|---|---|---|
| Induces protective Ab | YES | YES | YES | YES |
| Induces protective T cell responses | YES | NO | NO | YES |
| Induces mucosal immunity | YES | NO | NO | YES |
| Single Ag affords cross-protection against different strains | YES | YES | NO | SLIGHT |
| Requires adjuvant | NO | YES | YES | NO |
| Induces long-term immunity without annual boosting | YES | NO | NO | NO |
| Rapid manufacture | YES | NO | NO | NO |
| Stability supports long-term stockpiling | YES | YES | NO | NO |
| Very safe in all segments of the population | YES | YES | YES | NO |

One object of the present application is to identify a single FcR-targeted vaccine platform that affords optimal protection to bacterial and viral mucosal challenge utilizing mouse bacterial and viral infection models, which is also broadly applicable to the majority of respiratory biodefense (Table 2), as well as non-biodefense pathogens. However, it is recognized that the FP, DNA, or DNA prime-FP boost platforms could each provide unique advantages suitable to specific pathogens. Thus, these studies could also lead to the advancement of pathogen-specific vaccine design(s) for individual and combination vaccines, dependent on the pathogen (s) of interest (bacterial or viral), route of entry (mucosal or parenteral), and protective response(s) (humoral or cellular) required. Once the optimal vaccine regimen/platform is identified, similar studies will then be conducted in NHPs. Interim's will be: 1) To determine if increasing the valency of the hFcγRI targeting component in the FP is superior to the proven bivalent FP; 2) To determine if adding an FcRn targeting component to the FP will further increase the potency of the bivalent or trivalent FP; 3) To determine if a hFcγRI-targeted DNA vaccine is efficacious vs. non-targeted DNA vaccine; 4) To determine if a hFcγRI-targeted DNA prime-FP boost regimen is superior to DNA or FP regimens; 5) To determine if a multipathogen (combination) vaccine platform is efficacious by combining optimized Sp and flu vaccine platforms. Once NHP studies are completed demonstrating the efficacy of this approach in this model, the final platform formulation will be put into large-scale production. However, prior to initiating large scale production and clinical studies, the PspA and HA Ags used will be re-evaluated to determine if in the interim, superior Ags more appropriate for clinical application against these pathogens have been identified. Also, protective Ags against biodefense pathogens such as Ft may have been identified at this point, which could be used with this platform, expanding the potential for clinical trials with Category A-C biodefense pathogens, in addition to those pathogens utilized in these studies.

TABLE 2

Biothreat Agents That Present Risk for Aerosol/Mucosal Delivery

| Category A | Category B | Category C |
|---|---|---|
| Anthrax | *Coxiella burnetti* (Q fever) | Influenza |
| Pneumonic plague | *Brucella* species (brucellosis) | SARS and associated coronaviruses |
| Tularemia | *Burkholderia mallei* (glanders) | |
| Filoviruses | Equine encephalitis viruses | |
| Arenaviruses | | |
| Bunyaviruses | | |

The contents of each of the below-identified references are hereby incorporated by reference.

1. Nguyen, H. H., Moldoveanu, Z., Novak, M. J., van Ginkel, F. W., Ban, E., Kiyono, H., McGhee, J. R. & Mestecky, J. Heterosubtypic immunity to lethal *influenza* A virus infection is associated with virus-specific CD8(+) cytotoxic T lymphocyte responses induced in mucosa-associated tissues. *Virology* 254, 50-60 (1999).
2. Renegar, K. B., Small, P. A., Jr., Boykins, L. G. & Wright, P. F. Role of IgA versus IgG in the control of *influenza* viral infection in the murine respiratory tract. *J Immunol* 173, 1978-1986 (2004).
3. Ito, R., Ozaki, Y. A., Yoshikawa, T., Hasegawa, H., Sato, Y., Suzuki, Y., Inoue, R., Morishima, T., Kondo, N., Sata, T., Kurata, T. & Tamura, S. Roles of anti-hemagglutinin IgA and IgG antibodies in different sites of the respiratory tract of vaccinated mice in preventing lethal *influenza* pneumonia. *Vaccine* 21, 2362-2371 (2003).
4. Chen, Z., Kadowaki, S., Hagiwara, Y., Yoshikawa, T., Matsuo, K., Kurata, T. & Tamura, S. Cross-protection against a lethal *influenza* virus infection by DNA vaccine to neuraminidase. *Vaccine* 18, 3214-3222 (2000).
5. McGhee, J. R. A mucosal gateway for vaccines. *Nat Biotechnol* 29, 136-138 (2011).
6. Guyre, C. A., Keler, T., Swink, S. L., Vitale, L. A., Graziano, R. F. & Fanger, M. W. Receptor modulation by Fc gamma RI-specific fusion proteins is dependent on receptor number and modified by IgG. *J Immunol* 167, 6303-6311 (2001).
7. Bitsaktsis, C., Iglesias, B. V., Li, Y., Colino, J., Snapper, C. M., Hollingshead, S. K., Pham, G., Gosselin, D. R. & Gosselin, E. J. Mucosal immunization with an unadjuvanted vaccine that targets *Streptococcus pneumoniae* PspA to human Fcgamma receptor type I protects against pneumococcal infection through complement- and lactoferrin-mediated bactericidal activity. *Infect Immun* 80, 1166-1180 (2012).
8. Rawool, D. B., Bitsaktsis, C., Li, Y., Gosselin, D. R., Lin, Y., Kurkure, N. V., Metzger, D. W. & Gosselin, E. J. Utilization of Fc receptors as a mucosal vaccine strategy against an intracellular bacterium, *Francisella tularensis. J Immunol* 180, 5548-5557 (2008).
9. Iglesias, B. V., Bitsaktsis, C., Pham, G., Drake, J. R., Hazlett, K. R., Porter, K. & Gosselin, E. J. Multiple mechanisms mediate enhanced immunity generated by mAb-inactivated *F. tularensis* immunogen. *Immunology and cell biology* 91, 139-148 (2013).
10. Keler, T., Guyre, P. M., Vitale, L. A., Sundarapandiyan, K., van De Winkel, J. G., Deo, Y. M. & Graziano, R. F. Targeting weak antigens to CD64 elicits potent humoral responses in human CD64 transgenic mice. *J Immunol* 165, 6738-6742 (2000).
11. Lu, S. Heterologous prime-boost vaccination. *Curr Opin Immunol* 21, 346-351 (2009).
12. Chaudhury, C., Brooks, C. L., Carter, D. C., Robinson, J. M. & Anderson, C. L. Albumin binding to FcRn: distinct from the FcRn-IgG interaction. *Biochemistry* 45, 4983-4990 (2006).
13. Kenanova, V. E., Olafsen, T., Salazar, F. B., Williams, L. E., Knowles, S. & Wu, A. M. Tuning the serum persistence of human serum albumin domain III: diabody fusion proteins. *Protein Eng Des Sel* 23, 789-798 (2010).
14. van Montfoort, N., t Hoen, P. A., Mangsbo, S. M., Camps, M. G., Boross, P., Melief, C. J., Ossendorp, F. & Verbeek, J. S. Fcgamma receptor IIb strongly regulates Fcgamma receptor-facilitated T cell activation by dendritic cells. *J Immunol* 189, 92-101 (2012).
15. Boruchov, A. M., Heller, G., Veri, M. C., Bonvini, E., Ravetch, J. V. & Young, J. W. Activating and inhibitory IgG Fc receptors on human DCs mediate opposing functions. *J Clin Invest* 115, 2914-2923 (2005).
16. Wei, C. J., Boyington, J. C., McTamney, P. M., Kong, W. P., Pearce, M. B., Xu, L., Andersen, H., Rao, S., Tumpey, T. M., Yang, Z. Y. & Nabel, G. J. Induction of broadly neutralizing H1N1 *influenza* antibodies by vaccination. *Science* 329, 1060-1064 (2010).
17. Haddad, D., Liljeqvist, S., Stahl, S., Hansson, M., Perlmann, P., Ahlborg, N. & Berzins, K. Characterization of antibody responses to a *Plasmodium falciparum* blood-stage antigen induced by a DNA prime/protein boost immunization protocol. *Scandinavian journal of immunology* 49, 506-514 (1999).
18. Leung, L., Srivastava, I. K., Kan, E., Legg, H., Sun, Y., Greer, C., Montefiori, D. C., zur Megede, J. & Barnett, S. W. Immunogenicity of HIV-1 Env and Gag in baboons using a DNA prime/protein boost regimen. *AIDS* 18, 991-1001 (2004).
19. Otten, G. R., Schaefer, M., Doe, B., Liu, H., Srivastava, I., Megede, J., Kazzaz, J., Lian, Y., Singh, M., Ugozzoli, M., Montefiori, D., Lewis, M., Driver, D. A., Dubensky, T., Polo, J. M., Donnelly, J., O'Hagan, D. T., Barnett, S. & Ulmer, J. B. Enhanced potency of plasmid DNA microparticle human immunodeficiency virus vaccines in rhesus macaques by using a priming-boosting regimen with recombinant proteins. *J Virol* 79, 8189-8200 (2005).

20. Tanghe, A., D'Souza, S., Rosseels, V., Denis, O., Ottenhoff, T. H., Dalemans, W., Wheeler, C. & Huygen, K. Improved immunogenicity and protective efficacy of a tuberculosis DNA vaccine encoding Ag85 by protein boosting. *Infect Immun* 69, 3041-3047 (2001).
21. Kensil, C. R., Mo, A. X. & Truneh, A. Current vaccine adjuvants: an overview of a diverse class. *Front Biosci* 9, 2972-2988 (2004).
22. McGhee, J. R. & Kiyono, H. Effective mucosal immunity. Current concepts for vaccine delivery and immune response analysis. *Int J Technol Assess Health Care* 10, 93-106 (1994).
23. Holmgren, J. & Czerkinsky, C. Mucosal immunity and vaccines. *Nat Med* 11, S45-53 (2005).
24. Neutra, M. R. & Kozlowski, P. A. Mucosal vaccines: the promise and the challenge. *Nature reviews. Immunology* 6, 148-158 (2006).
25. Mestecky, J. & McGhee, J. R. Prospects for human mucosal vaccines. *Advances in experimental medicine and biology* 327, 13-23 (1992).
26. Areas, A. P., Oliveira, M. L., Miyaji, E. N., Leite, L. C., Aires, K. A., Dias, W. O. & Ho, P. L. Expression and characterization of cholera toxin B-pneumococcal surface adhesin A fusion protein in *Escherichia coli*: ability of CTB-PsaA to induce humoral immune response in mice. *Biochem Biophys Res Commun* 321, 192-196 (2004).
27. Boyaka, P. N., Lillard, J. W., Jr. & McGhee, J. Interleukin 12 and innate molecules for enhanced mucosal immunity. *Immunol Res* 20, 207-217 (1999).
28. McCluskie, M. J. & Weeratna, R. D. Novel adjuvant systems. *Curr Drug Targets Infect Disord* 1, 263-271 (2001).
29. Gosselin, E. J., Bitsaktsis, C., Li, Y. & Iglesias, B. V. Fc receptor-targeted mucosal vaccination as a novel strategy for the generation of enhanced immunity against mucosal and non-mucosal pathogens. *Arch Immunol Ther Exp (Warsz)* 57, 311-323 (2009).
30. Lu, L., Palaniyandi, S., Zeng, R., Bai, Y., Liu, X., Wang, Y., Pauza, C. D., Roopenian, D. C. & Zhu, X. A neonatal Fc receptor-targeted mucosal vaccine strategy effectively induces HIV-1 antigen-specific immunity to genital infection. *J Virol* 85, 10542-10553 (2011).
31. Ye, L., Zeng, R., Bai, Y., Roopenian, D. C. & Zhu, X. Efficient mucosal vaccination mediated by the neonatal Fc receptor. *Nat Biotechnol* 29, 158-163 (2011).
32. Dickinson, B. L., Badizadegan, K., Wu, Z., Ahouse, J. C., Zhu, X., Simister, N. E., Blumberg, R. S. & Lencer, W. I. Bidirectional FcRn-dependent IgG transport in a polarized human intestinal epithelial cell line. *J Clin Invest* 104, 903-911 (1999).
33. Kobayashi, N., Suzuki, Y., Tsuge, T., Okumura, K., Ra, C. & Tomino, Y. FcRn-mediated transcytosis of immunoglobulin G in human renal proximal tubular epithelial cells. *Am J Physiol Renal Physiol* 282, F358-365 (2002).
34. Hershberg, R. M., Cho, D. H., Youakim, A., Bradley, M. B., Lee, J. S., Framson, P. E. & Nepom, G. T. Highly polarized HLA class II antigen processing and presentation by human intestinal epithelial cells. *J Clin Invest* 102, 792-803 (1998).
35. Sardella, A., Voisin, C., Nickmilder, M., Dumont, X., Annesi-Maesano, I. & Bernard, A. Nasal epithelium integrity, environmental stressors, and allergic sensitization: a biomarker study in adolescents. *Biomarkers: biochemical indicators of exposure, response, and susceptibility to chemicals* 17, 309-318 (2012).
36. Schaper, C., Gustavus, B., Koch, B., Ewert, R., Felix, S. B., Kunkel, G., Noga, O. & Glaser, S. Effect of fluticasone on neuropeptides in nasal lavage in persistent allergic rhinitis. *Journal of investigational allergology & clinical immunology* 20, 214-221 (2010).
37. Hollingshead, S. K., Becker, R. & Briles, D. E. Diversity of PspA: mosaic genes and evidence for past recombination in *Streptococcus pneumoniae. Infect Immun* 68, 5889-5900 (2000).
38. Gosselin, E. J., Dennett, J. C., Sorenson, G. D., Pettengill, O. S. & Cate, C. C. Immunocytochemical staining of cytocentrifuge prepared cultured cells: nonspecific staining and its elimination. *Histochem J* 17, 847-858 (1985).
39. Bumann, D., Metzger, W. G., Mansouri, E., Palme, O., Wendland, M., Hurwitz, R., Haas, G., Aebischer, T., von Specht, B. U. & Meyer, T. F. Safety and immunogenicity of live recombinant *Salmonella enterica* serovar Typhi Ty21a expressing urease A and B from *Helicobacter pylori* in human volunteers. *Vaccine* 20, 845-852 (2001).
40. Bitsaktsis, C., Rawool, D. B., Li, Y., Kurkure, N. V., Iglesias, B. & Gosselin, E. J. Differential requirements for protection against mucosal challenge with *Francisella tularensis* in the presence versus absence of cholera toxin B and inactivated *F. tularensis. J Immunol* 182, 4899-4909 (2009).
41. Gosselin, E. J., Cate, C. C., Pettengill, O. S. & Sorenson, G. D. Immunocytochemistry: its evolution and criteria for its application in the study of epon-embedded cells and tissue. *Am J Anat* 175, 135-160 (1986).
42. Gosselin, E. J. & Parker, D. C. Class II MHC molecules and antigen enter the same vesicles during internalization by resting B lymphocytes. *Cell Immunol* 129, 404-413 (1990).
43. Andersen, J. T., Daba, M. B., Berntzen, G., Michaelsen, T. E. & Sandlie, I. Cross-species binding analyses of mouse and human neonatal Fc receptor show dramatic differences in immunoglobulin G and albumin binding. *J Biol Chem* 285, 4826-4836 (2010).
44. Daniels, C. C., Coan, P., King, J., Hale, J., Benton, K. A., Briles, D. E. & Hollingshead, S. K. The proline-rich region of pneumococcal surface proteins A and C contains surface-accessible epitopes common to all pneumococci and elicits antibody-mediated protection against sepsis. *Infect Immun* 78, 2163-2172 (2010).
45. Bagley, K. C., Abdelwahab, S. F., Tuskan, R. G. & Lewis, G. K. An enzymatically active a domain is required for cholera-like enterotoxins to induce a long-lived blockade on the induction of oral tolerance: new method for screening mucosal adjuvants. *Infect Immun* 71, 6850-6856 (2003).
46. Mowat, A. M. Dendritic cells and immune responses to orally administered antigens. *Vaccine* 23, 1797-1799 (2005).
47. Saint-Lu, N., Tourdot, S., Razafindratsita, A., Mascarell, L., Berjont, N., Chabre, H., Louise, A., Van Overtvelt, L. & Moingeon, P. Targeting the allergen to oral dendritic cells with mucoadhesive chitosan particles enhances tolerance induction. *Allergy* 64, 1003-1013 (2009).
48. Sun, J. B., Czerkinsky, C. & Holmgren, J. Mucosally induced immunological tolerance, regulatory T cells and the adjuvant effect by cholera toxin B subunit. *Scandinavian journal of immunology* 71, 1-11 (2010).
49. Moise, L., Song, C., Martin, W. D., Tassone, R., De Groot, A. S. & Scott, D. W. Effect of HLA DR epitope de-immunization of Factor VIII in vitro and in vivo. *Clin Immunol* 142, 320-331 (2012).

50. Wallace, P. K., Keler, T., Guyre, P. M. & Fanger, M. W. Fc gamma RI blockade and modulation for immunotherapy. *Cancer Immunol Immunother* 45, 137-141 (1997).
51. Adamova, E., Walsh, M. C., Gosselin, D. R., Hale, K., Preissler, M. T., Graziano, R. F. & Gosselin, E. J. Enhanced antigen-specific antibody and cytokine responses when targeting antigen to human FcGAMMA receptor type I using an anti-human FcGAMMA receptor type I-streptavidin fusion protein in an adjuvant-free system. *Immunological investigations* 34, 417-429 (2005).
52. Yager, E. J., Dean, H. J. & Fuller, D. H. Prospects for developing an effective particle-mediated DNA vaccine against *influenza. Expert Rev Vaccines* 8, 1205-1220 (2009).
53. Fuller, D. H., Loudon, P. & Schmaljohn, C. Preclinical and clinical progress of particle-mediated DNA vaccines for infectious diseases. *Methods* 40, 86-97 (2006).
54. Miyaji, E. N., Ferreira, D. M., Lopes, A. P., Brandileone, M. C., Dias, W. O. & Leite, L. C. Analysis of serum cross-reactivity and cross-protection elicited by immunization with DNA vaccines against *Streptococcus pneumoniae* expressing PspA fragments from different clades. *Infect Immun* 70, 5086-5090 (2002).
55. Nguyen, C. T., Kim, S. Y., Kim, M. S., Lee, S. E. & Rhee, J. H. Intranasal immunization with recombinant PspA fused with a flagellin enhances cross-protective immunity against *Streptococcus pneumoniae* infection in mice. *Vaccine* 29, 5731-5739 (2011).
56. Goulart, C., Darrieux, M., Rodriguez, D., Pimenta, F. C., Brandileone, M. C., de Andrade, A. L. & Leite, L. C. Selection of family 1 PspA molecules capable of inducing broad-ranging cross-reactivity by complement deposition and opsonophagocytosis by murine peritoneal cells. *Vaccine* 29, 1634-1642 (2011).
57. Briles, D. E., Hollingshead, S. K., King, J., Swift, A., Braun, P. A., Park, M. K., Ferguson, L. M., Nahm, M. H. & Nabors, G. S. Immunization of humans with recombinant pneumococcal surface protein A (rPspA) elicits antibodies that passively protect mice from fatal infection with *Streptococcus pneumoniae* bearing heterologous PspA. *J Infect Dis* 182, 1694-1701 (2000).
58. Drape, R. J., Macklin, M. D., Barr, L. J., Jones, S., Haynes, J. R. & Dean, H. J. Epidermal DNA vaccine for *influenza* is immunogenic in humans. *Vaccine* 24, 4475-4481 (2006).
59. Roy, M. J., Wu, M. S., Barr, L. J., Fuller, J. T., Tussey, L. G., Speller, S., Culp, J., Burkholder, J. K., Swain, W. F., Dixon, R. M., Widera, G., Vessey, R., King, A., Ogg, G., Gallimore, A., Haynes, J. R. & Heydenburg Fuller, D. Induction of antigen-specific CD8+ T cells, T helper cells, and protective levels of antibody in humans by particle-mediated administration of a *hepatitis* B virus DNA vaccine. *Vaccine* 19, 764-778 (2000).
60. Shim, B. S., Park, S. M., Quan, J. S., Jere, D., Chu, H., Song, M. K., Kim, D. W., Jang, Y. S., Yang, M. S., Han, S. H., Park, Y. H., Cho, C. S. & Yun, C. H. Intranasal immunization with plasmid DNA encoding spike protein of SARS-coronavirus/polyethylenimine nanoparticles elicits antigen-specific humoral and cellular immune responses. *BMC immunology* 11, 65 (2010).
61. Torrieri-Dramard, L., Lambrecht, B., Ferreira, H. L., Van den Berg, T., Klatzmann, D. & Bellier, B. Intranasal DNA vaccination induces potent mucosal and systemic immune responses and cross-protective immunity against *influenza* viruses. *Molecular therapy: the journal of the American Society of Gene Therapy* 19, 602-611 (2011).
62. Lawson, L. B., Clements, J. D. & Freytag, L. C. Mucosal immune responses induced by transcutaneous vaccines. *Curr Top Microbiol Immunol* 354, 19-37 (2012).
63. Condon, C., Watkins, S. C., Celluzzi, C. M., Thompson, K. & Falo, L. D., Jr. DNA-based immunization by in vivo transfection of dendritic cells. *Nat Med* 2, 1122-1128 (1996).
64. Chang, S. Y., Cha, H. R., Igarashi, O., Rennert, P. D., Kissenpfennig, A., Malissen, B., Nanno, M., Kiyono, H. & Kweon, M. N. Cutting edge: Langerin+ dendritic cells in the mesenteric lymph node set the stage for skin and gut immune system cross-talk. *Journal of immunology* 180, 4361-4365 (2008).
65. Lawson, L. B., Clements, J. D. & Freytag, L. C. Mucosal immune responses induced by transcutaneous vaccines. *Curr Top Microbiol Immunol* 354, 19-37 (2012).
66. Belyakov, I. M., Hammond, S. A., Ahlers, J. D., Glenn, G. M. & Berzofsky, J. A. Transcutaneous immunization induces mucosal CTLs and protective immunity by migration of primed skin dendritic cells. *J Clin Invest* 113, 998-1007 (2004).
67. Daynes, R. A., Enioutina, E. Y., Butler, S., Mu, H. H., McGee, Z. A. & Araneo, B. A. Induction of common mucosal immunity by hormonally immunomodulated peripheral immunization. *Infect Immun* 64, 1100-1109 (1996).
68. Enioutina, E. Y., Visic, D. & Daynes, R. A. The induction of systemic and mucosal immune responses to antigen-adjuvant compositions administered into the skin: alterations in the migratory properties of dendritic cells appears to be important for stimulating mucosal immunity. *Vaccine* 18, 2753-2767 (2000).
69. Glenn, G. M., Scharton-Kersten, T., Vassell, R., Mallett, C. P., Hale, T. L. & Alving, C. R. Transcutaneous immunization with cholera toxin protects mice against lethal mucosal toxin challenge. *J Immunol* 161, 3211-3214 (1998).
70. Enioutina, E. Y., Bareyan, D. & Daynes, R. A. TLR ligands that stimulate the metabolism of vitamin D3 in activated murine dendritic cells can function as effective mucosal adjuvants to subcutaneously administered vaccines. *Vaccine* 26, 601-613 (2008).
71. Chen, D., Periwal, S. B., Larrivee, K., Zuleger, C., Erickson, C. A., Endres, R. L. & Payne, L. G. Serum and mucosal immune responses to an inactivated *influenza* virus vaccine induced by epidermal powder immunization. *J Virol* 75, 7956-7965 (2001).
72. Czerkinsky, C. & Holmgren, J. Mucosal delivery routes for optimal immunization: targeting immunity to the right tissues. *Curr Top Microbiol Immunol* 354, 1-18 (2012).
73. Liard, C., Munier, S., Arias, M., Joulin-Giet, A., Bonduelle, O., Duffy, D., Shattock, R. J., Verrier, B. & Combadiere, B. Targeting of HIV-p24 particle-based vaccine into differential skin layers induces distinct arms of the immune responses. *Vaccine* 29, 6379-6391 (2011).
74. Mishra, D., Mishra, P. K., Dubey, V., Nahar, M., Dabadghao, S. & Jain, N. K. Systemic and mucosal immune response induced by transcutaneous immunization using Hepatitis B surface antigen-loaded modified liposomes. *Eur J Pharm Sci* 33, 424-433 (2008).
75. Fuller, D. H., Raj akumar, P. A., Wilson, L. A., Trichel, A. M., Fuller, J. T., Shipley, T., Wu, M. S., Weis, K., Rinaldo, C. R., Haynes, J. R. & Murphey-Corb, M. Induction of mucosal protection against primary, heterologous simian immunodeficiency virus by a DNA vaccine. *J Virol* 76, 3309-3317 (2002).

76. Loudon, P. T., Yager, E. J., Lynch, D. T., Narendran, A., Stagnar, C., Franchini, A. M., Fuller, J. T., White, P. A., Nyuandi, J., Wiley, C. A., Murphey-Corb, M. & Fuller, D. H. GM-CSF increases mucosal and systemic immunogenicity of an H1N1 *influenza* DNA vaccine administered into the epidermis of non-human primates. *PLoS One* 5, e11021 (2010).
77. Ghose, C., Kalsy, A., Sheikh, A., Rollenhagen, J., John, M., Young, J., Rollins, S. M., Qadri, F., Calderwood, S. B., Kelly, C. P. & Ryan, E. T. Transcutaneous immunization with *Clostridium difficile* toxoid A induces systemic and mucosal immune responses and toxin A-neutralizing antibodies in mice. *Infection and immunity* 75, 2826-2832 (2007).
78. Haynes, J. R., Fuller, D. H., McCabe, D., Swain, W. F. & Widera, G. Induction and characterization of humoral and celllar immune responses elicited via gene gun-mediated nucleic acid immunization. *Adv. Drug Delivery Rev.* 21, 3-18. (1996).
79. John, M., Bridges, E. A., Miller, A. O., Calderwood, S. B. & Ryan, E. T. Comparison of mucosal and systemic humoral immune responses after transcutaneous and oral immunization strategies. *Vaccine* 20, 2720-2726 (2002).
80. Yu, J., Cassels, F., Scharton-Kersten, T., Hammond, S. A., Hartman, A., Angov, E., Corthesy, B., Alving, C. & Glenn, G. Transcutaneous immunization using colonization factor and heat-labile enterotoxin induces correlates of protective immunity for enterotoxigenic *Escherichia coli. Infection and immunity* 70, 1056-1068 (2002).
81. Gockel, C. M., Bao, S. & Beagley, K. W. Transcutaneous immunization induces mucosal and systemic immunity: a potent method for targeting immunity to the female reproductive tract. *Mol Immunol* 37, 537-544 (2000).
82. Uddowla, S., Freytag, L. C. & Clements, J. D. Effect of adjuvants and route of immunizations on the immune response to recombinant plague antigens. *Vaccine* 25, 7984-7993 (2007).
83. Berry, L. J., Hickey, D. K., Skelding, K. A., Bao, S., Rendina, A. M., Hansbro, P. M., Gockel, C. M. & Beagley, K. W. Transcutaneous immunization with combined cholera toxin and CpG adjuvant protects against *Chlamydia muridarum* genital tract infection. *Infect Immun* 72, 1019-1028 (2004).
84. Etchart, N., Hennino, A., Friede, M., Dahel, K., Dupouy, M., Goujon-Henry, C., Nicolas, J. F. & Kaiserlian, D. Safety and efficacy of transcutaneous vaccination using a patch with the live-attenuated measles vaccine in humans. *Vaccine* 25, 6891-6899 (2007).
85. Glenn, G. M., Flyer, D. C., Ellingsworth, L. R., Frech, S. A., Frerichs, D. M., Seid, R. C. & Yu, J. Transcutaneous immunization with heat-labile enterotoxin: development of a needle-free vaccine patch. *Expert Rev Vaccines* 6, 809-819 (2007).
86. McKenzie, R., Bourgeois, A. L., Frech, S. A., Flyer, D. C., Bloom, A., Kazempour, K. & Glenn, G. M. Transcutaneous immunization with the heat-labile toxin (LT) of enterotoxigenic *Escherichia coli* (ETEC): protective efficacy in a double-blind, placebo-controlled challenge study. *Vaccine* 25, 3684-3691 (2007).
87. Enioutina, E. Y., Bareyan, D. & Daynes, R. A. Vitamin D3-mediated alterations to myeloid dendritic cell trafficking in vivo expand the scope of their antigen presenting properties. *Vaccine* 25, 1236-1249 (2007).
88. Iwata, M., Hirakiyama, A., Eshima, Y., Kagechika, H., Kato, C. & Song, S. Y. Retinoic acid imprints gut-homing specificity on T cells. *Immunity* 21, 527-538 (2004).
89. Saurer, L., McCullough, K. C. & Summerfield, A. In vitro induction of mucosa-type dendritic cells by all-trans retinoic acid. *J Immunol* 179, 3504-3514 (2007).
90. Dean, H. J., Fuller, D. & Osorio, J. E. Powder and particle-mediated approaches for delivery of DNA and protein vaccines into the epidermis. *Comp Immunol Microbiol Infect Dis* 26, 373-388 (2003).
91. Haynes, J. R. Particle-mediated DNA vaccine delivery to the skin. *Expert Opin Biol Ther* 4, 889-900 (2004).
92. Payne, L. G., Fuller, D. H. & Haynes, J. R. Particle-mediated DNA vaccination of mice, monkeys and men: looking beyond the dogma. *Curr Opin Mol Ther* 4, 459-466 (2002).
93. Pertmer, T. M., Eisenbraun, M. D., McCabe, D., Prayaga, S. K., Fuller, D. H. & Haynes, J. R. Gene gun-based nucleic acid immunization: elicitation of humoral and cytotoxic T lymphocyte responses following epidermal delivery of nanogram quantities of DNA. *Vaccine* 13, 1427-1430 (1995).
94. Darrieux, M., Miyaji, E. N., Ferreira, D. M., Lopes, L. M., Lopes, A. P., Ren, B., Briles, D. E., Hollingshead, S. K. & Leite, L. C. Fusion proteins containing family 1 and family 2 PspA fragments elicit protection against *Streptococcus pneumoniae* that correlates with antibody-mediated enhancement of complement deposition. *Infect Immun* 75, 5930-5938 (2007).

What is claimed is:

1. An immunogenic fusion protein for use as a mucosal vaccine, wherein the immunogenic fusion protein comprises an amino acid sequence selected from the group consisting of SEQ ID NO:12 and SEQ ID NO:13.

2. The immunogenic fusion protein of claim 1, wherein the fusion protein enhances transepithelial transport of the fusion protein to the nasal-associated lymphoid tissue (NALT) and enhances FcγR1 crosslinking by the fusion protein on antigen presenting cells (APC) within the NALT.

* * * * *

SEQUENCE LISTING

```
<160> NUMBER OF SEQ ID NOS: 25

<210> SEQ ID NO 1
<211> LENGTH: 29
<212> TYPE: DNA
<213> ORGANISM: Artificial sequence
<220> FEATURE:
<223> OTHER INFORMATION: primer

<400> SEQUENCE: 1

ataagcgctg gaggcggagg ttctagtga                                29


<210> SEQ ID NO 2
<211> LENGTH: 34
<212> TYPE: DNA
<213> ORGANISM: Artificial sequence
```

```
<220> FEATURE:
<223> OTHER INFORMATION: primer

<400> SEQUENCE: 2

agaattcgct agcagtcgag cctcccccac cggt                          34

<210> SEQ ID NO 3
<211> LENGTH: 29
<212> TYPE: DNA
<213> ORGANISM: Artificial sequence
<220> FEATURE:
<223> OTHER INFORMATION: primer

<400> SEQUENCE: 3

agaattcatg gaagaatctc ccgtagcca                                29

<210> SEQ ID NO 4
<211> LENGTH: 30
<212> TYPE: DNA
<213> ORGANISM: Artificial sequence
<220> FEATURE:
<223> OTHER INFORMATION: primer

<400> SEQUENCE: 4

ataagcgctg gtcgagcctc ccccaccggt                               30

<210> SEQ ID NO 5
<211> LENGTH: 27
<212> TYPE: DNA
<213> ORGANISM: Artificial sequence
<220> FEATURE:
<223> OTHER INFORMATION: primer

<400> SEQUENCE: 5

tgctagcgga ggcggaggtt ctagtga                                  27

<210> SEQ ID NO 6
<211> LENGTH: 28
<212> TYPE: DNA
<213> ORGANISM: Artificial sequence
<220> FEATURE:
<223> OTHER INFORMATION: primer

<400> SEQUENCE: 6

agaattcagt cgagcctccc ccaccggt                                 28

<210> SEQ ID NO 7
<211> LENGTH: 29
<212> TYPE: DNA
<213> ORGANISM: Artificial sequence
<220> FEATURE:
<223> OTHER INFORMATION: primer

<400> SEQUENCE: 7

atcgtacgca ccaccaccac caccactga                                29

<210> SEQ ID NO 8
<211> LENGTH: 54
<212> TYPE: DNA
<213> ORGANISM: Artificial sequence
<220> FEATURE:
<223> OTHER INFORMATION: primer

<400> SEQUENCE: 8

atcgtacgtg tacaaccgcc tgatccaccc tcgagttctg gggctggagt ttct     54
```

-continued

<210> SEQ ID NO 9
<211> LENGTH: 27
<212> TYPE: DNA
<213> ORGANISM: Artificial sequence
<220> FEATURE:
<223> OTHER INFORMATION: primer

<400> SEQUENCE: 9
tgtacactag agaagtgctg tgccgct 27

<210> SEQ ID NO 10
<211> LENGTH: 28
<212> TYPE: DNA
<213> ORGANISM: Artificial sequence
<220> FEATURE:
<223> OTHER INFORMATION: primer

<400> SEQUENCE: 10
cgtacgtaag cctaaggcag cttgactt 28

<210> SEQ ID NO 11
<211> LENGTH: 1122
<212> TYPE: PRT
<213> ORGANISM: Artificial sequence
<220> FEATURE:
<223> OTHER INFORMATION: Trivalent Anti-FcgRI---PspA

<400> SEQUENCE: 11

Met Gly Trp Ser Cys Ile Ile Leu Phe Leu Val Ala Thr Ala Thr Gly
1 5 10 15

Val His Ser Asp Ile Gln Leu Thr Gln Ser Pro Ser Ser Leu Ser Ala
20 25 30

Ser Val Gly Asp Arg Val Thr Ile Thr Cys Lys Ser Ser Gln Ser Val
35 40 45

Leu Tyr Ser Ser Asn Gln Lys Asn Tyr Leu Ala Trp Tyr Gln Gln Lys
50 55 60

Pro Gly Lys Ala Pro Lys Leu Leu Ile Tyr Trp Ala Ser Thr Arg Glu
65 70 75 80

Ser Gly Val Pro Ser Arg Phe Ser Gly Ser Gly Ser Gly Thr Asp Phe
85 90 95

Thr Phe Thr Ile Ser Ser Leu Gln Pro Glu Asp Ile Ala Thr Tyr Tyr
100 105 110

Cys His Gln Tyr Leu Ser Ser Trp Thr Phe Gly Gln Gly Thr Lys Val
115 120 125

Glu Ile Lys Ser Ser Gly Gly Gly Gly Ser Gly Gly Gly Gly Ser Gly
130 135 140

Gly Gly Gly Ser Glu Val Gln Leu Val Glu Ser Gly Gly Gly Val Val
145 150 155 160

Gln Pro Gly Arg Ser Leu Arg Leu Ser Cys Ser Ser Ser Gly Phe Ile
165 170 175

Phe Ser Asp Asn Tyr Met Tyr Trp Val Arg Gln Ala Pro Gly Lys Gly
180 185 190

Leu Glu Trp Val Ala Thr Ile Ser Asp Gly Gly Ser Tyr Thr Tyr Tyr
195 200 205

Pro Asp Ser Val Lys Gly Arg Phe Thr Ile Ser Arg Asp Asn Ser Lys
210 215 220

Asn Thr Leu Phe Leu Gln Met Asp Ser Leu Arg Pro Glu Asp Thr Gly
225 230 235 240

-continued

```
Val Tyr Phe Cys Ala Arg Gly Tyr Tyr Arg Tyr Glu Gly Ala Met Asp
                245                 250                 255

Tyr Trp Gly Gln Gly Thr Pro Val Thr Val Ser Ser Gly Ser Thr Gly
            260                 265                 270

Gly Gly Gly Ser Thr Ser Ala Gly Gly Gly Gly Ser Ser Asp Ile Gln
        275                 280                 285

Leu Thr Gln Ser Pro Ser Ser Leu Ser Ala Ser Val Gly Asp Arg Val
    290                 295                 300

Thr Ile Thr Cys Lys Ser Ser Gln Ser Val Leu Tyr Ser Ser Asn Gln
305                 310                 315                 320

Lys Asn Tyr Leu Ala Trp Tyr Gln Gln Lys Pro Gly Lys Ala Pro Lys
                325                 330                 335

Leu Leu Ile Tyr Trp Ala Ser Thr Arg Glu Ser Gly Val Pro Ser Arg
            340                 345                 350

Phe Ser Gly Ser Gly Ser Gly Thr Asp Phe Thr Phe Thr Ile Ser Ser
        355                 360                 365

Leu Gln Pro Glu Asp Ile Ala Thr Tyr Tyr Cys His Gln Tyr Leu Ser
    370                 375                 380

Ser Trp Thr Phe Gly Gln Gly Thr Lys Val Glu Ile Lys Ser Ser Gly
385                 390                 395                 400

Gly Gly Gly Ser Gly Gly Gly Gly Ser Gly Gly Gly Gly Ser Glu Val
                405                 410                 415

Gln Leu Val Glu Ser Gly Gly Gly Val Val Gln Pro Gly Arg Ser Leu
            420                 425                 430

Arg Leu Ser Cys Ser Ser Ser Gly Phe Ile Phe Ser Asp Asn Tyr Met
        435                 440                 445

Tyr Trp Val Arg Gln Ala Pro Gly Lys Gly Leu Glu Trp Val Ala Thr
    450                 455                 460

Ile Ser Asp Gly Gly Ser Tyr Thr Tyr Tyr Pro Asp Ser Val Lys Gly
465                 470                 475                 480

Arg Phe Thr Ile Ser Arg Asp Asn Ser Lys Asn Thr Leu Phe Leu Gln
                485                 490                 495

Met Asp Ser Leu Arg Pro Glu Asp Thr Gly Val Tyr Phe Cys Ala Arg
            500                 505                 510

Gly Tyr Tyr Arg Tyr Glu Gly Ala Met Asp Tyr Trp Gly Gln Gly Thr
        515                 520                 525

Pro Val Thr Val Ser Ser Gly Ser Thr Gly Gly Gly Ser Thr Ala
    530                 535                 540

Ser Gly Gly Gly Gly Ser Ser Asp Ile Gln Leu Thr Gln Ser Pro Ser
545                 550                 555                 560

Ser Leu Ser Ala Ser Val Gly Asp Arg Val Thr Ile Thr Cys Lys Ser
                565                 570                 575

Ser Gln Ser Val Leu Tyr Ser Ser Asn Gln Lys Asn Tyr Leu Ala Trp
            580                 585                 590

Tyr Gln Gln Lys Pro Gly Lys Ala Pro Lys Leu Leu Ile Tyr Trp Ala
        595                 600                 605

Ser Thr Arg Glu Ser Gly Val Pro Ser Arg Phe Ser Gly Ser Gly Ser
    610                 615                 620

Gly Thr Asp Phe Thr Phe Thr Ile Ser Ser Leu Gln Pro Glu Asp Ile
625                 630                 635                 640

Ala Thr Tyr Tyr Cys His Gln Tyr Leu Ser Ser Trp Thr Phe Gly Gln
                645                 650                 655

Gly Thr Lys Val Glu Ile Lys Ser Ser Gly Gly Gly Gly Ser Gly Gly
```

```
            660                 665                 670

Gly Gly Ser Gly Gly Gly Gly Ser Glu Val Gln Leu Val Glu Ser Gly
        675                 680                 685

Gly Gly Val Val Gln Pro Gly Arg Ser Leu Arg Leu Ser Cys Ser Ser
    690                 695                 700

Ser Gly Phe Ile Phe Ser Asp Asn Tyr Met Tyr Trp Val Arg Gln Ala
705                 710                 715                 720

Pro Gly Lys Gly Leu Glu Trp Val Ala Thr Ile Ser Asp Gly Gly Ser
                725                 730                 735

Tyr Thr Tyr Tyr Pro Asp Ser Val Lys Gly Arg Phe Thr Ile Ser Arg
            740                 745                 750

Asp Asn Ser Lys Asn Thr Leu Phe Leu Gln Met Asp Ser Leu Arg Pro
        755                 760                 765

Glu Asp Thr Gly Val Tyr Phe Cys Ala Arg Gly Tyr Tyr Arg Tyr Glu
    770                 775                 780

Gly Ala Met Asp Tyr Trp Gly Gln Gly Thr Pro Val Thr Val Ser Ser
785                 790                 795                 800

Gly Ser Thr Gly Gly Gly Gly Ser Thr Glu Phe Met Glu Glu Ser Pro
                805                 810                 815

Val Ala Ser Gln Ser Lys Ala Glu Lys Asp Tyr Asp Ala Ala Lys Lys
            820                 825                 830

Asp Ala Lys Asn Ala Lys Lys Ala Val Glu Asp Ala Gln Lys Ala Leu
        835                 840                 845

Asp Asp Ala Lys Ala Ala Gln Lys Lys Tyr Asp Glu Asp Gln Lys Lys
    850                 855                 860

Thr Glu Glu Lys Ala Ala Leu Glu Lys Ala Ala Ser Glu Glu Met Asp
865                 870                 875                 880

Lys Ala Val Ala Ala Val Gln Gln Ala Tyr Leu Ala Tyr Gln Gln Ala
                885                 890                 895

Thr Asp Lys Ala Ala Lys Asp Ala Ala Asp Lys Met Ile Asp Glu Ala
            900                 905                 910

Lys Lys Arg Glu Glu Glu Ala Lys Thr Lys Phe Asn Thr Val Arg Ala
        915                 920                 925

Met Val Val Pro Glu Pro Glu Gln Leu Ala Glu Thr Lys Lys Lys Ser
    930                 935                 940

Glu Glu Ala Lys Gln Lys Ala Pro Glu Leu Thr Lys Lys Leu Glu Glu
945                 950                 955                 960

Ala Lys Ala Lys Leu Glu Glu Ala Glu Lys Lys Ala Thr Glu Ala Lys
                965                 970                 975

Gln Lys Val Asp Ala Glu Glu Val Ala Pro Gln Ala Lys Ile Ala Glu
            980                 985                 990

Leu Glu Asn Gln Val His Arg Leu  Glu Gln Glu Leu Lys  Glu Ile Asp
        995                 1000                1005

Glu Ser  Glu Ser Glu Asp Tyr  Ala Lys Glu Gly Phe  Arg Ala Pro
    1010                1015                1020

Leu Gln  Ser Lys Leu Asp Ala  Lys Lys Ala Lys Leu  Ser Lys Leu
    1025                1030                1035

Glu Glu  Leu Ser Asp Lys Ile  Asp Glu Leu Asp Ala  Glu Ile Ala
    1040                1045                1050

Lys Leu  Glu Asp Gln Leu Lys  Ala Ala Glu Glu Asn  Asn Asn Val
    1055                1060                1065

Glu Asp  Tyr Phe Lys Glu Gly  Leu Glu Lys Thr Ile  Ala Ala Lys
    1070                1075                1080
```

-continued

```
Lys Ala Glu Leu Glu Lys Thr Glu Ala Asp Leu Lys Lys Ala Val
    1085                1090                1095

Asn Glu Pro Glu Lys Pro Ala Pro Ala Pro Glu Thr Pro Ala Pro
    1100                1105                1110

Glu Leu Glu His His His His His His
    1115                1120


<210> SEQ ID NO 12
<211> LENGTH: 1097
<212> TYPE: PRT
<213> ORGANISM: Artificial sequence
<220> FEATURE:
<223> OTHER INFORMATION: Bivalent Anti-FcgRI---PspA-HuSA

<400> SEQUENCE: 12

Met Gly Trp Ser Cys Ile Ile Leu Phe Leu Val Ala Thr Ala Thr Gly
1               5                   10                  15

Val His Ser Asp Ile Gln Leu Thr Gln Ser Pro Ser Ser Leu Ser Ala
            20                  25                  30

Ser Val Gly Asp Arg Val Thr Ile Thr Cys Lys Ser Ser Gln Ser Val
        35                  40                  45

Leu Tyr Ser Ser Asn Gln Lys Asn Tyr Leu Ala Trp Tyr Gln Gln Lys
    50                  55                  60

Pro Gly Lys Ala Pro Lys Leu Leu Ile Tyr Trp Ala Ser Thr Arg Glu
65                  70                  75                  80

Ser Gly Val Pro Ser Arg Phe Ser Gly Ser Gly Ser Gly Thr Asp Phe
                85                  90                  95

Thr Phe Thr Ile Ser Ser Leu Gln Pro Glu Asp Ile Ala Thr Tyr Tyr
            100                 105                 110

Cys His Gln Tyr Leu Ser Ser Trp Thr Phe Gly Gln Gly Thr Lys Val
        115                 120                 125

Glu Ile Lys Ser Ser Gly Gly Gly Gly Ser Gly Gly Gly Gly Ser Gly
    130                 135                 140

Gly Gly Gly Ser Glu Val Gln Leu Val Glu Ser Gly Gly Gly Val Val
145                 150                 155                 160

Gln Pro Gly Arg Ser Leu Arg Leu Ser Cys Ser Ser Ser Gly Phe Ile
                165                 170                 175

Phe Ser Asp Asn Tyr Met Tyr Trp Val Arg Gln Ala Pro Gly Lys Gly
            180                 185                 190

Leu Glu Trp Val Ala Thr Ile Ser Asp Gly Gly Ser Tyr Thr Tyr Tyr
        195                 200                 205

Pro Asp Ser Val Lys Gly Arg Phe Thr Ile Ser Arg Asp Asn Ser Lys
    210                 215                 220

Asn Thr Leu Phe Leu Gln Met Asp Ser Leu Arg Pro Glu Asp Thr Gly
225                 230                 235                 240

Val Tyr Phe Cys Ala Arg Gly Tyr Tyr Arg Tyr Glu Gly Ala Met Asp
                245                 250                 255

Tyr Trp Gly Gln Gly Thr Pro Val Thr Val Ser Ser Gly Ser Thr Gly
            260                 265                 270

Gly Gly Gly Ser Thr Ser Ala Gly Gly Gly Gly Ser Ser Asp Ile Gln
        275                 280                 285

Leu Thr Gln Ser Pro Ser Ser Leu Ser Ala Ser Val Gly Asp Arg Val
    290                 295                 300

Thr Ile Thr Cys Lys Ser Ser Gln Ser Val Leu Tyr Ser Ser Asn Gln
305                 310                 315                 320
```

-continued

```
Lys Asn Tyr Leu Ala Trp Tyr Gln Gln Lys Pro Gly Lys Ala Pro Lys
                325                 330                 335

Leu Leu Ile Tyr Trp Ala Ser Thr Arg Glu Ser Gly Val Pro Ser Arg
            340                 345                 350

Phe Ser Gly Ser Gly Ser Gly Thr Asp Phe Thr Phe Thr Ile Ser Ser
        355                 360                 365

Leu Gln Pro Glu Asp Ile Ala Thr Tyr Tyr Cys His Gln Tyr Leu Ser
    370                 375                 380

Ser Trp Thr Phe Gly Gln Gly Thr Lys Val Glu Ile Lys Ser Ser Gly
385                 390                 395                 400

Gly Gly Gly Ser Gly Gly Gly Gly Ser Gly Gly Gly Gly Ser Glu Val
                405                 410                 415

Gln Leu Val Glu Ser Gly Gly Gly Val Val Gln Pro Gly Arg Ser Leu
            420                 425                 430

Arg Leu Ser Cys Ser Ser Ser Gly Phe Ile Phe Ser Asp Asn Tyr Met
        435                 440                 445

Tyr Trp Val Arg Gln Ala Pro Gly Lys Gly Leu Glu Trp Val Ala Thr
    450                 455                 460

Ile Ser Asp Gly Gly Ser Tyr Thr Tyr Tyr Pro Asp Ser Val Lys Gly
465                 470                 475                 480

Arg Phe Thr Ile Ser Arg Asp Asn Ser Lys Asn Thr Leu Phe Leu Gln
                485                 490                 495

Met Asp Ser Leu Arg Pro Glu Asp Thr Gly Val Tyr Phe Cys Ala Arg
            500                 505                 510

Gly Tyr Tyr Arg Tyr Glu Gly Ala Met Asp Tyr Trp Gly Gln Gly Thr
        515                 520                 525

Pro Val Thr Val Ser Ser Gly Ser Thr Gly Gly Gly Gly Ser Thr Ala
    530                 535                 540

Ser Glu Phe Met Glu Glu Ser Pro Val Ala Ser Gln Ser Lys Ala Glu
545                 550                 555                 560

Lys Asp Tyr Asp Ala Ala Lys Lys Asp Ala Lys Asn Ala Lys Lys Ala
                565                 570                 575

Val Glu Asp Ala Gln Lys Ala Leu Asp Asp Ala Lys Ala Ala Gln Lys
            580                 585                 590

Lys Tyr Asp Glu Asp Gln Lys Lys Thr Glu Glu Lys Ala Ala Leu Glu
        595                 600                 605

Lys Ala Ala Ser Glu Glu Met Asp Lys Ala Val Ala Ala Val Gln Gln
    610                 615                 620

Ala Tyr Leu Ala Tyr Gln Gln Ala Thr Asp Lys Ala Ala Lys Asp Ala
625                 630                 635                 640

Ala Asp Lys Met Ile Asp Glu Ala Lys Lys Arg Glu Glu Glu Ala Lys
                645                 650                 655

Thr Lys Phe Asn Thr Val Arg Ala Met Val Val Pro Glu Pro Glu Gln
            660                 665                 670

Leu Ala Glu Thr Lys Lys Lys Ser Glu Glu Ala Lys Gln Lys Ala Pro
        675                 680                 685

Glu Leu Thr Lys Lys Leu Glu Glu Ala Lys Ala Lys Leu Glu Glu Ala
    690                 695                 700

Glu Lys Lys Ala Thr Glu Ala Lys Gln Lys Val Asp Ala Glu Glu Val
705                 710                 715                 720

Ala Pro Gln Ala Lys Ile Ala Glu Leu Glu Asn Gln Val His Arg Leu
                725                 730                 735
```

-continued

```
Glu Gln Glu Leu Lys Glu Ile Asp Glu Ser Glu Ser Glu Asp Tyr Ala
            740                 745                 750

Lys Glu Gly Phe Arg Ala Pro Leu Gln Ser Lys Leu Asp Ala Lys Lys
        755                 760                 765

Ala Lys Leu Ser Lys Leu Glu Glu Leu Ser Asp Lys Ile Asp Glu Leu
    770                 775                 780

Asp Ala Glu Ile Ala Lys Leu Glu Asp Gln Leu Lys Ala Ala Glu Glu
785                 790                 795                 800

Asn Asn Asn Val Glu Asp Tyr Phe Lys Glu Gly Leu Glu Lys Thr Ile
                805                 810                 815

Ala Ala Lys Lys Ala Glu Leu Glu Lys Thr Glu Ala Asp Leu Lys Lys
            820                 825                 830

Ala Val Asn Glu Pro Glu Lys Pro Ala Pro Ala Pro Glu Thr Pro Ala
        835                 840                 845

Pro Glu Leu Glu Gly Gly Ser Gly Gly Cys Thr Leu Glu Lys Cys Cys
    850                 855                 860

Ala Ala Ala Asp Pro His Glu Cys Tyr Ala Lys Val Phe Asp Glu Phe
865                 870                 875                 880

Lys Pro Leu Val Glu Glu Pro Gln Asn Leu Ile Lys Gln Asn Cys Glu
                885                 890                 895

Leu Phe Glu Gln Leu Gly Glu Tyr Lys Phe Gln Asn Ala Leu Leu Val
            900                 905                 910

Arg Tyr Thr Lys Lys Val Pro Gln Val Ser Thr Pro Thr Leu Val Glu
        915                 920                 925

Val Ser Arg Asn Leu Gly Lys Val Gly Ser Lys Cys Cys Lys His Pro
    930                 935                 940

Glu Ala Lys Arg Met Pro Cys Ala Glu Asp Tyr Leu Ser Val Val Leu
945                 950                 955                 960

Asn Gln Leu Cys Val Leu His Glu Lys Thr Pro Val Ser Asp Arg Val
                965                 970                 975

Thr Lys Cys Cys Thr Glu Ser Leu Val Asn Arg Arg Pro Cys Phe Ser
            980                 985                 990

Ala Leu Glu Val Asp Glu Thr Tyr  Val Pro Lys Glu Phe  Asn Ala Glu
        995                 1000                1005

Thr Phe  Thr Phe His Ala Asp  Ile Cys Thr Leu Ser  Glu Lys Glu
    1010                1015                1020

Arg Gln  Ile Lys Lys Gln Thr  Ala Leu Val Glu Leu  Val Lys His
    1025                1030                1035

Lys Pro  Lys Ala Thr Lys Glu  Gln Leu Lys Ala Val  Met Asp Asp
    1040                1045                1050

Phe Ala  Ala Phe Val Glu Lys  Cys Cys Lys Ala Asp  Asp Lys Glu
    1055                1060                1065

Thr Cys  Phe Ala Glu Glu Gly  Lys Lys Leu Val Ala  Ala Ser Gln
    1070                1075                1080

Ala Ala  Leu Gly Leu Arg Thr  His His His His His  His His
    1085                1090                1095


<210> SEQ ID NO 13
<211> LENGTH: 1361
<212> TYPE: PRT
<213> ORGANISM: Artificial sequence
<220> FEATURE:
<223> OTHER INFORMATION: Trivalent Anti-FcgRI---PspA-HuSA

<400> SEQUENCE: 13
```

-continued

```
Met Gly Trp Ser Cys Ile Ile Leu Phe Leu Val Ala Thr Ala Thr Gly
1               5                   10                  15

Val His Ser Asp Ile Gln Leu Thr Gln Ser Pro Ser Ser Leu Ser Ala
            20                  25                  30

Ser Val Gly Asp Arg Val Thr Ile Thr Cys Lys Ser Ser Gln Ser Val
        35                  40                  45

Leu Tyr Ser Ser Asn Gln Lys Asn Tyr Leu Ala Trp Tyr Gln Gln Lys
    50                  55                  60

Pro Gly Lys Ala Pro Lys Leu Leu Ile Tyr Trp Ala Ser Thr Arg Glu
65                  70                  75                  80

Ser Gly Val Pro Ser Arg Phe Ser Gly Ser Gly Ser Gly Thr Asp Phe
                85                  90                  95

Thr Phe Thr Ile Ser Ser Leu Gln Pro Glu Asp Ile Ala Thr Tyr Tyr
            100                 105                 110

Cys His Gln Tyr Leu Ser Ser Trp Thr Phe Gly Gln Gly Thr Lys Val
        115                 120                 125

Glu Ile Lys Ser Ser Gly Gly Gly Gly Ser Gly Gly Gly Gly Ser Gly
    130                 135                 140

Gly Gly Gly Ser Glu Val Gln Leu Val Glu Ser Gly Gly Gly Val Val
145                 150                 155                 160

Gln Pro Gly Arg Ser Leu Arg Leu Ser Cys Ser Ser Ser Gly Phe Ile
                165                 170                 175

Phe Ser Asp Asn Tyr Met Tyr Trp Val Arg Gln Ala Pro Gly Lys Gly
            180                 185                 190

Leu Glu Trp Val Ala Thr Ile Ser Asp Gly Gly Ser Tyr Thr Tyr Tyr
        195                 200                 205

Pro Asp Ser Val Lys Gly Arg Phe Thr Ile Ser Arg Asp Asn Ser Lys
    210                 215                 220

Asn Thr Leu Phe Leu Gln Met Asp Ser Leu Arg Pro Glu Asp Thr Gly
225                 230                 235                 240

Val Tyr Phe Cys Ala Arg Gly Tyr Tyr Arg Tyr Glu Gly Ala Met Asp
                245                 250                 255

Tyr Trp Gly Gln Gly Thr Pro Val Thr Val Ser Ser Gly Ser Thr Gly
            260                 265                 270

Gly Gly Gly Ser Thr Ser Ala Gly Gly Gly Gly Ser Ser Asp Ile Gln
        275                 280                 285

Leu Thr Gln Ser Pro Ser Ser Leu Ser Ala Ser Val Gly Asp Arg Val
    290                 295                 300

Thr Ile Thr Cys Lys Ser Ser Gln Ser Val Leu Tyr Ser Ser Asn Gln
305                 310                 315                 320

Lys Asn Tyr Leu Ala Trp Tyr Gln Gln Lys Pro Gly Lys Ala Pro Lys
                325                 330                 335

Leu Leu Ile Tyr Trp Ala Ser Thr Arg Glu Ser Gly Val Pro Ser Arg
            340                 345                 350

Phe Ser Gly Ser Gly Ser Gly Thr Asp Phe Thr Phe Thr Ile Ser Ser
        355                 360                 365

Leu Gln Pro Glu Asp Ile Ala Thr Tyr Tyr Cys His Gln Tyr Leu Ser
    370                 375                 380

Ser Trp Thr Phe Gly Gln Gly Thr Lys Val Glu Ile Lys Ser Ser Gly
385                 390                 395                 400

Gly Gly Gly Ser Gly Gly Gly Gly Ser Gly Gly Gly Gly Ser Glu Val
                405                 410                 415

Gln Leu Val Glu Ser Gly Gly Gly Val Val Gln Pro Gly Arg Ser Leu
```

-continued

```
            420                 425                 430

Arg Leu Ser Cys Ser Ser Ser Gly Phe Ile Phe Ser Asp Asn Tyr Met
        435                 440                 445

Tyr Trp Val Arg Gln Ala Pro Gly Lys Gly Leu Glu Trp Val Ala Thr
    450                 455                 460

Ile Ser Asp Gly Gly Ser Tyr Thr Tyr Tyr Pro Asp Ser Val Lys Gly
465                 470                 475                 480

Arg Phe Thr Ile Ser Arg Asp Asn Ser Lys Asn Thr Leu Phe Leu Gln
                485                 490                 495

Met Asp Ser Leu Arg Pro Glu Asp Thr Gly Val Tyr Phe Cys Ala Arg
            500                 505                 510

Gly Tyr Tyr Arg Tyr Glu Gly Ala Met Asp Tyr Trp Gly Gln Gly Thr
        515                 520                 525

Pro Val Thr Val Ser Ser Gly Ser Thr Gly Gly Gly Gly Ser Thr Ala
    530                 535                 540

Ser Gly Gly Gly Gly Ser Ser Asp Ile Gln Leu Thr Gln Ser Pro Ser
545                 550                 555                 560

Ser Leu Ser Ala Ser Val Gly Asp Arg Val Thr Ile Thr Cys Lys Ser
                565                 570                 575

Ser Gln Ser Val Leu Tyr Ser Ser Asn Gln Lys Asn Tyr Leu Ala Trp
            580                 585                 590

Tyr Gln Gln Lys Pro Gly Lys Ala Pro Lys Leu Leu Ile Tyr Trp Ala
        595                 600                 605

Ser Thr Arg Glu Ser Gly Val Pro Ser Arg Phe Ser Gly Ser Gly Ser
    610                 615                 620

Gly Thr Asp Phe Thr Phe Thr Ile Ser Ser Leu Gln Pro Glu Asp Ile
625                 630                 635                 640

Ala Thr Tyr Tyr Cys His Gln Tyr Leu Ser Ser Trp Thr Phe Gly Gln
                645                 650                 655

Gly Thr Lys Val Glu Ile Lys Ser Ser Gly Gly Gly Gly Ser Gly Gly
            660                 665                 670

Gly Gly Ser Gly Gly Gly Gly Ser Glu Val Gln Leu Val Glu Ser Gly
        675                 680                 685

Gly Gly Val Val Gln Pro Gly Arg Ser Leu Arg Leu Ser Cys Ser Ser
    690                 695                 700

Ser Gly Phe Ile Phe Ser Asp Asn Tyr Met Tyr Trp Val Arg Gln Ala
705                 710                 715                 720

Pro Gly Lys Gly Leu Glu Trp Val Ala Thr Ile Ser Asp Gly Gly Ser
                725                 730                 735

Tyr Thr Tyr Tyr Pro Asp Ser Val Lys Gly Arg Phe Thr Ile Ser Arg
            740                 745                 750

Asp Asn Ser Lys Asn Thr Leu Phe Leu Gln Met Asp Ser Leu Arg Pro
        755                 760                 765

Glu Asp Thr Gly Val Tyr Phe Cys Ala Arg Gly Tyr Tyr Arg Tyr Glu
    770                 775                 780

Gly Ala Met Asp Tyr Trp Gly Gln Gly Thr Pro Val Thr Val Ser Ser
785                 790                 795                 800

Gly Ser Thr Gly Gly Gly Gly Ser Thr Glu Phe Met Glu Glu Ser Pro
                805                 810                 815

Val Ala Ser Gln Ser Lys Ala Glu Lys Asp Tyr Asp Ala Ala Lys Lys
            820                 825                 830

Asp Ala Lys Asn Ala Lys Lys Ala Val Glu Asp Ala Gln Lys Ala Leu
        835                 840                 845
```

```
Asp Asp Ala Lys Ala Ala Gln Lys Lys Tyr Asp Glu Asp Gln Lys Lys
    850                 855                 860

Thr Glu Glu Lys Ala Ala Leu Glu Lys Ala Ala Ser Glu Glu Met Asp
865                 870                 875                 880

Lys Ala Val Ala Ala Val Gln Gln Ala Tyr Leu Ala Tyr Gln Gln Ala
                885                 890                 895

Thr Asp Lys Ala Ala Lys Asp Ala Ala Asp Lys Met Ile Asp Glu Ala
            900                 905                 910

Lys Lys Arg Glu Glu Glu Ala Lys Thr Lys Phe Asn Thr Val Arg Ala
        915                 920                 925

Met Val Val Pro Glu Pro Glu Gln Leu Ala Glu Thr Lys Lys Lys Ser
    930                 935                 940

Glu Glu Ala Lys Gln Lys Ala Pro Glu Leu Thr Lys Lys Leu Glu Glu
945                 950                 955                 960

Ala Lys Ala Lys Leu Glu Glu Ala Glu Lys Lys Ala Thr Glu Ala Lys
                965                 970                 975

Gln Lys Val Asp Ala Glu Glu Val Ala Pro Gln Ala Lys Ile Ala Glu
            980                 985                 990

Leu Glu Asn Gln Val His Arg Leu  Glu Gln Glu Leu Lys  Glu Ile Asp
        995                 1000                 1005

Glu Ser  Glu Ser Glu Asp Tyr  Ala Lys Glu Gly Phe  Arg Ala Pro
    1010                 1015                 1020

Leu Gln  Ser Lys Leu Asp Ala  Lys Lys Ala Lys Leu  Ser Lys Leu
    1025                 1030                 1035

Glu Glu  Leu Ser Asp Lys Ile  Asp Glu Leu Asp Ala  Glu Ile Ala
    1040                 1045                 1050

Lys Leu  Glu Asp Gln Leu Lys  Ala Ala Glu Glu Asn  Asn Asn Val
    1055                 1060                 1065

Glu Asp  Tyr Phe Lys Glu Gly  Leu Glu Lys Thr Ile  Ala Ala Lys
    1070                 1075                 1080

Lys Ala  Glu Leu Glu Lys Thr  Glu Ala Asp Leu Lys  Lys Ala Val
    1085                 1090                 1095

Asn Glu  Pro Glu Lys Pro Ala  Pro Ala Pro Glu Thr  Pro Ala Pro
    1100                 1105                 1110

Glu Leu  Glu Gly Gly Ser Gly  Gly Cys Thr Leu Glu  Lys Cys Cys
    1115                 1120                 1125

Ala Ala  Ala Asp Pro His Glu  Cys Tyr Ala Lys Val  Phe Asp Glu
    1130                 1135                 1140

Phe Lys  Pro Leu Val Glu Glu  Pro Gln Asn Leu Ile  Lys Gln Asn
    1145                 1150                 1155

Cys Glu  Leu Phe Glu Gln Leu  Gly Glu Tyr Lys Phe  Gln Asn Ala
    1160                 1165                 1170

Leu Leu  Val Arg Tyr Thr Lys  Lys Val Pro Gln Val  Ser Thr Pro
    1175                 1180                 1185

Thr Leu  Val Glu Val Ser Arg  Asn Leu Gly Lys Val  Gly Ser Lys
    1190                 1195                 1200

Cys Cys  Lys His Pro Glu Ala  Lys Arg Met Pro Cys  Ala Glu Asp
    1205                 1210                 1215

Tyr Leu  Ser Val Val Leu Asn  Gln Leu Cys Val Leu  His Glu Lys
    1220                 1225                 1230

Thr Pro  Val Ser Asp Arg Val  Thr Lys Cys Cys Thr  Glu Ser Leu
    1235                 1240                 1245
```

-continued

```
Val Asn  Arg Arg Pro Cys Phe  Ser Ala Leu Glu Val  Asp Glu Thr
    1250                 1255                 1260

Tyr Val  Pro Lys Glu Phe Asn  Ala Glu Thr Phe Thr  Phe His Ala
    1265                 1270                 1275

Asp Ile  Cys Thr Leu Ser Glu  Lys Glu Arg Gln Ile  Lys Lys Gln
    1280                 1285                 1290

Thr Ala  Leu Val Glu Leu Val  Lys His Lys Pro Lys  Ala Thr Lys
    1295                 1300                 1305

Glu Gln  Leu Lys Ala Val Met  Asp Asp Phe Ala Ala  Phe Val Glu
    1310                 1315                 1320

Lys Cys  Cys Lys Ala Asp Asp  Lys Glu Thr Cys Phe  Ala Glu Glu
    1325                 1330                 1335

Gly Lys  Lys Leu Val Ala Ala  Ser Gln Ala Ala Leu  Gly Leu Arg
    1340                 1345                 1350

Thr His  His His His His His  His
    1355                 1360


<210> SEQ ID NO 14
<211> LENGTH: 574
<212> TYPE: PRT
<213> ORGANISM: Artificial sequence
<220> FEATURE:
<223> OTHER INFORMATION: Non-Fc RI targeted PspA-HuSA

<400> SEQUENCE: 14

Met Gly Trp Ser Cys Ile Ile Leu Phe Leu Val Ala Thr Ala Thr Gly
1               5                   10                  15

Gly Gly Gly Ser Thr Ala Ser Glu Phe Met Glu Glu Ser Pro Val Ala
            20                  25                  30

Ser Gln Ser Lys Ala Glu Lys Asp Tyr Asp Ala Ala Lys Lys Asp Ala
        35                  40                  45

Lys Asn Ala Lys Lys Ala Val Glu Asp Ala Gln Lys Ala Leu Asp Asp
    50                  55                  60

Ala Lys Ala Ala Gln Lys Lys Tyr Asp Glu Asp Gln Lys Lys Thr Glu
65                  70                  75                  80

Glu Lys Ala Ala Leu Glu Lys Ala Ala Ser Glu Glu Met Asp Lys Ala
                85                  90                  95

Val Ala Ala Val Gln Gln Ala Tyr Leu Ala Tyr Gln Gln Ala Thr Asp
            100                 105                 110

Lys Ala Ala Lys Asp Ala Ala Asp Lys Met Ile Asp Glu Ala Lys Lys
        115                 120                 125

Arg Glu Glu Glu Ala Lys Thr Lys Phe Asn Thr Val Arg Ala Met Val
    130                 135                 140

Val Pro Glu Pro Glu Gln Leu Ala Glu Thr Lys Lys Lys Ser Glu Glu
145                 150                 155                 160

Ala Lys Gln Lys Ala Pro Glu Leu Thr Lys Lys Leu Glu Glu Ala Lys
                165                 170                 175

Ala Lys Leu Glu Glu Ala Glu Lys Lys Ala Thr Glu Ala Lys Gln Lys
            180                 185                 190

Val Asp Ala Glu Glu Val Ala Pro Gln Ala Lys Ile Ala Glu Leu Glu
        195                 200                 205

Asn Gln Val His Arg Leu Glu Gln Glu Leu Lys Glu Ile Asp Glu Ser
    210                 215                 220

Glu Ser Glu Asp Tyr Ala Lys Glu Gly Phe Arg Ala Pro Leu Gln Ser
225                 230                 235                 240
```

-continued

```
Lys Leu Asp Ala Lys Lys Ala Lys Leu Ser Lys Leu Glu Glu Leu Ser
                245                 250                 255

Asp Lys Ile Asp Glu Leu Asp Ala Glu Ile Ala Lys Leu Glu Asp Gln
            260                 265                 270

Leu Lys Ala Ala Glu Glu Asn Asn Asn Val Glu Asp Tyr Phe Lys Glu
        275                 280                 285

Gly Leu Glu Lys Thr Ile Ala Ala Lys Lys Ala Glu Leu Glu Lys Thr
    290                 295                 300

Glu Ala Asp Leu Lys Lys Ala Val Asn Glu Pro Glu Lys Pro Ala Pro
305                 310                 315                 320

Ala Pro Glu Thr Pro Ala Pro Glu Leu Glu Gly Gly Ser Gly Gly Cys
                325                 330                 335

Thr Leu Glu Lys Cys Cys Ala Ala Ala Asp Pro His Glu Cys Tyr Ala
            340                 345                 350

Lys Val Phe Asp Glu Phe Lys Pro Leu Val Glu Glu Pro Gln Asn Leu
        355                 360                 365

Ile Lys Gln Asn Cys Glu Leu Phe Glu Gln Leu Gly Glu Tyr Lys Phe
    370                 375                 380

Gln Asn Ala Leu Leu Val Arg Tyr Thr Lys Lys Val Pro Gln Val Ser
385                 390                 395                 400

Thr Pro Thr Leu Val Glu Val Ser Arg Asn Leu Gly Lys Val Gly Ser
                405                 410                 415

Lys Cys Cys Lys His Pro Glu Ala Lys Arg Met Pro Cys Ala Glu Asp
            420                 425                 430

Tyr Leu Ser Val Val Leu Asn Gln Leu Cys Val Leu His Glu Lys Thr
        435                 440                 445

Pro Val Ser Asp Arg Val Thr Lys Cys Cys Thr Glu Ser Leu Val Asn
    450                 455                 460

Arg Arg Pro Cys Phe Ser Ala Leu Glu Val Asp Glu Thr Tyr Val Pro
465                 470                 475                 480

Lys Glu Phe Asn Ala Glu Thr Phe Thr Phe His Ala Asp Ile Cys Thr
                485                 490                 495

Leu Ser Glu Lys Glu Arg Gln Ile Lys Lys Gln Thr Ala Leu Val Glu
            500                 505                 510

Leu Val Lys His Lys Pro Lys Ala Thr Lys Glu Gln Leu Lys Ala Val
        515                 520                 525

Met Asp Asp Phe Ala Ala Phe Val Glu Lys Cys Cys Lys Ala Asp Asp
    530                 535                 540

Lys Glu Thr Cys Phe Ala Glu Glu Gly Lys Lys Leu Val Ala Ala Ser
545                 550                 555                 560

Gln Ala Ala Leu Gly Leu Arg Thr His His His His His His
                565                 570
```

<210> SEQ ID NO 15
<211> LENGTH: 2532
<212> TYPE: DNA
<213> ORGANISM: Artificial sequence
<220> FEATURE:
<223> OTHER INFORMATION: anti-human FcgRI-PspA

<400> SEQUENCE: 15

```
atgggatgga gctgtatcat cctcttcttg gtggccacag ctaccggtgt ccactccgat      60

atccagctga cccagagccc aagcagcctg agcgccagcg tgggtgacag agtgaccatc     120

acctgtaagt ccagtcaaag tgttttatac agttcaaatc agaagaacta cttggcctgg     180
```

-continued

```
taccagcaga agccaggtaa ggctccaaag ctgctgatct actgggcatc cactagggaa    240
tctggtgtgc caagcagatt cagcggtagc ggtagcggta ccgacttcac cttcaccatc    300
agcagcctcc agccagagga catcgccacc tactactgcc atcaatacct ctcctcgtgg    360
acgttcggcc aagggaccaa ggtggaaatc aagagctctg gcggtggcgg ctccggaggt    420
ggaggcagcg gagggggtgg atccgaggtc caactggtgg agagcggtgg aggtgttgtg    480
caacctggcc ggtccctgcg cctgtcctgc tcctcgtctg gcttcatttt cagtgacaat    540
tacatgtatt gggtgagaca ggcacctgga aaaggtcttg agtgggttgc aaccattagt    600
gatggtggta gttacaccta ctatccagac agtgtgaagg gaagatttac aatatcgaga    660
gacaacagca agaacacatt gttcctgcaa atggacagcc tgagacccga agacaccggg    720
gtctattttt gtgcaagagg ctactatagg tacgaggggg ctatggacta ctggggccaa    780
gggaccccgg tcaccgtctc ctcaggctcg accggtgggg gaggctcgac cggaggcgga    840
ggttctagtg acatccagct gacccagagc ccaagcagcc tgagcgccag cgtgggtgac    900
agagtgacca tcacctgtaa gtccagtcaa agtgttttat acagttcaaa tcagaagaac    960
tacttggcct ggtaccagca gaagccaggt aaggctccaa agctgctgat ctactgggca   1020
tccactaggg aatctggtgt gccaagcaga ttcagcggta gcggtagcgg taccgacttc   1080
accttcacca tcagcagcct ccagccagag gacatcgcca cctactactg ccatcaatac   1140
ctctcctcgt ggacgttcgg ccaagggacc aaggtggaaa tcaagagctc tggcggtggc   1200
ggctccggag gtggaggcag cggagggggt ggatccgagg tccaactggt ggagagcggt   1260
ggaggtgttg tgcaacctgg ccggtccctg cgcctgtcct gctcctcgtc tggcttcatt   1320
ttcagtgaca attacatgta ttgggtgaga caggcacctg gaaaaggtct tgagtgggtt   1380
gcaaccatta gtgatggtgg tagttacacc tactatccag acagtgtgaa gggaagattt   1440
acaatatcga gagacaacag caagaacaca ttgttcctgc aaatggacag cctgagaccc   1500
gaagacaccg gggtctattt ttgtgcaaga ggctactata ggtacgaggg ggctatggac   1560
tactggggcc aagggacccc ggtcaccgtc tcctcaggct cgaccggtgg gggagggtcg   1620
actatggaag aatctcccgt agccagtcag tctaaagctg agaaagacta tgatgcagcg   1680
aagaaagatg ctaagaatgc gaaaaaagca gtagaagatg ctcaaaaggc tttagatgat   1740
gcaaaagctg ctcagaaaaa atatgacgag gatcagaaga aaactgagga gaaagccgcg   1800
ctagaaaaag cagcgtctga agagatggat aaggcagtgg cagcagttca acaagcgtat   1860
ctagcctatc aacaagctac agacaaagcc gcaaaagacg cagcagataa gatgatagat   1920
gaagctaaga aacgcgaaga agaggcaaaa actaaattta atactgttcg agcaatggta   1980
gttcctgagc cagagcagtt ggctgagact aagaaaaaat cagaagaagc taaacaaaaa   2040
gcaccagaac ttactaaaaa actagaagaa gctaaagcaa aattagaaga ggctgagaaa   2100
aaagctactg aagccaaaca aaaagtggat gctgaagaag tcgctcctca agctaaaatc   2160
gctgaattgg aaaatcaagt tcatagacta gaacaagagc tcaaagagat tgatgagtct   2220
gaatcagaag attatgctaa agaaggtttc cgtgctcctc ttcaatctaa attggatgcc   2280
aaaaaagcta aactatcaaa acttgaagag ttaagtgata agattgatga gttagacgct   2340
gaaattgcaa aacttgaaga tcaacttaaa gctgctgaag aaaacaataa tgtagaagac   2400
tactttaaag aaggtttaga gaaaactatt gctgctaaaa aagctgaatt agaaaaaact   2460
gaagctgacc ttaagaaagc agttaatgag ccagaaaaac cagctccagc tccagaaact   2520
ccagccccag aa                                                        2532
```

<210> SEQ ID NO 16
<211> LENGTH: 906
<212> TYPE: DNA
<213> ORGANISM: Artificial sequence
<220> FEATURE:
<223> OTHER INFORMATION: PspA antigen

<400> SEQUENCE: 16
gaagaatctc ccgtagccag tcagtctaaa gctgagaaag actatgatgc agcgaagaaa 60
gatgctaaga atgcgaaaaa agcagtagaa gatgctcaaa aggctttaga tgatgcaaaa 120
gctgctcaga aaaaatatga cgaggatcag aagaaaactg aggagaaagc cgcgctagaa 180
aaagcagcgt ctgaagagat ggataaggca gtggcagcag ttcaacaagc gtatctagcc 240
tatcaacaag ctacagacaa agccgcaaaa gacgcagcag ataagatgat agatgaagct 300
aagaaacgcg aagaagaggc aaaaactaaa tttaatactg ttcgagcaat ggtagttcct 360
gagccagagc agttggctga gactaagaaa aaatcagaag aagctaaaca aaaagcacca 420
gaacttacta aaaaactaga agaagctaaa gcaaaattag aagaggctga gaaaaaagct 480
actgaagcca aacaaaaagt ggatgctgaa gaagtcgctc ctcaagctaa aatcgctgaa 540
ttggaaaatc aagttcatag actagaacaa gagctcaaag agattgatga gtctgaatca 600
gaagattatg ctaaagaagg tttccgtgct cctcttcaat ctaaattgga tgccaaaaaa 660
gctaaactat caaaacttga agagttaagt gataagattg atgagttaga cgctgaaatt 720
gcaaaacttg aagatcaact taaagctgct gaagaaaaca ataatgtaga agactacttt 780
aaagaaggtt tagagaaaac tattgctgct aaaaaagctg aattagaaaa aactgaagct 840
gaccttaaga aagcagttaa tgagccagaa aaaccagctc cagctccaga aactccagcc 900
ccagaa 906

<210> SEQ ID NO 17
<211> LENGTH: 4064
<212> TYPE: DNA
<213> ORGANISM: Artificial sequence
<220> FEATURE:
<223> OTHER INFORMATION: pUW160s

<400> SEQUENCE: 17
gggggggggg ggcgctgagg tctgcctcgt gaagaaggtg ttgctgactc ataccaggcc 60
tgaatcgccc catcatccag ccagaaagtg agggagccac ggttgatgag agctttgttg 120
taggtggacc agttggtgat tttgaacttt tgctttgcca cggaacggtc tgcgttgtcg 180
ggaagatgcg tgatctgatc cttcaactca gcaaaagttc gatttattca acaaagccgc 240
cgtcccgtca agtcagcgta atgctctgcc agtgttacaa ccaattaacc aattctgatt 300
agaaaaactc atcgagcatc aaatgaaact gcaatttatt catatcagga ttatcaatac 360
catatttttg aaaaagccgt ttctgtaatg aaggagaaaa ctcaccgagg cagttccata 420
ggatggcaag atcctggtat cggtctgcga ttccgactcg tccaacatca atacaaccta 480
ttaatttccc ctcgtcaaaa ataaggttat caagtgagaa atcaccatga gtgacgactg 540
aatccggtga gaatggcaaa agcttatgca tttctttcca gacttgttca acaggccagc 600
cattacgctc gtcatcaaaa tcactcgcat caaccaaacc gttattcatt cgtgattgcg 660
cctgagcgag acgaaatacg cgatcgctgt taaaaggaca attacaaaca ggaatcgaat 720
gcaaccggcg caggaacact gccagcgcat caacaatatt ttcacctgaa tcaggatatt 780

```
cttctaatac ctggaatgct gttttcccgg ggatcgcagt ggtgagtaac catgcatcat    840
caggagtacg gataaaatgc ttgatggtcg gaagaggcat aaattccgtc agccagttta    900
gtctgaccat ctcatctgta acatcattgg caacgctacc tttgccatgt ttcagaaaca    960
actctggcgc atcgggcttc ccatacaatc gatagattgt cgcacctgat tgcccgacat   1020
tatcgcgagc ccatttatac ccatataaat cagcatccat gttggaattt aatcgcggcc   1080
tcgagcaaga cgtttcccgt tgaatatggc tcataacacc ccttgtatta ctgtttatgt   1140
aagcagacag gtcgacaata ttggctattg gccattgcat acgttgtatc tatatcataa   1200
tatgtacatt tatattggct catgtccaat atgaccgcca tgttgacatt gattattgac   1260
tagttattaa tagtaatcaa ttacggggtc attagttcat agcccatata tggagttccg   1320
cgttacataa cttacggtaa atggcccgcc tggctgaccg cccaacgacc cccgcccatt   1380
gacgtcaata atgacgtatg ttcccatagt aacgccaata gggactttcc attgacgtca   1440
atgggtggag tatttacggt aaactgccca cttggcagta catcaagtgt atcatatgcc   1500
aagtccgccc cctattgacg tcaatgacgg taaatggccc gcctggcatt atgcccagta   1560
catgacctta cgggactttc ctacttggca gtacatctac gtattagtca tcgctattac   1620
catggtgatg cggttttggc agtacaccaa tgggcgtgga tagcggtttg actcacgggg   1680
atttccaagt ctccacccca ttgacgtcaa tgggagtttg ttttggcacc aaaatcaacg   1740
ggactttcca aaatgtcgta ataaccccgc cccgttgacg caaatgggcg gtaggcgtgt   1800
acggtgggag gtctatataa gcagagctcg tttagtgaac cgtcagatcg cctggagacg   1860
ccatccacgc tgttttgacc tccatagaag acaccgggac cgatccagcc tccgcggccg   1920
ggaacggtgc attggaacgc ggattccccg tgccaagagt gactcaccgt ccggatctca   1980
gcaagcaggt atgtactctc cagggtgggc ctggcttccc cagtcaagac tccagggatt   2040
tgagggacgc tgtgggctct tctcttacat gtaccttttg cttgcctcaa ccctgactat   2100
cttccaggtc aggatcccag agtcaggggt ctgtattttc ctgctggtgg ctccagttca   2160
ggaacagtaa accctgctcc gaatattgcc tctcacatct cgtcaatctc cgcgaggact   2220
ggggaccctg tgacgaacat ggctagtagg tctttgctaa tcttggtgct ttgcttcctg   2280
cccctggctg ctctgggggc tagcagatct gggccctaac aaaacaaaaa gatggggtta   2340
ttccctaaac ttcatgggtt acgtaattgg aagttggggg acattgccac aagatcatat   2400
tgtacaaaag atcaaacact gttttagaaa acttcctgta aacaggccta ttgattggaa   2460
agtatgtcaa aggattgtgg gtcttttggg ctttgctgct ccatttacac aatgtggata   2520
tcctgcctta atgcctttgt atgcatgtat acaagctaaa caggctttca ctttctcgcc   2580
aacttacaag gcctttctaa gtaaacagta catgaacctt taccccgttg ctcggcaacg   2640
gcctggtctg tgccaagtgt ttgctgacgc aacccccact ggctggggct tggccatagg   2700
ccatcagcgc atgcgtggaa cctttgtggc tcctctgccg atccatactg cggaactcct   2760
agccgcttgt tttgctcgca gccggtctgg agcaaagctc ataggaactg acaattctgt   2820
cgtcctctcg cggaaatata catcgtttcg atctacgtat gatctttttc cctctgccaa   2880
aaattatggg gacatcatga agccccttga gcatctgact tctggctaat aaaggaaatt   2940
tattttcatt gcaatagtgt gttggaattt tttgtgtctc tcactcggaa ggaattctgc   3000
attaatgaat cggccaacgc gcggggagag gcggtttgcg tattgggcgc tcttccgctt   3060
cctcgctcac tgactcgctg cgctcggtcg ttcggctgcg gcgagcggta tcagctcact   3120
caaaggcggt aatacggtta tccacagaat caggggataa cgcaggaaag aacatgtgag   3180
```

-continued

```
caaaaggcca gcaaaaggcc aggaaccgta aaaaggccgc gttgctggcg tttttccata   3240

ggctccgccc ccctgacgag catcacaaaa atcgacgctc aagtcagagg tggcgaaacc   3300

cgacaggact ataaagatac caggcgtttc cccctggaag ctccctcgtg cgctctcctg   3360

ttccgaccct gccgcttacc ggatacctgt ccgcctttct cccttcggga agcgtggcgc   3420

tttctcatag ctcacgctgt aggtatctca gttcggtgta ggtcgttcgc tccaagctgg   3480

gctgtgtgca cgaacccccc gttcagcccg accgctgcgc cttatccggt aactatcgtc   3540

ttgagtccaa cccggtaaga cacgacttat cgccactggc agcagccact ggtaacagga   3600

ttagcagagc gaggtatgta ggcggtgcta cagagttctt gaagtggtgg cctaactacg   3660

gctacactag aagaacagta tttggtatct gcgctctgct gaagccagtt accttcggaa   3720

aaagagttgg tagctcttga tccggcaaac aaaccaccgc tggtagcggt ggtttttttg   3780

tttgcaagca gcagattacg cgcagaaaaa aaggatctca agaagatcct ttgatctttt   3840

ctacggggtc tgacgctcag tggaacgaaa actcacgtta agggattttg gtcatgagat   3900

tatcaaaaag gatcttcacc tagatccttt taaattaaaa atgaagtttt aaatcaatct   3960

aaagtatata tgagtaaact tggtctgaca gttaccaatg cttaatcagt gaggcaccta   4020

tctcagcgat ctgtctattt cgttcatcca tagttgcctg actc                    4064
```

<210> SEQ ID NO 18
<211> LENGTH: 3753
<212> TYPE: DNA
<213> ORGANISM: Artificial sequence
<220> FEATURE:
<223> OTHER INFORMATION: pJV7563

<400> SEQUENCE: 18

```
ggcgtaatgc tctgccagtg ttacaaccaa ttaaccaatt ctgattagaa aaactcatcg     60

agcatcaaat gaaactgcaa tttattcata tcaggattat caataccata tttttgaaaa    120

agccgtttct gtaatgaagg agaaaactca ccgaggcagt tccataggat ggcaagatcc    180

tggtatcggt ctgcgattcc gactcgtcca acatcaatac aacctattaa tttcccctcg    240

tcaaaaataa ggttatcaag tgagaaatca ccatgagtga cgactgaatc cggtgagaat    300

ggcaaaagct tatgcatttc tttccagact tgttcaacag gccagccatt acgctcgtca    360

tcaaaatcac tcgcatcaac caaaccgtta ttcattcgtg attgcgcctg agcgagacga    420

aatacgcgat cgctgttaaa aggacaatta caaacaggaa tcaaatgcaa ccggcgcagg    480

aacactgcca gcgcatcaac aatattttca cctgaatcag gatattcttc taatacctgg    540

aatgctgttt tcccggggat cgcagtggtg agtaaccatg catcatcagg agtacggata    600

aaatgcttga tggtcggaag aggcataaat tccgtcagcc agtttagtct gaccatctca    660

tctgtaacat cattggcaac gctacctttg ccatgtttca gaaacaactc tggcgcatcg    720

ggcttcccat acaatcgata gattgtcgca cctgattgcc cgacattatc gcgagcccat    780

ttatacccat ataaatcagc atccatgttg gaatttaatc gcggcctcga gcaagacgtt    840

tcccgttgaa tatggctcat aacacccctt gtattactgt ttatgtaagc agacaggtcg    900

acaatattgg ctattggcca ttgcatacgt tgtatctata tcataatatg tacatttata    960

ttggctcatg tccaatatga ccgccatgtt gacattgatt attgactagt tattaatagt   1020

aatcaattac ggggtcatta gttcatagcc catatatgga gttccgcgtt acataactta   1080

cggtaaatgg cccgcctggc tgaccgccca acgacccccg cccattgacg tcaataatga   1140
```

-continued

```
cgtatgttcc catagtaacg ccaataggga ctttccattg acgtcaatgg gtggagtatt   1200
tacggtaaac tgcccacttg gcagtacatc aagtgtatca tatgccaagt ccgcccccta   1260
ttgacgtcaa tgacggtaaa tggcccgcct ggcattatgc ccagtacatg accttacggg   1320
actttcctac ttggcagtac atctacgtat tagtcatcgc tattaccatg gtgatgcggt   1380
tttggcagta caccaatggg cgtggatagc ggtttgactc acggggattt ccaagtctcc   1440
accccattga cgtcaatggg agtttgtttt ggcaccaaaa tcaacgggac tttccaaaat   1500
gtcgtaataa ccccgccccg ttgacgcaaa tgggcggtag gcgtgtacgg tgggaggtct   1560
atataagcag agctcgttta gtgaaccgtc agatcgcctg gagacgccat ccacgctgtt   1620
ttgacctcca tagaagacac cgggaccgat ccagcctccg cggccgggaa cggtgcattg   1680
gaacgcggat tccccgtgcc aagagtgact caccgtccgg atctcagcaa gcaggtatgt   1740
actctccagg gtgggcctgg cttccccagt caagactcca gggatttgag ggacgctgtg   1800
ggctcttctc ttacatgtac cttttgcttg cctcaaccct gactatcttc caggtcagga   1860
tcccagagtc aggggtctgt attttcctgc tggtggctcc agttcaggaa cagtaaaccc   1920
tgctccgaat attgcctctc acatctcgtc aatctccgcg aggactgggg accctgtgac   1980
gaacatggct agcagatctg ggccctaaca aaacaaaaag atggggttat tccctaaact   2040
tcatgggtta cgtaattgga agttggggga cattgccaca agatcatatt gtacaaaaga   2100
tcaaacactg ttttagaaaa cttcctgtaa acaggcctat tgattggaaa gtatgtcaaa   2160
ggattgtggg tcttttgggc tttgctgctc catttacaca atgtggatat cctgccttaa   2220
tgcctttgta tgcatgtata caagctaaac aggctttcac tttctcgcca acttacaagg   2280
cctttctaag taaacagtac atgaaccttt accccgttgc tcggcaacgg cctggtctgt   2340
gccaagtgtt tgctgacgca acccccactg gctggggctt ggccataggc catcagcgca   2400
tgcgtggaac ctttgtggct cctctgccga tccatactgc ggaactccta gccgcttgtt   2460
ttgctcgcag ccggtctgga gcaaagctca taggaactga caattctgtc gtcctctcgc   2520
ggaaatatac atcgtttcga tctacgtatg atctttttcc ctctgccaaa aattatgggg   2580
acatcatgaa gccccttgag catctgactt ctggctaata aaggaaattt attttcattg   2640
caatagtgtg ttggaatttt ttgtgtctct cactcggaag gaattctgca ttaatgaatc   2700
ggccaacgcg cggggagagg cggtttgcgt attgggcgct cttccgcttc ctcgctcact   2760
gactcgctgc gctcggtcgt tcggctgcgg cgagcggtat cagctcactc aaaggcggta   2820
atacggttat ccacagaatc aggggataac gcaggaaaga acatgtgagc aaaaggccag   2880
caaaaggcca ggaaccgtaa aaaggccgcg ttgctggcgt ttttccatag gctccgcccc   2940
cctgacgagc atcacaaaaa tcgacgctca agtcagaggt ggcgaaaccc gacaggacta   3000
taaagatacc aggcgtttcc ccctggaagc tccctcgtgc gctctcctgt tccgaccctg   3060
ccgcttaccg gatacctgtc cgcctttctc ccttcgggaa gcgtggcgct ttctcatagc   3120
tcacgctgta ggtatctcag ttcggtgtag gtcgttcgct ccaagctggg ctgtgtgcac   3180
gaaccccccg ttcagcccga ccgctgcgcc ttatccggta actatcgtct tgagtccaac   3240
ccggtaagac acgacttatc gccactggca gcagccactg gtaacaggat tagcagagcg   3300
aggtatgtag gcggtgctac agagttcttg aagtggtggc ctaactacgg ctacactaga   3360
agaacagtat ttggtatctg cgctctgctg aagccagtta ccttcggaaa aagagttggt   3420
agctcttgat ccggcaaaca aaccaccgct ggtagcggtg gtttttttgt ttgcaagcag   3480
cagattacgc gcagaaaaaa aggatctcaa gaagatcctt tgatcttttc tacggggtct   3540
```

gacgctcagt ggaacgaaaa ctcacgttaa gggattttgg tcatgagatt atcaaaaagg 3600
atcttcacct agatcctttt aaattaaaaa tgaagtttta aatcaatcta aagtatatat 3660
gagtaaactt ggtctgacag ttaccaatgc ttaatcagtg aggcacctat ctcagcgatc 3720
tgtctatttc gttcatccat agttgcctga ctc 3753

<210> SEQ ID NO 19
<211> LENGTH: 8912
<212> TYPE: DNA
<213> ORGANISM: Artificial sequence
<220> FEATURE:
<223> OTHER INFORMATION: Trivalent anti-FcgR1-PspA

<400> SEQUENCE: 19
acggatcggg agatctcccg atcccctatg gtcgactctc agtacaatct gctctgatgc 60
cgcatagtta agccagtatc tgctccctgc ttgtgtgttg gaggtcgctg agtagtgcgc 120
gagcaaaatt taagctacaa caaggcaagg cttgaccgac aattgcatga agaatctgct 180
tagggttagg cgttttgcgc tgcttcgcga tgtacgggcc agatatacgc gttgacattg 240
attattgact agttattaat agtaatcaat tacggggtca ttagttcata gcccatatat 300
ggagttccgc gttacataac ttacggtaaa tggcccgcct ggctgaccgc ccaacgaccc 360
ccgcccattg acgtcaataa tgacgtatgt tcccatagta acgccaatag ggactttcca 420
ttgacgtcaa tgggtggact atttacggta aactgcccac ttggcagtac atcaagtgta 480
tcatatgcca agtacgcccc ctattgacgt caatgacggt aaatggcccg cctggcatta 540
tgcccagtac atgaccttat gggactttcc tacttggcag tacatctacg tattagtcat 600
cgctattacc atggtgatgc ggttttggca gtacatcaat gggcgtggat agcggtttga 660
ctcacgggga tttccaagtc tccaccccat tgacgtcaat gggagtttgt tttggcacca 720
aaatcaacgg gactttccaa aatgtcgtaa caactccgcc ccattgacgc aaatgggcgg 780
taggcgtgta cggtgggagg tctatataag cagagctctc tggctaacta gagaacccac 840
tgcttactgg cttatcgaaa ttaatacgac tcactatagg gagacccaag cttcaccatg 900
ggatggagct gtatcatcct cttcttggtg gccacagcta ccggtgtcca ctccgatatc 960
cagctgaccc agagcccaag cagcctgagc gccagcgtgg gtgacagagt gaccatcacc 1020
tgtaagtcca gtcaaagtgt tttatacagt tcaaatcaga agaactactt ggcctggtac 1080
cagcagaagc caggtaaggc tccaaagctg ctgatctact gggcatccac tagggaatct 1140
ggtgtgccaa gcagattcag cggtagcggt agcggtaccg acttcacctt caccatcagc 1200
agcctccagc cagaggacat cgccacctac tactgccatc aatacctctc ctcgtggacg 1260
ttcggccaag ggaccaaggt ggaaatcaag agctctggcg gtggcggctc cggaggtgga 1320
ggcagcggag ggggtggatc cgaggtccaa ctggtggaga gcggtggagg tgttgtgcaa 1380
cctggccggt ccctgcgcct gtcctgctcc tcgtctggct tcattttcag tgacaattac 1440
atgtattggg tgagacaggc acctggaaaa ggtcttgagt gggttgcaac cattagtgat 1500
ggtggtagtt acacctacta tccagacagt gtgaagggaa gatttacaat atcgagagac 1560
aacagcaaga acacattgtt cctgcaaatg gacagcctga gacccgaaga caccggggtc 1620
tatttttgtg caagaggcta ctataggtac gagggggcta tggactactg gggccaaggg 1680
accccggtca ccgtctcctc aggctcgacc ggtgggggag gctcgaccag cgctggaggc 1740
ggaggttcta gtgacatcca gctgacccag agcccaagca gcctgagcgc cagcgtgggt 1800

-continued

```
gacagagtga ccatcacctg taagtccagt caaagtgttt tatacagttc aaatcagaag   1860
aactacttgg cctggtacca gcagaagcca ggtaaggctc caaagctgct gatctactgg   1920
gcatccacta gggaatctgg tgtgccaagc agattcagcg gtagcggtag cggtaccgac   1980
ttcaccttca ccatcagcag cctccagcca gaggacatcg ccacctacta ctgccatcaa   2040
tacctctcct cgtggacgtt cggccaaggg accaaggtgg aaatcaagag ctctggcggt   2100
ggcggctccg gaggtggagg cagcggaggg ggtggatccg aggtccaact ggtggagagc   2160
ggtggaggtg ttgtgcaacc tggccggtcc ctgcgcctgt cctgctcctc gtctggcttc   2220
attttcagtg acaattacat gtattgggtg agacaggcac ctggaaaagg tcttgagtgg   2280
gttgcaacca ttagtgatgg tggtagttac acctactatc cagacagtgt gaagggaaga   2340
tttacaatat cgagagacaa cagcaagaac acattgttcc tgcaaatgga cagcctgaga   2400
cccgaagaca ccggggtcta tttttgtgca agaggctact ataggtacga gggggctatg   2460
gactactggg gccaagggac cccggtcacc gtctcctcag gctcgaccgg tgggggaggg   2520
tcgactgcta gcggaggcgg aggttctagt gacatccagc tgacccagag cccaagcagc   2580
ctgagcgcca gcgtgggtga cagagtgacc atcacctgta agtccagtca aagtgtttta   2640
tacagttcaa atcagaagaa ctacttggcc tggtaccagc agaagccagg taaggctcca   2700
aagctgctga tctactgggc atccactagg gaatctggtg tgccaagcag attcagcggt   2760
agcggtagcg gtaccgactt caccttcacc atcagcagcc tccagccaga ggacatcgcc   2820
acctactact gccatcaata cctctcctcg tggacgttcg gccaagggac caaggtggaa   2880
atcaagagct ctggcggtgg cggctccgga ggtggaggca gcggaggggg tggatccgag   2940
gtccaactgg tggagagcgg tggaggtgtt gtgcaacctg gccggtccct gcgcctgtcc   3000
tgctcctcgt ctggcttcat tttcagtgac aattacatgt attgggtgag acaggcacct   3060
ggaaaaggtc ttgagtgggt tgcaaccatt agtgatggtg gtagttacac ctactatcca   3120
gacagtgtga agggaagatt tacaatatcg agagacaaca gcaagaacac attgttcctg   3180
caaatggaca gcctgagacc cgaagacacc ggggtctatt tttgtgcaag aggctactat   3240
aggtacgagg gggctatgga ctactggggc caagggaccc cggtcaccgt ctcctcaggc   3300
tcgaccggtg gggggagggtc gactgaattc atggaagaat ctcccgtagc cagtcagtct   3360
aaagctgaga aagactatga tgcagcgaag aaagatgcta agaatgcgaa aaaagcagta   3420
gaagatgctc aaaaggcttt agatgatgca aaagctgctc agaaaaaata tgacgaggat   3480
cagaagaaaa ctgaggagaa agccgcgcta gaaaaagcag cgtctgaaga gatggataag   3540
gcagtggcag cagttcaaca agcgtatcta gcctatcaac aagctacaga caaagccgca   3600
aaagacgcag cagataagat gatagatgaa gctaagaaac gcgaagaaga ggcaaaaact   3660
aaatttaata ctgttcgagc aatggtagtt cctgagccag agcagttggc tgagactaag   3720
aaaaaatcag aagaagctaa acaaaaagca ccagaactta ctaaaaaact agaagaagct   3780
aaagcaaaat tagaagaggc tgagaaaaaa gctactgaag ccaaacaaaa agtggatgct   3840
gaagaagtcg ctcctcaagc taaaatcgct gaattggaaa atcaagttca tagactagaa   3900
caagagctca aagagattga tgagtctgaa tcagaagatt atgctaaaga aggtttccgt   3960
gctcctcttc aatctaaatt ggatgccaaa aaagctaaac tatcaaaact tgaagagtta   4020
agtgataaga ttgatgagtt agacgctgaa attgcaaaac ttgaagatca acttaaagct   4080
gctgaagaaa acaataatgt agaagactac tttaaagaag gtttagagaa aactattgct   4140
gctaaaaaag ctgaattaga aaaaactgaa gctgacctta agaaagcagt taatgagcca   4200
```

```
gaaaaaccag ctccagctcc agaaactcca gccccagaac tcgagcacca ccaccaccac   4260
cactgagatc cggctgctaa caaagcccga aaggaagctg agttggctgc tgccaccgct   4320
gagcaataac tagcataacc ccttggggcc tctaaacggg tcttgagggg ttttgcggcc   4380
gcacgacaga aactcatctc agaagaggat ctgaatggcg ccgcacatca ccatcatcac   4440
cattgattct agagggccct attctatagt gtcacctaaa tgctagagct cgctgatcag   4500
cctcgactgt gccttctagt tgccagccat ctgttgtttg cccctccccc gtgccttcct   4560
tgaccctgga aggtgccact cccactgtcc tttcctaata aaatgaggaa attgcatcgc   4620
attgtctgag taggtgtcat tctattctgg ggggtggggt ggggcaggac agcaaggggg   4680
aggattggga agacaatagc aggcatgctg gggatgcggt gggctctatg gcttctgagg   4740
cggaaagaac cagctggggc tctagggggt atccccacgc gccctgtagc ggcgcattaa   4800
gcgcggcggg tgtggtggtt acgcgcagcg tgaccgctac acttgccagc gccctagcgc   4860
ccgctccttt cgctttcttc ccttcctttc tcgccacgtt cgccggcttt ccccgtcaag   4920
ctctaaatcg ggcatccct ttagggttcc gatttagtgc tttacggcac ctcgacccca    4980
aaaaacttga ttagggtgat ggttcacgta gtgggccatc gccctgatag acggtttttc   5040
gccctttgac gttggagtcc acgttcttta atagtggact cttgttccaa actggaacaa   5100
cactcaaccc tatctcggtc tattcttttg atttataagg gattttgggg atttcggcct   5160
attggttaaa aaatgagctg atttaacaaa aatttaacgc gaattaattc tgtggaatgt   5220
gtgtcagtta gggtgtggaa agtccccagg ctccccaggc aggcagaagt atgcaaagca   5280
tgcatctcaa ttagtcagca accaggtgtg gaaagtcccc aggctcccca gcaggcagaa   5340
gtatgcaaag catgcatctc aattagtcag caaccatagt cccgccccta actccgccca   5400
tcccgcccct aactccgccc agttccgccc attctccgcc ccatggctga ctaatttttt   5460
ttatttatgc agaggccgag gccgcctctg cctctgagct attccagaag tagtgaggag   5520
gcttttttgg aggcctaggc ttttgcaaaa agctcccggg agcttgtata tccattttcg   5580
gatctgatca agagacagga tgaggatcgt ttcgcatgat tgaacaagat ggattgcacg   5640
caggttctcc ggccgcttgg gtggagaggc tattcggcta tgactgggca caacagacaa   5700
tcggctgctc tgatgccgcc gtgttccggc tgtcagcgca ggggcgcccg gttctttttg   5760
tcaagaccga cctgtccggt gccctgaatg aactgcagga cgaggcagcg cggctatcgt   5820
ggctggccac gacgggcgtt ccttgcgcag ctgtgctcga cgttgtcact gaagcgggaa   5880
gggactggct gctattgggc gaagtgccgg ggcaggatct cctgtcatct caccttgctc   5940
ctgccgagaa agtatccatc atggctgatg caatgcggcg gctgcatacg cttgatccgg   6000
ctacctgccc attcgaccac caagcgaaac atcgcatcga gcgagcacgt actcggatgg   6060
aagccggtct tgtcgatcag gatgatctgg acgaagagca tcaggggctc gcgccagccg   6120
aactgttcgc caggctcaag gcgcgcatgc ccgacggcga ggatctcgtc gtgacccatg   6180
gcgatgcctg cttgccgaat atcatggtgg aaaatggccg cttttctgga ttcatcgact   6240
gtggccggct gggtgtggcg gaccgctatc aggacatagc gttggctacc cgtgatattg   6300
ctgaagagct tggcggcgaa tgggctgacc gcttcctcgt gctttacggt atcgccgctc   6360
ccgattcgca gcgcatcgcc ttctatcgcc ttcttgacga gttcttctga gcgggactct   6420
ggggttcgaa atgaccgacc aagcgacgcc caacctgcca tcacgagatt tcgattccac   6480
cgccgccttc tatgaaaggt tgggcttcgg aatcgttttc cgggacgccg gctggatgat   6540
```

-continued

```
cctccagcgc ggggatctca tgctggagtt cttcgcccac cccaacttgt ttattgcagc   6600
ttataatggt tacaaataaa gcaatagcat cacaaatttc acaaataaag catttttttc   6660
actgcattct agttgtggtt tgtccaaact catcaatgta tcttatcatg tctgtatacc   6720
gtcgacctct agctagagct tggcgtaatc atggtcatag ctgtttcctg tgtgaaattg   6780
ttatccgctc acaattccac acaacatacg agccggaagc ataaagtgta aagcctgggg   6840
tgcctaatga gtgagctaac tcacattaat tgcgttgcgc tcactgcccg ctttccagtc   6900
gggaaacctg tcgtgccagc tgcattaatg aatcggccaa cgcgcgggga gaggcggttt   6960
gcgtattggg cgctcttccg cttcctcgct cactgactcg ctgcgctcgg tcgttcggct   7020
gcggcgagcg gtatcagctc actcaaaggc ggtaatacgg ttatccacag aatcagggga   7080
taacgcagga aagaacatgt gagcaaaagg ccagcaaaag gccaggaacc gtaaaaaggc   7140
cgcgttgctg gcgtttttcc ataggctccg cccccctgac gagcatcaca aaaatcgacg   7200
ctcaagtcag aggtggcgaa acccgacagg actataaaga taccaggcgt ttccccctgg   7260
aagctccctc gtgcgctctc ctgttccgac cctgccgctt accggatacc tgtccgcctt   7320
tctcccttcg ggaagcgtgg cgctttctca atgctcacgc tgtaggtatc tcagttcggt   7380
gtaggtcgtt cgctccaagc tgggctgtgt gcacgaaccc cccgttcagc ccgaccgctg   7440
cgccttatcc ggtaactatc gtcttgagtc caacccggta agacacgact tatcgccact   7500
ggcagcagcc actggtaaca ggattagcag agcgaggtat gtaggcggtg ctacagagtt   7560
cttgaagtgg tggcctaact acggctacac tagaaggaca gtatttggta tctgcgctct   7620
gctgaagcca gttaccttcg gaaaaagagt tggtagctct tgatccggca aacaaaccac   7680
cgctggtagc ggtggttttt ttgtttgcaa gcagcagatt acgcgcagaa aaaaaggatc   7740
tcaagaagat cctttgatct tttctacggg gtctgacgct cagtggaacg aaaactcacg   7800
ttaagggatt ttggtcatga gattatcaaa aaggatcttc acctagatcc ttttaaatta   7860
aaaatgaagt tttaaatcaa tctaaagtat atatgagtaa acttggtctg acagttacca   7920
atgcttaatc agtgaggcac ctatctcagc gatctgtcta tttcgttcat ccatagttgc   7980
ctgactcccc gtcgtgtaga taactacgat acgggagggc ttaccatctg gccccagtgc   8040
tgcaatgata ccgcgagacc cacgctcacc ggctccagat ttatcagcaa taaaccagcc   8100
agccggaagg gccgagcgca gaagtggtcc tgcaacttta tccgcctcca tccagtctat   8160
taattgttgc cgggaagcta gagtaagtag ttcgccagtt aatagtttgc gcaacgttgt   8220
tgccattgct acaggcatcg tggtgtcacg ctcgtcgttt ggtatggctt cattcagctc   8280
cggttcccaa cgatcaaggc gagttacatg atcccccatg ttgtgcaaaa aagcggttag   8340
ctccttcggt cctccgatcg ttgtcagaag taagttggcc gcagtgttat cactcatggt   8400
tatggcagca ctgcataatt ctcttactgt catgccatcc gtaagatgct tttctgtgac   8460
tggtgagtac tcaaccaagt cattctgaga atagtgtatg cggcgaccga gttgctcttg   8520
cccggcgtca atacgggata ataccgcgcc acatagcaga actttaaaag tgctcatcat   8580
tggaaaacgt tcttcggggc gaaaactctc aaggatctta ccgctgttga gatccagttc   8640
gatgtaaccc actcgtgcac ccaactgatc ttcagcatct tttactttca ccagcgtttc   8700
tgggtgagca aaaacaggaa ggcaaaatgc cgcaaaaaag ggaataaggg cgacacggaa   8760
atgttgaata ctcatactct tcctttttca atattattga agcatttatc agggttattg   8820
tctcatgagc ggatacatat ttgaatgtat ttagaaaaat aaacaaatag gggttccgcg   8880
cacatttccc cgaaaagtgc cacctgacgt cg                                 8912
```

-continued

<210> SEQ ID NO 20
<211> LENGTH: 9626
<212> TYPE: DNA
<213> ORGANISM: Artificial sequence
<220> FEATURE:
<223> OTHER INFORMATION: Trivalent anti-FcgR1-PspA-HuSA

<400> SEQUENCE: 20
acggatcggg agatctcccg atcccctatg gtcgactctc agtacaatct gctctgatgc 60
cgcatagtta agccagtatc tgctccctgc ttgtgtgttg gaggtcgctg agtagtgcgc 120
gagcaaaatt taagctacaa caaggcaagg cttgaccgac aattgcatga agaatctgct 180
tagggttagg cgttttgcgc tgcttcgcga tgtacgggcc agatatacgc gttgacattg 240
attattgact agttattaat agtaatcaat tacggggtca ttagttcata gcccatatat 300
ggagttccgc gttacataac ttacggtaaa tggcccgcct ggctgaccgc ccaacgaccc 360
ccgcccattg acgtcaataa tgacgtatgt tcccatagta acgccaatag ggactttcca 420
ttgacgtcaa tgggtggact atttacggta aactgcccac ttggcagtac atcaagtgta 480
tcatatgcca agtacgcccc ctattgacgt caatgacggt aaatggcccg cctggcatta 540
tgcccagtac atgaccttat gggactttcc tacttggcag tacatctacg tattagtcat 600
cgctattacc atggtgatgc ggttttggca gtacatcaat gggcgtggat agcggtttga 660
ctcacgggga tttccaagtc tccaccccat tgacgtcaat gggagtttgt tttggcacca 720
aaatcaacgg gactttccaa aatgtcgtaa caactccgcc ccattgacgc aaatgggcgg 780
taggcgtgta cggtgggagg tctatataag cagagctctc tggctaacta gagaacccac 840
tgcttactgg cttatcgaaa ttaatacgac tcactatagg gagacccaag cttcaccatg 900
ggatggagct gtatcatcct cttcttggtg gccacagcta ccggtgtcca ctccgatatc 960
cagctgaccc agagcccaag cagcctgagc gccagcgtgg gtgacagagt gaccatcacc 1020
tgtaagtcca gtcaaagtgt tttatacagt tcaaatcaga agaactactt ggcctggtac 1080
cagcagaagc caggtaaggc tccaaagctg ctgatctact gggcatccac tagggaatct 1140
ggtgtgccaa gcagattcag cggtagcggt agcggtaccg acttcacctt caccatcagc 1200
agcctccagc cagaggacat cgccacctac tactgccatc aatacctctc ctcgtggacg 1260
ttcggccaag ggaccaaggt ggaaatcaag agctctggcg gtggcggctc cggaggtgga 1320
ggcagcggag gggtggatc cgaggtccaa ctggtggaga gcggtggagg tgttgtgcaa 1380
cctggccggt ccctgcgcct gtcctgctcc tcgtctggct tcattttcag tgacaattac 1440
atgtattggg tgagacaggc acctggaaaa ggtcttgagt gggttgcaac cattagtgat 1500
ggtggtagtt acacctacta tccagacagt gtgaagggaa gatttacaat atcgagagac 1560
aacagcaaga acacattgtt cctgcaaatg gacagcctga gacccgaaga caccggggtc 1620
tatttttgtg caagaggcta ctataggtac gagggggcta tggactactg gggccaaggg 1680
accccggtca ccgtctcctc aggctcgacc ggtgggggag gctcgaccag cgctggaggc 1740
ggaggttcta gtgacatcca gctgacccag agcccaagca gcctgagcgc cagcgtgggt 1800
gacagagtga ccatcacctg taagtccagt caaagtgttt tatacagttc aaatcagaag 1860
aactacttgg cctggtacca gcagaagcca ggtaaggctc caaagctgct gatctactgg 1920
gcatccacta gggaatctgg tgtgccaagc agattcagcg gtagcggtag cggtaccgac 1980
ttcaccttca ccatcagcag cctccagcca gaggacatcg ccacctacta ctgccatcaa 2040

-continued

```
tacctctcct cgtggacgtt cggccaaggg accaaggtgg aaatcaagag ctctggcggt   2100
ggcggctccg gaggtggagg cagcggaggg ggtggatccg aggtccaact ggtggagagc   2160
ggtggaggtg ttgtgcaacc tggccggtcc ctgcgcctgt cctgctcctc gtctggcttc   2220
attttcagtg acaattacat gtattgggtg agacaggcac ctggaaaagg tcttgagtgg   2280
gttgcaacca ttagtgatgg tggtagttac acctactatc cagacagtgt gaagggaaga   2340
tttacaatat cgagagacaa cagcaagaac acattgttcc tgcaaatgga cagcctgaga   2400
cccgaagaca ccggggtcta tttttgtgca agaggctact ataggtacga gggggctatg   2460
gactactggg gccaagggac cccggtcacc gtctcctcag gctcgaccgg tgggggaggc   2520
tcgactgcta gcggaggcgg aggttctagt gacatccagc tgacccagag cccaagcagc   2580
ctgagcgcca gcgtgggtga cagagtgacc atcacctgta agtccagtca aagtgtttta   2640
tacagttcaa atcagaagaa ctacttggcc tggtaccagc agaagccagg taaggctcca   2700
aagctgctga tctactgggc atccactagg gaatctggtg tgccaagcag attcagcggt   2760
agcggtagcg gtaccgactt caccttcacc atcagcagcc tccagccaga ggacatcgcc   2820
acctactact gccatcaata cctctcctcg tggacgttcg gccaagggac caaggtggaa   2880
atcaagagct ctggcggtgg cggctccgga ggtggaggca gcggaggggg tggatccgag   2940
gtccaactgg tggagagcgg tggaggtgtt gtgcaacctg gccggtccct gcgcctgtcc   3000
tgctcctcgt ctggcttcat tttcagtgac aattacatgt attgggtgag acaggcacct   3060
ggaaaaggtc ttgagtgggt tgcaaccatt agtgatggtg gtagttacac ctactatcca   3120
gacagtgtga agggaagatt tacaatatcg agagacaaca gcaagaacac attgttcctg   3180
caaatggaca gcctgagacc cgaagacacc ggggtctatt tttgtgcaag aggctactat   3240
aggtacgagg gggctatgga ctactggggc caagggaccc cggtcaccgt ctcctcaggc   3300
tcgaccggtg gggaggctc gactgaattc atggaagaat ctcccgtagc cagtcagtct   3360
aaagctgaga aagactatga tgcagcgaag aaagatgcta agaatgcgaa aaaagcagta   3420
gaagatgctc aaaaggcttt agatgatgca aaagctgctc agaaaaaata tgacgaggat   3480
cagaagaaaa ctgaggagaa agccgcgcta gaaaaagcag cgtctgaaga gatggataag   3540
gcagtggcag cagttcaaca agcgtatcta gcctatcaac aagctacaga caaagccgca   3600
aaagacgcag cagataagat gatagatgaa gctaagaaac gcgaagaaga ggcaaaaact   3660
aaatttaata ctgttcgagc aatggtagtt cctgagccag agcagttggc tgagactaag   3720
aaaaaatcag aagaagctaa acaaaaagca ccagaactta ctaaaaaact agaagaagct   3780
aaagcaaaat tagaagaggc tgagaaaaaa gctactgaag ccaaacaaaa agtggatgct   3840
gaagaagtcg ctcctcaagc taaaatcgct gaattggaaa atcaagttca tagactagaa   3900
caagagctca aagagattga tgagtctgaa tcagaagatt atgctaaaga aggtttccgt   3960
gctcctcttc aatctaaatt ggatgccaaa aaagctaaac tatcaaaact tgaagagtta   4020
agtgataaga ttgatgagtt agacgctgaa attgcaaaac ttgaagatca acttaaagct   4080
gctgaagaaa acaataatgt agaagactac tttaaagaag gtttagagaa aactattgct   4140
gctaaaaaag ctgaattaga aaaaactgaa gctgacctta agaaagcagt taatgagcca   4200
gaaaaaccag ctccagctcc agaaactcca gccccagaac tcgagggtgg atcaggcggt   4260
tgtacactag agaagtgctg tgccgctgca gatcctcatg aatgctatgc caaagtgttc   4320
gatgaattta aacctcttgt ggaagagcct cagaatttaa tcaaacaaaa ttgtgagctt   4380
tttgagcagc ttggagagta caaattccag aatgcgctat tagttcgtta caccaagaaa   4440
```

-continued

```
gtaccccaag tgtcaactcc aactcttgta gaggtctcaa gaaacctagg aaaagtgggc   4500
agcaaatgtt gtaaacatcc tgaagcaaaa agaatgccct gtgcagaaga ctatctatcc   4560
gtggtcctga accagttatg tgtgttgcat gagaaaacgc cagtaagtga cagagtcacc   4620
aaatgctgca cagaatcctt ggtgaacagg cgaccatgct tttcagctct ggaagtcgat   4680
gaaacatacg ttcccaaaga gtttaatgct gaaacattca ccttccatgc agatatatgc   4740
acactttctg agaaggagag acaaatcaag aaacaaactg cacttgttga gctcgtgaaa   4800
cacaagccca aggcaacaaa agagcaactg aaagctgtta tggatgattt cgcagctttt   4860
gtagagaagt gctgcaaggc tgacgataag gagacctgct ttgccgagga gggtaaaaaa   4920
cttgttgctg caagtcaagc tgccttaggc ttacgtacgc accaccacca ccaccactga   4980
gatccggctg ctaacaaagc ccgaaaggaa gctgagttgg ctgctgccac cgctgagcaa   5040
taactagcat aaccccttgg ggcctctaaa cgggtcttga ggggttttgc ggccgcacga   5100
cagaaactca tctcagaaga ggatctgaat ggcgccgcac atcaccatca tcaccattga   5160
ttctagaggg ccctattcta tagtgtcacc taaatgctag agctcgctga tcagcctcga   5220
ctgtgccttc tagttgccag ccatctgttg tttgcccctc ccccgtgcct tccttgaccc   5280
tggaaggtgc cactcccact gtcctttcct aataaaatga ggaaattgca tcgcattgtc   5340
tgagtaggtg tcattctatt ctggggggtg gggtggggca ggacagcaag ggggaggatt   5400
gggaagacaa tagcaggcat gctggggatg cggtgggctc tatggcttct gaggcggaaa   5460
gaaccagctg gggctctagg gggtatcccc acgcgccctg tagcggcgca ttaagcgcgg   5520
cgggtgtggt ggttacgcgc agcgtgaccg ctacacttgc cagcgcccta gcgcccgctc   5580
ctttcgcttt cttcccttcc tttctcgcca cgttcgccgg ctttccccgt caagctctaa   5640
atcggggcat ccctttaggg ttccgattta gtgctttacg gcacctcgac cccaaaaaac   5700
ttgattaggg tgatggttca cgtagtgggc catcgccctg atagacggtt tttcgccctt   5760
tgacgttgga gtccacgttc tttaatagtg gactcttgtt ccaaactgga acaacactca   5820
accctatctc ggtctattct tttgatttat aagggatttt ggggatttcg gcctattggt   5880
taaaaaatga gctgatttaa caaaaattta acgcgaatta attctgtgga atgtgtgtca   5940
gttagggtgt ggaaagtccc caggctcccc aggcaggcag aagtatgcaa agcatgcatc   6000
tcaattagtc agcaaccagg tgtggaaagt ccccaggctc cccagcaggc agaagtatgc   6060
aaagcatgca tctcaattag tcagcaacca tagtcccgcc cctaactccg cccatcccgc   6120
ccctaactcc gcccagttcc gcccattctc cgccccatgg ctgactaatt ttttttattt   6180
atgcagaggc cgaggccgcc tctgcctctg agctattcca gaagtagtga ggaggctttt   6240
ttggaggcct aggcttttgc aaaaagctcc cgggagcttg tatatccatt ttcggatctg   6300
atcaagagac aggatgagga tcgtttcgca tgattgaaca agatggattg cacgcaggtt   6360
ctccggccgc ttgggtggag aggctattcg gctatgactg ggcacaacag acaatcggct   6420
gctctgatgc cgccgtgttc cggctgtcag cgcaggggcg cccggttctt tttgtcaaga   6480
ccgacctgtc cggtgccctg aatgaactgc aggacgaggc agcgcggcta tcgtggctgg   6540
ccacgacggg cgttccttgc gcagctgtgc tcgacgttgt cactgaagcg ggaagggact   6600
ggctgctatt gggcgaagtg ccggggcagg atctcctgtc atctcacctt gctcctgccg   6660
agaaagtatc catcatggct gatgcaatgc ggcggctgca tacgcttgat ccggctacct   6720
gcccattcga ccaccaagcg aaacatcgca tcgagcgagc acgtactcgg atggaagccg   6780
```

-continued

```
gtcttgtcga tcaggatgat ctggacgaag agcatcaggg gctcgcgcca gccgaactgt   6840
tcgccaggct caaggcgcgc atgcccgacg gcgaggatct cgtcgtgacc catggcgatg   6900
cctgcttgcc gaatatcatg gtggaaaatg gccgcttttc tggattcatc gactgtggcc   6960
ggctgggtgt ggcggaccgc tatcaggaca tagcgttggc tacccgtgat attgctgaag   7020
agcttggcgg cgaatgggct gaccgcttcc tcgtgcttta cggtatcgcc gctcccgatt   7080
cgcagcgcat cgccttctat cgccttcttg acgagttctt ctgagcggga ctctggggtt   7140
cgaaatgacc gaccaagcga cgcccaacct gccatcacga gatttcgatt ccaccgccgc   7200
cttctatgaa aggttgggct tcggaatcgt tttccgggac gccggctgga tgatcctcca   7260
gcgcggggat ctcatgctgg agttcttcgc ccaccccaac ttgtttattg cagcttataa   7320
tggttacaaa taaagcaata gcatcacaaa tttcacaaat aaagcatttt tttcactgca   7380
ttctagttgt ggtttgtcca aactcatcaa tgtatcttat catgtctgta taccgtcgac   7440
ctctagctag agcttggcgt aatcatggtc atagctgttt cctgtgtgaa attgttatcc   7500
gctcacaatt ccacacaaca tacgagccgg aagcataaag tgtaaagcct ggggtgccta   7560
atgagtgagc taactcacat taattgcgtt gcgctcactg cccgctttcc agtcgggaaa   7620
cctgtcgtgc cagctgcatt aatgaatcgg ccaacgcgcg gggagaggcg gtttgcgtat   7680
tgggcgctct tccgcttcct cgctcactga ctcgctgcgc tcggtcgttc ggctgcggcg   7740
agcggtatca gctcactcaa aggcggtaat acggttatcc acagaatcag gggataacgc   7800
aggaaagaac atgtgagcaa aaggccagca aaaggccagg aaccgtaaaa aggccgcgtt   7860
gctggcgttt ttccataggc tccgcccccc tgacgagcat cacaaaaatc gacgctcaag   7920
tcagaggtgg cgaaacccga caggactata aagataccag gcgtttcccc ctggaagctc   7980
cctcgtgcgc tctcctgttc cgaccctgcc gcttaccgga tacctgtccg cctttctccc   8040
ttcgggaagc gtggcgcttt ctcaatgctc acgctgtagg tatctcagtt cggtgtaggt   8100
cgttcgctcc aagctgggct gtgtgcacga accccccgtt cagcccgacc gctgcgcctt   8160
atccggtaac tatcgtcttg agtccaaccc ggtaagacac gacttatcgc cactggcagc   8220
agccactggt aacaggatta gcagagcgag gtatgtaggc ggtgctacag agttcttgaa   8280
gtggtggcct aactacggct acactagaag gacagtattt ggtatctgcg ctctgctgaa   8340
gccagttacc ttcggaaaaa gagttggtag ctcttgatcc ggcaaacaaa ccaccgctgg   8400
tagcggtggt ttttttgttt gcaagcagca gattacgcgc agaaaaaaag gatctcaaga   8460
agatcctttg atcttttcta cggggtctga cgctcagtgg aacgaaaact cacgttaagg   8520
gattttggtc atgagattat caaaaaggat cttcacctag atccttttaa attaaaaatg   8580
aagttttaaa tcaatctaaa gtatatatga gtaaacttgg tctgacagtt accaatgctt   8640
aatcagtgag gcacctatct cagcgatctg tctatttcgt tcatccatag ttgcctgact   8700
ccccgtcgtg tagataacta cgatacggga gggcttacca tctggcccca gtgctgcaat   8760
gataccgcga gacccacgct caccggctcc agatttatca gcaataaacc agccagccgg   8820
aagggccgag cgcagaagtg gtcctgcaac tttatccgcc tccatccagt ctattaattg   8880
ttgccgggaa gctagagtaa gtagttcgcc agttaatagt ttgcgcaacg ttgttgccat   8940
tgctacaggc atcgtggtgt cacgctcgtc gtttggtatg gcttcattca gctccggttc   9000
ccaacgatca aggcgagtta catgatcccc catgttgtgc aaaaaagcgg ttagctcctt   9060
cggtcctccg atcgttgtca gaagtaagtt ggccgcagtg ttatcactca tggttatggc   9120
agcactgcat aattctctta ctgtcatgcc atccgtaaga tgcttttctg tgactggtga   9180
```

```
gtactcaacc aagtcattct gagaatagtg tatgcggcga ccgagttgct cttgcccggc   9240

gtcaatacgg gataataccg cgccacatag cagaacttta aaagtgctca tcattggaaa   9300

acgttcttcg gggcgaaaac tctcaaggat cttaccgctg ttgagatcca gttcgatgta   9360

acccactcgt gcacccaact gatcttcagc atcttttact ttcaccagcg tttctgggtg   9420

agcaaaaaca ggaaggcaaa atgccgcaaa aaagggaata agggcgacac ggaaatgttg   9480

aatactcata ctcttccttt ttcaatatta ttgaagcatt tatcagggtt attgtctcat   9540

gagcggatac atatttgaat gtatttagaa aaataaacaa ataggggttc cgcgcacatt   9600

tccccgaaaa gtgccacctg acgtcg                                         9626
```

<210> SEQ ID NO 21
<211> LENGTH: 8102
<212> TYPE: DNA
<213> ORGANISM: Artificial sequence
<220> FEATURE:
<223> OTHER INFORMATION: Bivalent anti-FcgR1-PspA

<400> SEQUENCE: 21

```
acggatcggg agatctcccg atcccctatg gtcgactctc agtacaatct gctctgatgc     60

cgcatagtta agccagtatc tgctccctgc ttgtgtgttg gaggtcgctg agtagtgcgc    120

gagcaaaatt taagctacaa caaggcaagg cttgaccgac aattgcatga agaatctgct    180

tagggttagg cgttttgcgc tgcttcgcga tgtacgggcc agatatacgc gttgacattg    240

attattgact agttattaat agtaatcaat tacggggtca ttagttcata gcccatatat    300

ggagttccgc gttacataac ttacggtaaa tggcccgcct ggctgaccgc ccaacgaccc    360

ccgcccattg acgtcaataa tgacgtatgt tcccatagta acgccaatag ggactttcca    420

ttgacgtcaa tgggtggact atttacggta aactgcccac ttggcagtac atcaagtgta    480

tcatatgcca agtacgcccc ctattgacgt caatgacggt aaatggcccg cctggcatta    540

tgcccagtac atgaccttat gggactttcc tacttggcag tacatctacg tattagtcat    600

cgctattacc atggtgatgc ggttttggca gtacatcaat gggcgtggat agcggtttga    660

ctcacgggga tttccaagtc tccaccccat tgacgtcaat gggagtttgt tttggcacca    720

aaatcaacgg gactttccaa aatgtcgtaa caactccgcc ccattgacgc aaatgggcgg    780

taggcgtgta cggtgggagg tctatataag cagagctctc tggctaacta gagaacccac    840

tgcttactgg cttatcgaaa ttaatacgac tcactatagg gagacccaag cttcaccatg    900

ggatggagct gtatcatcct cttcttggtg gccacagcta ccggtgtcca ctccgatatc    960

cagctgaccc agagcccaag cagcctgagc gccagcgtgg gtgacagagt gaccatcacc   1020

tgtaagtcca gtcaaagtgt tttatacagt tcaaatcaga agaactactt ggcctggtac   1080

cagcagaagc caggtaaggc tccaaagctg ctgatctact gggcatccac tagggaatct   1140

ggtgtgccaa gcagattcag cggtagcggt agcggtaccg acttcacctt caccatcagc   1200

agcctccagc cagaggacat cgccacctac tactgccatc aatacctctc ctcgtggacg   1260

ttcggccaag ggaccaaggt ggaaatcaag agctctggcg gtggcggctc cggaggtgga   1320

ggcagcggag ggggtggatc cgaggtccaa ctggtggaga gcggtggagg tgttgtgcaa   1380

cctggccggt ccctgcgcct gtcctgctcc tcgtctggct tcattttcag tgacaattac   1440

atgtattggg tgagacaggc acctggaaaa ggtcttgagt gggttgcaac cattagtgat   1500

ggtggtagtt acacctacta tccagacagt gtgaagggaa gatttacaat atcgagagac   1560
```

```
aacagcaaga acacattgtt cctgcaaatg gacagcctga gacccgaaga caccggggtc   1620
tatttttgtg caagaggcta ctataggtac gagggggcta tggactactg gggccaaggg   1680
accccggtca ccgtctcctc aggctcgacc ggtgggggag gctcgaccgg aggcggaggt   1740
tctagtgaca tccagctgac ccagagccca agcagcctga gcgccagcgt gggtgacaga   1800
gtgaccatca cctgtaagtc cagtcaaagt gttttataca gttcaaatca gaagaactac   1860
ttggcctggt accagcagaa gccaggtaag gctccaaagc tgctgatcta ctgggcatcc   1920
actagggaat ctggtgtgcc aagcagattc agcggtagcg gtagcggtac cgacttcacc   1980
ttcaccatca gcagcctcca gccagaggac atcgccacct actactgcca tcaatacctc   2040
tcctcgtgga cgttcggcca agggaccaag gtggaaatca agagctctgg cggtggcggc   2100
tccggaggtg gaggcagcgg agggggtgga tccgaggtcc aactggtgga gagcggtgga   2160
ggtgttgtgc aacctggccg gtccctgcgc ctgtcctgct cctcgtctgg cttcattttc   2220
agtgacaatt acatgtattg ggtgagacag gcacctggaa aaggtcttga gtgggttgca   2280
accattagtg atggtggtag ttacacctac tatccagaca gtgtgaaggg aagatttaca   2340
atatcgagag acaacagcaa gaacacattg ttcctgcaaa tggacagcct gagacccgaa   2400
gacaccgggg tctatttttg tgcaagaggc tactataggt acgagggggc tatggactac   2460
tggggccaag ggaccccggt caccgtctcc tcaggctcga ccggtggggg agggtcgact   2520
atggaagaat ctcccgtagc cagtcagtct aaagctgaga aagactatga tgcagcgaag   2580
aaagatgcta agaatgcgaa aaaagcagta gaagatgctc aaaaggcttt agatgatgca   2640
aaagctgctc agaaaaaata tgacgaggat cagaagaaaa ctgaggagaa agccgcgcta   2700
gaaaaagcag cgtctgaaga gatggataag gcagtggcag cagttcaaca agcgtatcta   2760
gcctatcaac aagctacaga caaagccgca aaagacgcag cagataagat gatagatgaa   2820
gctaagaaac gcgaagaaga ggcaaaaact aaatttaata ctgttcgagc aatggtagtt   2880
cctgagccag agcagttggc tgagactaag aaaaaatcag aagaagctaa acaaaaagca   2940
ccagaactta ctaaaaaact agaagaagct aaagcaaaat tagaagaggc tgagaaaaaa   3000
gctactgaag ccaaacaaaa agtggatgct gaagaagtcg ctcctcaagc taaaatcgct   3060
gaattggaaa atcaagttca tagactagaa caagagctca aagagattga tgagtctgaa   3120
tcagaagatt atgctaaaga aggtttccgt gctcctcttc aatctaaatt ggatgccaaa   3180
aaagctaaac tatcaaaact tgaagagtta agtgataaga ttgatgagtt agacgctgaa   3240
attgcaaaac ttgaagatca acttaaagct gctgaagaaa acaataatgt agaagactac   3300
tttaaagaag gtttagagaa aactattgct gctaaaaaag ctgaattaga aaaaactgaa   3360
gctgacctta agaaagcagt taatgagcca gaaaaaccag ctccagctcc agaaactcca   3420
gccccagaac tcgagcacca ccaccaccac cactgagatc cggctgctaa caaagcccga   3480
aaggaagctg agttggctgc tgccaccgct gagcaataac tagcataacc ccttggggcc   3540
tctaaacggg tcttgagggg ttttgcggcc gcacgacaga aactcatctc agaagaggat   3600
ctgaatggcg ccgcacatca ccatcatcac cattgattct agagggccct attctatagt   3660
gtcacctaaa tgctagagct cgctgatcag cctcgactgt gccttctagt tgccagccat   3720
ctgttgtttg cccctccccc gtgccttcct tgaccctgga aggtgccact cccactgtcc   3780
tttcctaata aaatgaggaa attgcatcgc attgtctgag taggtgtcat tctattctgg   3840
ggggtggggt ggggcaggac agcaaggggg aggattggga agacaatagc aggcatgctg   3900
gggatgcggt gggctctatg gcttctgagg cggaaagaac cagctggggc tctagggggt   3960
```

-continued

```
atccccacgc gccctgtagc ggcgcattaa gcgcggcggg tgtggtggtt acgcgcagcg   4020
tgaccgctac acttgccagc gccctagcgc ccgctccttt cgctttcttc ccttcctttc   4080
tcgccacgtt cgccggcttt ccccgtcaag ctctaaatcg ggcatccct ttagggttcc    4140
gatttagtgc tttacggcac ctcgacccca aaaaacttga ttagggtgat ggttcacgta   4200
gtgggccatc gccctgatag acggtttttc gccctttgac gttggagtcc acgttcttta   4260
atagtggact cttgttccaa actggaacaa cactcaaccc tatctcggtc tattcttttg   4320
atttataagg gattttgggg atttcggcct attggttaaa aaatgagctg atttaacaaa   4380
aatttaacgc gaattaattc tgtggaatgt gtgtcagtta gggtgtggaa agtccccagg   4440
ctccccaggc aggcagaagt atgcaaagca tgcatctcaa ttagtcagca accaggtgtg   4500
gaaagtcccc aggctcccca gcaggcagaa gtatgcaaag catgcatctc aattagtcag   4560
caaccatagt cccgccccta actccgccca tcccgcccct aactccgccc agttccgccc   4620
attctccgcc ccatggctga ctaatttttt ttatttatgc agaggccgag gccgcctctg   4680
cctctgagct attccagaag tagtgaggag gcttttttgg aggcctaggc ttttgcaaaa   4740
agctcccggg agcttgtata tccattttcg gatctgatca agagacagga tgaggatcgt   4800
ttcgcatgat tgaacaagat ggattgcacg caggttctcc ggccgcttgg gtggagaggc   4860
tattcggcta tgactgggca caacagacaa tcggctgctc tgatgccgcc gtgttccggc   4920
tgtcagcgca ggggcgcccg gttctttttg tcaagaccga cctgtccggt gccctgaatg   4980
aactgcagga cgaggcagcg cggctatcgt ggctggccac gacgggcgtt ccttgcgcag   5040
ctgtgctcga cgttgtcact gaagcgggaa gggactggct gctattgggc gaagtgccgg   5100
ggcaggatct cctgtcatct caccttgctc ctgccgagaa agtatccatc atggctgatg   5160
caatgcggcg gctgcatacg cttgatccgg ctacctgccc attcgaccac caagcgaaac   5220
atcgcatcga gcgagcacgt actcggatgg aagccggtct tgtcgatcag gatgatctgg   5280
acgaagagca tcaggggctc gcgccagccg aactgttcgc caggctcaag gcgcgcatgc   5340
ccgacggcga ggatctcgtc gtgacccatg gcgatgcctg cttgccgaat atcatggtgg   5400
aaaatggccg cttttctgga ttcatcgact gtggccggct gggtgtggcg gaccgctatc   5460
aggacatagc gttggctacc cgtgatattg ctgaagagct tggcggcgaa tgggctgacc   5520
gcttcctcgt gctttacggt atcgccgctc ccgattcgca gcgcatcgcc ttctatcgcc   5580
ttcttgacga gttcttctga gcgggactct ggggttcgaa atgaccgacc aagcgacgcc   5640
caacctgcca tcacgagatt tcgattccac cgccgccttc tatgaaaggt tgggcttcgg   5700
aatcgttttc cgggacgccg gctggatgat cctccagcgc ggggatctca tgctggagtt   5760
cttcgcccac cccaacttgt ttattgcagc ttataatggt tacaaataaa gcaatagcat   5820
cacaaatttc acaaataaag catttttttc actgcattct agttgtggtt tgtccaaact   5880
catcaatgta tcttatcatg tctgtatacc gtcgacctct agctagagct tggcgtaatc   5940
atggtcatag ctgtttcctg tgtgaaattg ttatccgctc acaattccac acaacatacg   6000
agccggaagc ataaagtgta aagcctgggg tgcctaatga gtgagctaac tcacattaat   6060
tgcgttgcgc tcactgcccg ctttccagtc gggaaacctg tcgtgccagc tgcattaatg   6120
aatcggccaa cgcgcgggga gaggcggttt gcgtattggg cgctcttccg cttcctcgct   6180
cactgactcg ctgcgctcgg tcgttcggct gcggcgagcg gtatcagctc actcaaaggc   6240
ggtaatacgg ttatccacag aatcagggga taacgcagga aagaacatgt gagcaaaagg   6300
```

ccagcaaaag gccaggaacc gtaaaaaggc cgcgttgctg gcgtttttcc ataggctccg 6360
cccccctgac gagcatcaca aaaatcgacg ctcaagtcag aggtggcgaa acccgacagg 6420
actataaaga taccaggcgt ttccccctgg aagctccctc gtgcgctctc ctgttccgac 6480
cctgccgctt accggatacc tgtccgcctt tctcccttcg ggaagcgtgg cgctttctca 6540
atgctcacgc tgtaggtatc tcagttcggt gtaggtcgtt cgctccaagc tgggctgtgt 6600
gcacgaaccc cccgttcagc ccgaccgctg cgccttatcc ggtaactatc gtcttgagtc 6660
caacccggta agacacgact tatcgccact ggcagcagcc actggtaaca ggattagcag 6720
agcgaggtat gtaggcggtg ctacagagtt cttgaagtgg tggcctaact acggctacac 6780
tagaaggaca gtatttggta tctgcgctct gctgaagcca gttaccttcg gaaaaagagt 6840
tggtagctct tgatccggca aacaaaccac cgctggtagc ggtggttttt ttgtttgcaa 6900
gcagcagatt acgcgcagaa aaaaaggatc tcaagaagat cctttgatct tttctacggg 6960
gtctgacgct cagtggaacg aaaactcacg ttaagggatt ttggtcatga gattatcaaa 7020
aaggatcttc acctagatcc ttttaaatta aaaatgaagt tttaaatcaa tctaaagtat 7080
atatgagtaa acttggtctg acagttacca atgcttaatc agtgaggcac ctatctcagc 7140
gatctgtcta tttcgttcat ccatagttgc ctgactcccc gtcgtgtaga taactacgat 7200
acgggagggc ttaccatctg gccccagtgc tgcaatgata ccgcgagacc cacgctcacc 7260
ggctccagat ttatcagcaa taaaccagcc agccggaagg gccgagcgca gaagtggtcc 7320
tgcaacttta tccgcctcca tccagtctat taattgttgc cgggaagcta gagtaagtag 7380
ttcgccagtt aatagtttgc gcaacgttgt tgccattgct acaggcatcg tggtgtcacg 7440
ctcgtcgttt ggtatggctt cattcagctc cggttcccaa cgatcaaggc gagttacatg 7500
atcccccatg ttgtgcaaaa aagcggttag ctccttcggt cctccgatcg ttgtcagaag 7560
taagttggcc gcagtgttat cactcatggt tatggcagca ctgcataatt ctcttactgt 7620
catgccatcc gtaagatgct tttctgtgac tggtgagtac tcaaccaagt cattctgaga 7680
atagtgtatg cggcgaccga gttgctcttg cccggcgtca atacgggata ataccgcgcc 7740
acatagcaga actttaaaag tgctcatcat tggaaaacgt tcttcggggc gaaaactctc 7800
aaggatctta ccgctgttga gatccagttc gatgtaaccc actcgtgcac ccaactgatc 7860
ttcagcatct tttactttca ccagcgtttc tgggtgagca aaaacaggaa ggcaaaatgc 7920
cgcaaaaaag ggaataaggg cgacacggaa atgttgaata ctcatactct tcctttttca 7980
atattattga agcatttatc agggttattg tctcatgagc ggatacatat ttgaatgtat 8040
ttagaaaaat aaacaaatag gggttccgcg cacatttccc cgaaaagtgc cacctgacgt 8100
cg 8102

<210> SEQ ID NO 22
<211> LENGTH: 7268
<212> TYPE: DNA
<213> ORGANISM: Artificial sequence
<220> FEATURE:
<223> OTHER INFORMATION: Non-FcgR1 targeted PspA-HuSA

<400> SEQUENCE: 22
acggatcggg agatctcccg atcccctatg gtcgactctc agtacaatct gctctgatgc 60
cgcatagtta agccagtatc tgctccctgc ttgtgtgttg gaggtcgctg agtagtgcgc 120
gagcaaaatt taagctacaa caaggcaagg cttgaccgac aattgcatga agaatctgct 180
tagggttagg cgttttgcgc tgcttcgcga tgtacgggcc agatatacgc gttgacattg 240

-continued

```
attattgact agttattaat agtaatcaat tacggggtca ttagttcata gcccatatat    300
ggagttccgc gttacataac ttacggtaaa tggcccgcct ggctgaccgc ccaacgaccc    360
ccgcccattg acgtcaataa tgacgtatgt tcccatagta acgccaatag ggactttcca    420
ttgacgtcaa tgggtggact atttacggta aactgcccac ttggcagtac atcaagtgta    480
tcatatgcca agtacgcccc ctattgacgt caatgacggt aaatggcccg cctggcatta    540
tgcccagtac atgaccttat gggactttcc tacttggcag tacatctacg tattagtcat    600
cgctattacc atggtgatgc ggttttggca gtacatcaat gggcgtggat agcggtttga    660
ctcacgggga tttccaagtc tccaccccat tgacgtcaat gggagtttgt tttggcacca    720
aaatcaacgg gactttccaa aatgtcgtaa caactccgcc ccattgacgc aaatgggcgg    780
taggcgtgta cggtgggagg tctatataag cagagctctc tggctaacta gagaacccac    840
tgcttactgg cttatcgaaa ttaatacgac tcactatagg gagacccaag cttcaccatg    900
ggatggagct gtatcatcct cttcttggtg gccacagcta ccggtggggg aggctcgact    960
gctagcgaat tcatggaaga atctcccgta gccagtcagt ctaaagctga gaaagactat   1020
gatgcagcga agaaagatgc taagaatgcg aaaaaagcag tagaagatgc tcaaaaggct   1080
ttagatgatg caaaagctgc tcagaaaaaa tatgacgagg atcagaagaa aactgaggag   1140
aaagccgcgc tagaaaaagc agcgtctgaa gagatggata aggcagtggc agcagttcaa   1200
caagcgtatc tagcctatca acaagctaca gacaaagccg caaaagacgc agcagataag   1260
atgatagatg aagctaagaa acgcgaagaa gaggcaaaaa ctaaatttaa tactgttcga   1320
gcaatggtag ttcctgagcc agagcagttg gctgagacta agaaaaaatc agaagaagct   1380
aaacaaaaag caccagaact tactaaaaaa ctagaagaag ctaaagcaaa attagaagag   1440
gctgagaaaa aagctactga agccaaacaa aaagtggatg ctgaagaagt cgctcctcaa   1500
gctaaaatcg ctgaattgga aaatcaagtt catagactag aacaagagct caaagagatt   1560
gatgagtctg aatcagaaga ttatgctaaa gaaggtttcc gtgctcctct tcaatctaaa   1620
ttggatgcca aaaaagctaa actatcaaaa cttgaagagt taagtgataa gattgatgag   1680
ttagacgctg aaattgcaaa acttgaagat caacttaaag ctgctgaaga aaacaataat   1740
gtagaagact actttaaaga aggtttagag aaaactattg ctgctaaaaa agctgaatta   1800
gaaaaaactg aagctgacct taagaaagca gttaatgagc cagaaaaacc agctccagct   1860
ccagaaactc cagccccaga actcgagggt ggatcaggcg gttgtacact agagaagtgc   1920
tgtgccgctg cagatcctca tgaatgctat gccaaagtgt tcgatgaatt taaacctctt   1980
gtggaagagc ctcagaattt aatcaaacaa aattgtgagc tttttgagca gcttggagag   2040
tacaaattcc agaatgcgct attagttcgt tacaccaaga aagtacccca agtgtcaact   2100
ccaactcttg tagaggtctc aagaaaccta ggaaaagtgg gcagcaaatg ttgtaaacat   2160
cctgaagcaa aaagaatgcc ctgtgcagaa gactatctat ccgtggtcct gaaccagtta   2220
tgtgtgttgc atgagaaaac gccagtaagt gacagagtca ccaaatgctg cacagaatcc   2280
ttggtgaaca ggcgaccatg cttttcagct ctggaagtcg atgaaacata cgttcccaaa   2340
gagtttaatg ctgaaacatt caccttccat gcagatatat gcacactttc tgagaaggag   2400
agacaaatca agaaacaaac tgcacttgtt gagctcgtga aacacaagcc caaggcaaca   2460
aaagagcaac tgaaagctgt tatggatgat ttcgcagctt ttgtagagaa gtgctgcaag   2520
gctgacgata aggagacctg ctttgccgag gagggtaaaa aacttgttgc tgcaagtcaa   2580
```

-continued

```
gctgccttag gcttacgtac gcaccaccac caccaccact gagatccggc tgctaacaaa   2640
gcccgaaagg aagctgagtt ggctgctgcc accgctgagc aataactagc ataacccctt   2700
ggggcctcta aacgggtctt gaggggtttt gcggccgcac gacagaaact catctcagaa   2760
gaggatctga atggcgccgc acatcaccat catcaccatt gattctagag ggccctattc   2820
tatagtgtca cctaaatgct agagctcgct gatcagcctc gactgtgcct tctagttgcc   2880
agccatctgt tgtttgcccc tcccccgtgc cttccttgac cctggaaggt gccactccca   2940
ctgtcctttc ctaataaaat gaggaaattg catcgcattg tctgagtagg tgtcattcta   3000
ttctgggggg tggggtgggg caggacagca agggggagga ttgggaagac aatagcaggc   3060
atgctgggga tgcggtgggc tctatggctt ctgaggcgga aagaaccagc tggggctcta   3120
gggggtatcc ccacgcgccc tgtagcggcg cattaagcgc ggcgggtgtg gtggttacgc   3180
gcagcgtgac cgctacactt gccagcgccc tagcgcccgc tcctttcgct ttcttccctt   3240
cctttctcgc cacgttcgcc ggctttcccc gtcaagctct aaatcggggc atccctttag   3300
ggttccgatt tagtgcttta cggcacctcg accccaaaaa acttgattag ggtgatggtt   3360
cacgtagtgg gccatcgccc tgatagacgg tttttcgccc tttgacgttg gagtccacgt   3420
tctttaatag tggactcttg ttccaaactg gaacaacact caaccctatc tcggtctatt   3480
cttttgattt ataagggatt ttggggattt cggcctattg gttaaaaaat gagctgattt   3540
aacaaaaatt taacgcgaat taattctgtg gaatgtgtgt cagttagggt gtggaaagtc   3600
cccaggctcc ccaggcaggc agaagtatgc aaagcatgca tctcaattag tcagcaacca   3660
ggtgtggaaa gtccccaggc tccccagcag gcagaagtat gcaaagcatg catctcaatt   3720
agtcagcaac catagtcccg cccctaactc cgcccatccc gcccctaact ccgcccagtt   3780
ccgcccattc tccgccccat ggctgactaa ttttttttat ttatgcagag gccgaggccg   3840
cctctgcctc tgagctattc cagaagtagt gaggaggctt ttttggaggc ctaggctttt   3900
gcaaaaagct cccgggagct tgtatatcca ttttcggatc tgatcaagag acaggatgag   3960
gatcgtttcg catgattgaa caagatggat tgcacgcagg ttctccggcc gcttgggtgg   4020
agaggctatt cggctatgac tgggcacaac agacaatcgg ctgctctgat gccgccgtgt   4080
tccggctgtc agcgcagggg cgcccggttc tttttgtcaa gaccgacctg tccggtgccc   4140
tgaatgaact gcaggacgag gcagcgcggc tatcgtggct ggccacgacg ggcgttcctt   4200
gcgcagctgt gctcgacgtt gtcactgaag cgggaaggga ctggctgcta ttgggcgaag   4260
tgccggggca ggatctcctg tcatctcacc ttgctcctgc cgagaaagta tccatcatgg   4320
ctgatgcaat gcggcggctg catacgcttg atccggctac ctgcccattc gaccaccaag   4380
cgaaacatcg catcgagcga gcacgtactc ggatggaagc cggtcttgtc gatcaggatg   4440
atctggacga agagcatcag gggctcgcgc cagccgaact gttcgccagg ctcaaggcgc   4500
gcatgcccga cggcgaggat ctcgtcgtga cccatggcga tgcctgcttg ccgaatatca   4560
tggtggaaaa tggccgcttt tctggattca tcgactgtgg ccggctgggt gtggcggacc   4620
gctatcagga catagcgttg gctacccgtg atattgctga agagcttggc ggcgaatggg   4680
ctgaccgctt cctcgtgctt tacggtatcg ccgctcccga ttcgcagcgc atcgccttct   4740
atcgccttct tgacgagttc ttctgagcgg gactctgggg ttcgaaatga ccgaccaagc   4800
gacgcccaac ctgccatcac gagatttcga ttccaccgcc gccttctatg aaaggttggg   4860
cttcggaatc gttttccggg acgccggctg gatgatcctc cagcgcgggg atctcatgct   4920
ggagttcttc gcccacccca acttgtttat tgcagcttat aatggttaca aataaagcaa   4980
```

-continued

```
tagcatcaca aatttcacaa ataaagcatt tttttcactg cattctagtt gtggtttgtc   5040
caaactcatc aatgtatctt atcatgtctg tataccgtcg acctctagct agagcttggc   5100
gtaatcatgg tcatagctgt ttcctgtgtg aaattgttat ccgctcacaa ttccacacaa   5160
catacgagcc ggaagcataa agtgtaaagc ctggggtgcc taatgagtga gctaactcac   5220
attaattgcg ttgcgctcac tgcccgcttt ccagtcggga aacctgtcgt gccagctgca   5280
ttaatgaatc ggccaacgcg cggggagagg cggtttgcgt attgggcgct cttccgcttc   5340
ctcgctcact gactcgctgc gctcggtcgt tcggctgcgg cgagcggtat cagctcactc   5400
aaaggcggta atacggttat ccacagaatc aggggataac gcaggaaaga acatgtgagc   5460
aaaaggccag caaaaggcca ggaaccgtaa aaaggccgcg ttgctggcgt ttttccatag   5520
gctccgcccc cctgacgagc atcacaaaaa tcgacgctca agtcagaggt ggcgaaaccc   5580
gacaggacta taaagatacc aggcgtttcc ccctggaagc tccctcgtgc gctctcctgt   5640
tccgaccctg ccgcttaccg gatacctgtc cgcctttctc ccttcgggaa gcgtggcgct   5700
ttctcaatgc tcacgctgta ggtatctcag ttcggtgtag gtcgttcgct ccaagctggg   5760
ctgtgtgcac gaaccccccg ttcagcccga ccgctgcgcc ttatccggta actatcgtct   5820
tgagtccaac ccggtaagac acgacttatc gccactggca gcagccactg gtaacaggat   5880
tagcagagcg aggtatgtag gcggtgctac agagttcttg aagtggtggc ctaactacgg   5940
ctacactaga aggacagtat ttggtatctg cgctctgctg aagccagtta ccttcggaaa   6000
aagagttggt agctcttgat ccggcaaaca aaccaccgct ggtagcggtg gtttttttgt   6060
ttgcaagcag cagattacgc gcagaaaaaa aggatctcaa gaagatcctt tgatcttttc   6120
tacggggtct gacgctcagt ggaacgaaaa ctcacgttaa gggattttgg tcatgagatt   6180
atcaaaaagg atcttcacct agatcctttt aaattaaaaa tgaagtttta aatcaatcta   6240
aagtatatat gagtaaactt ggtctgacag ttaccaatgc ttaatcagtg aggcacctat   6300
ctcagcgatc tgtctatttc gttcatccat agttgcctga ctccccgtcg tgtagataac   6360
tacgatacgg gagggcttac catctggccc cagtgctgca atgataccgc gagacccacg   6420
ctcaccggct ccagatttat cagcaataaa ccagccagcc ggaagggccg agcgcagaag   6480
tggtcctgca actttatccg cctccatcca gtctattaat tgttgccggg aagctagagt   6540
aagtagttcg ccagttaata gtttgcgcaa cgttgttgcc attgctacag gcatcgtggt   6600
gtcacgctcg tcgtttggta tggcttcatt cagctccggt tcccaacgat caaggcgagt   6660
tacatgatcc cccatgttgt gcaaaaaagc ggttagctcc ttcggtcctc cgatcgttgt   6720
cagaagtaag ttggccgcag tgttatcact catggttatg gcagcactgc ataattctct   6780
tactgtcatg ccatccgtaa gatgcttttc tgtgactggt gagtactcaa ccaagtcatt   6840
ctgagaatag tgtatgcggc gaccgagttg ctcttgcccg gcgtcaatac gggataatac   6900
cgcgccacat agcagaactt taaaagtgct catcattgga aaacgttctt cggggcgaaa   6960
actctcaagg atcttaccgc tgttgagatc cagttcgatg taacccactc gtgcacccaa   7020
ctgatcttca gcatctttta ctttcaccag cgtttctggg tgagcaaaaa caggaaggca   7080
aaatgccgca aaaaagggaa taagggcgac acggaaatgt tgaatactca tactcttcct   7140
ttttcaatat tattgaagca tttatcaggg ttattgtctc atgagcggat acatatttga   7200
atgtatttag aaaaataaac aaataggggt tccgcgcaca tttccccgaa aagtgccacc   7260
tgacgtcg                                                            7268
```

<210> SEQ ID NO 23
<211> LENGTH: 8834
<212> TYPE: DNA
<213> ORGANISM: Artificial sequence
<220> FEATURE:
<223> OTHER INFORMATION: Bivalent anti FcgR1-PspA-HuSA

<400> SEQUENCE: 23
acggatcggg agatctcccg atcccctatg gtcgactctc agtacaatct gctctgatgc 60
cgcatagtta agccagtatc tgctccctgc ttgtgtgttg gaggtcgctg agtagtgcgc 120
gagcaaaatt taagctacaa caaggcaagg cttgaccgac aattgcatga agaatctgct 180
tagggttagg cgttttgcgc tgcttcgcga tgtacgggcc agatatacgc gttgacattg 240
attattgact agttattaat agtaatcaat tacggggtca ttagttcata gcccatatat 300
ggagttccgc gttacataac ttacggtaaa tggcccgcct ggctgaccgc ccaacgaccc 360
ccgcccattg acgtcaataa tgacgtatgt tcccatagta acgccaatag ggactttcca 420
ttgacgtcaa tgggtggact atttacggta aactgcccac ttggcagtac atcaagtgta 480
tcatatgcca agtacgcccc ctattgacgt caatgacggt aaatggcccg cctggcatta 540
tgcccagtac atgaccttat gggactttcc tacttggcag tacatctacg tattagtcat 600
cgctattacc atggtgatgc ggttttggca gtacatcaat gggcgtggat agcggtttga 660
ctcacgggga tttccaagtc tccaccccat tgacgtcaat gggagtttgt tttggcacca 720
aaatcaacgg gactttccaa aatgtcgtaa caactccgcc ccattgacgc aaatgggcgg 780
taggcgtgta cggtgggagg tctatataag cagagctctc tggctaacta gagaacccac 840
tgcttactgg cttatcgaaa ttaatacgac tcactatagg gagacccaag cttcaccatg 900
ggatggagct gtatcatcct cttcttggtg gccacagcta ccggtgtcca ctccgatatc 960
cagctgaccc agagcccaag cagcctgagc gccagcgtgg gtgacagagt gaccatcacc 1020
tgtaagtcca gtcaaagtgt tttatacagt tcaaatcaga agaactactt ggcctggtac 1080
cagcagaagc caggtaaggc tccaaagctg ctgatctact gggcatccac tagggaatct 1140
ggtgtgccaa gcagattcag cggtagcggt agcggtaccg acttcacctt caccatcagc 1200
agcctccagc cagaggacat cgccacctac tactgccatc aatacctctc ctcgtggacg 1260
ttcggccaag ggaccaaggt ggaaatcaag agctctggcg gtggcggctc cggaggtgga 1320
ggcagcggag ggggtggatc cgaggtccaa ctggtggaga gcggtggagg tgttgtgcaa 1380
cctggccggt ccctgcgcct gtcctgctcc tcgtctggct tcattttcag tgacaattac 1440
atgtattggg tgagacaggc acctggaaaa ggtcttgagt gggttgcaac cattagtgat 1500
ggtggtagtt acacctacta tccagacagt gtgaagggaa gatttacaat atcgagagac 1560
aacagcaaga acacattgtt cctgcaaatg gacagcctga gacccgaaga caccggggtc 1620
tatttttgtg caagaggcta ctataggtac gagggggcta tggactactg gggccaaggg 1680
accccggtca ccgtctcctc aggctcgacc ggtgggggag gctcgaccag cgctggaggc 1740
ggaggttcta gtgacatcca gctgacccag agcccaagca gcctgagcgc cagcgtgggt 1800
gacagagtga ccatcacctg taagtccagt caaagtgttt tatacagttc aaatcagaag 1860
aactacttgg cctggtacca gcagaagcca ggtaaggctc caaagctgct gatctactgg 1920
gcatccacta gggaatctgg tgtgccaagc agattcagcg gtagcggtag cggtaccgac 1980
ttcaccttca ccatcagcag cctccagcca gaggacatcg ccacctacta ctgccatcaa 2040
tacctctcct cgtggacgtt cggccaaggg accaaggtgg aaatcaagag ctctggcggt 2100
ggcggctccg gaggtggagg cagcggaggg ggtggatccg aggtccaact ggtggagagc 2160
ggtggaggtg ttgtgcaacc tggccggtcc ctgcgcctgt cctgctcctc gtctggcttc 2220
attttcagtg acaattacat gtattgggtg agacaggcac ctggaaaagg tcttgagtgg 2280
gttgcaacca ttagtgatgg tggtagttac acctactatc cagacagtgt gaagggaaga 2340
tttacaatat cgagagacaa cagcaagaac acattgttcc tgcaaatgga cagcctgaga 2400
cccgaagaca ccggggtcta tttttgtgca agaggctact ataggtacga gggggctatg 2460
gactactggg gccaagggac cccggtcacc gtctcctcag gctcgaccgg tgggggaggc 2520
tcgactgcta gcgaattcat ggaagaatct cccgtagcca gtcagtctaa agctgagaaa 2580
gactatgatg cagcgaagaa agatgctaag aatgcgaaaa aagcagtaga agatgctcaa 2640
aaggctttag atgatgcaaa agctgctcag aaaaaatatg acgaggatca gaagaaaact 2700
gaggagaaag ccgcgctaga aaaagcagcg tctgaagaga tggataaggc agtggcagca 2760
gttcaacaag cgtatctagc ctatcaacaa gctacagaca aagccgcaaa agacgcagca 2820
gataagatga tagatgaagc taagaaacgc gaagaagagg caaaaactaa atttaatact 2880
gttcgagcaa tggtagttcc tgagccagag cagttggctg agactaagaa aaaatcagaa 2940
gaagctaaac aaaaagcacc agaacttact aaaaaactag aagaagctaa agcaaaatta 3000
gaagaggctg agaaaaaagc tactgaagcc aaacaaaaag tggatgctga agaagtcgct 3060
cctcaagcta aaatcgctga attggaaaat caagttcata gactagaaca agagctcaaa 3120
gagattgatg agtctgaatc agaagattat gctaaagaag gtttccgtgc tcctcttcaa 3180
tctaaattgg atgccaaaaa agctaaacta tcaaaacttg aagagttaag tgataagatt 3240
gatgagttag acgctgaaat tgcaaaactt gaagatcaac ttaaagctgc tgaagaaaac 3300
aataatgtag aagactactt taaagaaggt ttagagaaaa ctattgctgc taaaaaagct 3360
gaattagaaa aaactgaagc tgaccttaag aaagcagtta atgagccaga aaaaccagct 3420
ccagctccag aaactccagc cccagaactc gagggtggat caggcggttg tacactagag 3480
aagtgctgtg ccgctgcaga tcctcatgaa tgctatgcca aagtgttcga tgaatttaaa 3540
cctcttgtgg aagagcctca gaatttaatc aaacaaaatt gtgagctttt tgagcagctt 3600
ggagagtaca aattccagaa tgcgctatta gttcgttaca ccaagaaagt accccaagtg 3660
tcaactccaa ctcttgtaga ggtctcaaga aacctaggaa aagtgggcag caaatgttgt 3720
aaacatcctg aagcaaaaag aatgccctgt gcagaagact atctatccgt ggtcctgaac 3780
cagttatgtg tgttgcatga gaaaacgcca gtaagtgaca gagtcaccaa atgctgcaca 3840
gaatccttgg tgaacaggcg accatgcttt tcagctctgg aagtcgatga aacatacgtt 3900
cccaaagagt ttaatgctga aacattcacc ttccatgcag atatatgcac actttctgag 3960
aaggagagac aaatcaagaa acaaactgca cttgttgagc tcgtgaaaca caagcccaag 4020
gcaacaaaag agcaactgaa agctgttatg gatgatttcg cagcttttgt agagaagtgc 4080
tgcaaggctg acgataagga gacctgcttt gccgaggagg gtaaaaaact tgttgctgca 4140
agtcaagctg ccttaggctt acgtacgcac caccaccacc accactgaga tccggctgct 4200
aacaaagccc gaaaggaagc tgagttggct gctgccaccg ctgagcaata actagcataa 4260
ccccttgggg cctctaaacg ggtcttgagg ggttttgcgg ccgcacgaca gaaactcatc 4320
tcagaagagg atctgaatgg cgccgcacat caccatcatc accattgatt ctagagggcc 4380
ctattctata gtgtcaccta aatgctagag ctcgctgatc agcctcgact gtgccttcta 4440
gttgccagcc atctgttgtt tgcccctccc ccgtgccttc cttgaccctg gaaggtgcca 4500
ctcccactgt cctttcctaa taaaatgagg aaattgcatc gcattgtctg agtaggtgtc 4560
attctattct ggggggtggg gtggggcagg acagcaaggg ggaggattgg gaagacaata 4620
gcaggcatgc tggggatgcg gtgggctcta tggcttctga ggcggaaaga accagctggg 4680
gctctagggg gtatccccac gcgccctgta gcggcgcatt aagcgcggcg ggtgtggtgg 4740
ttacgcgcag cgtgaccgct acacttgcca gcgccctagc gcccgctcct ttcgctttct 4800
tcccttcctt tctcgccacg ttcgccggct ttccccgtca agctctaaat cggggcatcc 4860
ctttagggtt ccgatttagt gctttacggc acctcgaccc caaaaaactt gattagggtg 4920
atggttcacg tagtgggcca tcgccctgat agacggtttt tcgccctttg acgttggagt 4980
ccacgttctt taatagtgga ctcttgttcc aaactggaac aacactcaac cctatctcgg 5040
tctattcttt tgatttataa gggattttgg ggatttcggc ctattggtta aaaaatgagc 5100
tgatttaaca aaaatttaac gcgaattaat tctgtggaat gtgtgtcagt tagggtgtgg 5160
aaagtcccca ggctccccag gcaggcagaa gtatgcaaag catgcatctc aattagtcag 5220
caaccaggtg tggaaagtcc ccaggctccc cagcaggcag aagtatgcaa agcatgcatc 5280
tcaattagtc agcaaccata gtcccgcccc taactccgcc catcccgccc ctaactccgc 5340
ccagttccgc ccattctccg ccccatggct gactaatttt ttttatttat gcagaggccg 5400
aggccgcctc tgcctctgag ctattccaga agtagtgagg aggctttttt ggaggcctag 5460
gcttttgcaa aaagctcccg ggagcttgta tatccatttt cggatctgat caagagacag 5520
gatgaggatc gtttcgcatg attgaacaag atggattgca cgcaggttct ccggccgctt 5580
gggtggagag gctattcggc tatgactggg cacaacagac aatcggctgc tctgatgccg 5640
ccgtgttccg gctgtcagcg caggggcgcc cggttctttt tgtcaagacc gacctgtccg 5700
gtgccctgaa tgaactgcag gacgaggcag cgcggctatc gtggctggcc acgacgggcg 5760
ttccttgcgc agctgtgctc gacgttgtca ctgaagcggg aagggactgg ctgctattgg 5820
gcgaagtgcc ggggcaggat ctcctgtcat ctcaccttgc tcctgccgag aaagtatcca 5880
tcatggctga tgcaatgcgg cggctgcata cgcttgatcc ggctacctgc ccattcgacc 5940
accaagcgaa acatcgcatc gagcgagcac gtactcggat ggaagccggt cttgtcgatc 6000
aggatgatct ggacgaagag catcaggggc tcgcgccagc cgaactgttc gccaggctca 6060
aggcgcgcat gcccgacggc gaggatctcg tcgtgaccca tggcgatgcc tgcttgccga 6120
atatcatggt ggaaaatggc cgcttttctg gattcatcga ctgtggccgg ctgggtgtgg 6180
cggaccgcta tcaggacata gcgttggcta cccgtgatat tgctgaagag cttggcggcg 6240
aatgggctga ccgcttcctc gtgctttacg gtatcgccgc tcccgattcg cagcgcatcg 6300
ccttctatcg ccttcttgac gagttcttct gagcgggact ctggggttcg aaatgaccga 6360
ccaagcgacg cccaacctgc catcacgaga tttcgattcc accgccgcct tctatgaaag 6420
gttgggcttc ggaatcgttt tccgggacgc cggctggatg atcctccagc gcggggatct 6480
catgctggag ttcttcgccc accccaactt gtttattgca gcttataatg gttacaaata 6540
aagcaatagc atcacaaatt tcacaaataa agcatttttt tcactgcatt ctagttgtgg 6600
tttgtccaaa ctcatcaatg tatcttatca tgtctgtata ccgtcgacct ctagctagag 6660
cttggcgtaa tcatggtcat agctgtttcc tgtgtgaaat tgttatccgc tcacaattcc 6720
acacaacata cgagccggaa gcataaagtg taaagcctgg ggtgcctaat gagtgagcta 6780
actcacatta attgcgttgc gctcactgcc cgctttccag tcgggaaacc tgtcgtgcca 6840

```
gctgcattaa tgaatcggcc aacgcgcggg gagaggcggt ttgcgtattg ggcgctcttc   6900

cgcttcctcg ctcactgact cgctgcgctc ggtcgttcgg ctgcggcgag cggtatcagc   6960

tcactcaaag gcggtaatac ggttatccac agaatcaggg gataacgcag gaaagaacat   7020

gtgagcaaaa ggccagcaaa aggccaggaa ccgtaaaaag gccgcgttgc tggcgttttt   7080

ccataggctc cgcccccctg acgagcatca caaaaatcga cgctcaagtc agaggtggcg   7140

aaacccgaca ggactataaa gataccaggc gtttccccct ggaagctccc tcgtgcgctc   7200

tcctgttccg accctgccgc ttaccggata cctgtccgcc tttctccctt cgggaagcgt   7260

ggcgctttct caatgctcac gctgtaggta tctcagttcg gtgtaggtcg ttcgctccaa   7320

gctgggctgt gtgcacgaac cccccgttca gcccgaccgc tgcgccttat ccggtaacta   7380

tcgtcttgag tccaacccgg taagacacga cttatcgcca ctggcagcag ccactggtaa   7440

caggattagc agagcgaggt atgtaggcgg tgctacagag ttcttgaagt ggtggcctaa   7500

ctacggctac actagaagga cagtatttgg tatctgcgct ctgctgaagc cagttacctt   7560

cggaaaaaga gttggtagct cttgatccgg caaacaaacc accgctggta gcggtggttt   7620

ttttgtttgc aagcagcaga ttacgcgcag aaaaaaagga tctcaagaag atcctttgat   7680

cttttctacg gggtctgacg ctcagtggaa cgaaaactca cgttaaggga ttttggtcat   7740

gagattatca aaaaggatct tcacctagat ccttttaaat taaaaatgaa gttttaaatc   7800

aatctaaagt atatatgagt aaacttggtc tgacagttac caatgcttaa tcagtgaggc   7860

acctatctca gcgatctgtc tatttcgttc atccatagtt gcctgactcc ccgtcgtgta   7920

gataactacg atacgggagg gcttaccatc tggccccagt gctgcaatga taccgcgaga   7980

cccacgctca ccggctccag atttatcagc aataaaccag ccagccggaa gggccgagcg   8040

cagaagtggt cctgcaactt tatccgcctc catccagtct attaattgtt gccgggaagc   8100

tagagtaagt agttcgccag ttaatagttt gcgcaacgtt gttgccattg ctacaggcat   8160

cgtggtgtca cgctcgtcgt ttggtatggc ttcattcagc tccggttccc aacgatcaag   8220

gcgagttaca tgatccccca tgttgtgcaa aaaagcggtt agctccttcg gtcctccgat   8280

cgttgtcaga agtaagttgg ccgcagtgtt atcactcatg gttatggcag cactgcataa   8340

ttctcttact gtcatgccat ccgtaagatg cttttctgtg actggtgagt actcaaccaa   8400

gtcattctga gaatagtgta tgcggcgacc gagttgctct tgcccggcgt caatacggga   8460

taataccgcg ccacatagca gaactttaaa agtgctcatc attggaaaac gttcttcggg   8520

gcgaaaactc tcaaggatct taccgctgtt gagatccagt tcgatgtaac ccactcgtgc   8580

acccaactga tcttcagcat cttttacttt caccagcgtt tctgggtgag caaaaacagg   8640

aaggcaaaat gccgcaaaaa agggaataag ggcgacacgg aaatgttgaa tactcatact   8700

cttccttttt caatattatt gaagcattta tcagggttat tgtctcatga gcggatacat   8760

atttgaatgt atttagaaaa ataaacaaat aggggttccg cgcacatttc cccgaaaagt   8820

gccacctgac gtcg                                                     8834
```

<210> SEQ ID NO 24
<211> LENGTH: 258
<212> TYPE: PRT
<213> ORGANISM: Artificial sequence
<220> FEATURE:
<223> OTHER INFORMATION: Anti-FcgR1 sequence

<400> SEQUENCE: 24

```
Asp Ile Gln Leu Thr Gln Ser Pro Ser Ser Leu Ser Ala Ser Val Gly
1               5                   10                  15

Asp Arg Val Thr Ile Thr Cys Lys Ser Ser Gln Ser Val Leu Tyr Ser
            20                  25                  30

Ser Asn Gln Lys Asn Tyr Leu Ala Trp Tyr Gln Gln Lys Pro Gly Lys
        35                  40                  45

Ala Pro Lys Leu Leu Ile Tyr Trp Ala Ser Thr Arg Glu Ser Gly Val
    50                  55                  60

Pro Ser Arg Phe Ser Gly Ser Gly Ser Gly Thr Asp Phe Thr Phe Thr
65                  70                  75                  80

Ile Ser Ser Leu Gln Pro Glu Asp Ile Ala Thr Tyr Tyr Cys His Gln
                85                  90                  95

Tyr Leu Ser Ser Trp Thr Phe Gly Gln Gly Thr Lys Val Glu Ile Lys
            100                 105                 110

Ser Ser Gly Gly Gly Gly Ser Gly Gly Gly Gly Ser Gly Gly Gly Gly
        115                 120                 125

Ser Glu Val Gln Leu Val Glu Ser Gly Gly Gly Val Val Gln Pro Gly
    130                 135                 140

Arg Ser Leu Arg Leu Ser Cys Ser Ser Ser Gly Phe Ile Phe Ser Asp
145                 150                 155                 160

Asn Tyr Met Tyr Trp Val Arg Gln Ala Pro Gly Lys Gly Leu Glu Trp
                165                 170                 175

Val Ala Thr Ile Ser Asp Gly Gly Ser Tyr Thr Tyr Tyr Pro Asp Ser
            180                 185                 190

Val Lys Gly Arg Phe Thr Ile Ser Arg Asp Asn Ser Lys Asn Thr Leu
        195                 200                 205

Phe Leu Gln Met Asp Ser Leu Arg Pro Glu Asp Thr Gly Val Tyr Phe
    210                 215                 220

Cys Ala Arg Gly Tyr Tyr Arg Tyr Glu Gly Ala Met Asp Tyr Trp Gly
225                 230                 235                 240

Gln Gly Thr Pro Val Thr Val Ser Ser Gly Ser Thr Gly Gly Gly Gly
                245                 250                 255

Ser Thr


<210> SEQ ID NO 25
<211> LENGTH: 229
<212> TYPE: PRT
<213> ORGANISM: Artificial sequence
<220> FEATURE:
<223> OTHER INFORMATION: Human Serum Albumin fragment (FcRn binding)

<400> SEQUENCE: 25

Leu Glu Lys Cys Cys Ala Ala Ala Asp Pro His Glu Cys Tyr Ala Lys
1               5                   10                  15

Val Phe Asp Glu Phe Lys Pro Leu Val Glu Glu Pro Gln Asn Leu Ile
            20                  25                  30

Lys Gln Asn Cys Glu Leu Phe Glu Gln Leu Gly Glu Tyr Lys Phe Gln
        35                  40                  45

Asn Ala Leu Leu Val Arg Tyr Thr Lys Lys Val Pro Gln Val Ser Thr
    50                  55                  60

Pro Thr Leu Val Glu Val Ser Arg Asn Leu Gly Lys Val Gly Ser Lys
65                  70                  75                  80

Cys Cys Lys His Pro Glu Ala Lys Arg Met Pro Cys Ala Glu Asp Tyr
                85                  90                  95

Leu Ser Val Val Leu Asn Gln Leu Cys Val Leu His Glu Lys Thr Pro
```

-continued

```
            100                 105                 110

Val Ser Asp Arg Val Thr Lys Cys Cys Thr Glu Ser Leu Val Asn Arg
        115                 120                 125

Arg Pro Cys Phe Ser Ala Leu Glu Val Asp Glu Thr Tyr Val Pro Lys
    130                 135                 140

Glu Phe Asn Ala Glu Thr Phe Thr Phe His Ala Asp Ile Cys Thr Leu
145                 150                 155                 160

Ser Glu Lys Glu Arg Gln Ile Lys Lys Gln Thr Ala Leu Val Glu Leu
                165                 170                 175

Val Lys His Lys Pro Lys Ala Thr Lys Glu Gln Leu Lys Ala Val Met
            180                 185                 190

Asp Asp Phe Ala Ala Phe Val Glu Lys Cys Cys Lys Ala Asp Asp Lys
        195                 200                 205

Glu Thr Cys Phe Ala Glu Glu Gly Lys Lys Leu Val Ala Ala Ser Gln
    210                 215                 220

Ala Ala Leu Gly Leu
225
```